US012802815B2

(12) United States Patent
Oliveira et al.

(10) Patent No.: US 12,802,815 B2
(45) Date of Patent: Nov. 17, 2026

(54) METHOD FOR IDENTIFICATION OF CANCER PATIENTS WITH DURABLE BENEFIT FROM IMMUNOTHERAPY IN OVERALL POOR PROGNOSIS SUBGROUPS

(71) Applicant: BIODESIX, INC., Boulder, CO (US)

(72) Inventors: Carlos Oliveira, Steamboat Springs, CO (US); Heinrich Roder, Steamboat Springs, CO (US); Julia Grigorieva, Steamboat Springs, CO (US); Joanna Roder, Steamboat Springs, CO (US)

(73) Assignee: Biodesix, Inc., Louisville, CO (US)

( * ) Notice: Subject to any disclaimer, the term of this patent is extended or adjusted under 35 U.S.C. 154(b) by 1005 days.

(21) Appl. No.: 17/495,213

(22) Filed: Oct. 6, 2021

(65) Prior Publication Data

US 2022/0026416 A1 Jan. 27, 2022

Related U.S. Application Data

(63) Continuation of application No. 16/475,752, filed as application No. PCT/US2018/012564 on Jan. 5, 2018, now Pat. No. 11,150,238.

(60) Provisional application No. 62/442,557, filed on Jan. 5, 2017.

(51) Int. Cl.

| | |
|---|---|
| ***G16H 50/20*** | (2018.01) |
| ***G01N 33/68*** | (2006.01) |
| ***G06F 18/243*** | (2023.01) |
| *G06F 18/2413* | (2023.01) |

(52) U.S. Cl.

CPC ......... *G16H 50/20* (2018.01); *G01N 33/6851* (2013.01); *G06F 18/24323* (2023.01); *G01N 2800/52* (2013.01); *G01N 2800/7028* (2013.01); *G06F 18/2413* (2023.01)

(58) Field of Classification Search

CPC ........... G06F 18/2413; G06F 18/24323; G06F 18/24147; G01N 33/5091; G01N 33/57423; G01N 33/5743; G01N 33/57438; G01N 33/6851; G01N 2800/52; G01N 2800/7028; G01N 33/574; G01N 27/62; G16B 40/10; G16B 40/20; G16B 20/00; G16H 10/40; G16H 10/60; G16H 20/10; G16H 50/20; G16H 50/30; G16H 70/40; G16H 50/70

See application file for complete search history.

(56) References Cited

U.S. PATENT DOCUMENTS

| | | | |
|---|---|---|---|
| 6,569,587 | B2 | 5/2003 | Sasaki et al. |
| 7,736,905 | B2 | 6/2010 | Roder et al. |
| 7,858,389 | B2 | 12/2010 | Roder et al. |
| 7,858,390 | B2 | 12/2010 | Roder et al. |
| 7,867,775 | B2 | 1/2011 | Roder et al. |
| 7,879,620 | B2 | 2/2011 | Roder et al. |
| 7,906,342 | B2 | 3/2011 | Roeder et al. |
| 8,024,282 | B2 | 9/2011 | Tsypin et al. |
| 8,097,469 | B2 | 1/2012 | Roder et al. |
| 8,119,417 | B2 | 2/2012 | Roeder et al. |
| 8,119,418 | B2 | 2/2012 | Roeder et al. |
| 8,467,988 | B1 | 6/2013 | Roder et al. |
| 8,586,379 | B2 | 11/2013 | Roeder et al. |
| 8,586,380 | B2 | 11/2013 | Roeder et al. |
| 8,718,996 | B2 | 5/2014 | Brauns et al. |
| 8,914,238 | B2 | 12/2014 | Roder et al. |
| 9,152,758 | B2 | 10/2015 | Roder et al. |
| 9,211,314 | B2 | 12/2015 | Roder et al. |
| 9,254,120 | B2 | 2/2016 | Roeder et al. |
| 9,279,798 | B2 | 3/2016 | Roder et al. |
| 9,477,906 | B2 | 10/2016 | Roder et al. |
| 9,563,744 | B1 | 2/2017 | Roder et al. |
| 9,606,101 | B2 | 3/2017 | Roder et al. |
| 9,724,413 | B2 | 8/2017 | Maecker et al. |
| 9,779,204 | B2 | 10/2017 | Roder et al. |
| 9,824,182 | B2 | 11/2017 | Roder et al. |
| 10,007,766 | B2 | 6/2018 | Roder et al. |
| 10,037,874 | B2 | 7/2018 | Roder et al. |
| 10,217,620 | B2 | 2/2019 | Roder et al. |
| 10,489,550 | B2 | 11/2019 | Roder et al. |
| 10,713,590 | B2 | 7/2020 | Roder et al. |
| 2003/0225526 | A1 | 12/2003 | Golub et al. |
| 2005/0149269 | A1 | 7/2005 | Thomas et al. |
| 2007/0037143 | A1 | 2/2007 | Jost et al. |

(Continued)

FOREIGN PATENT DOCUMENTS

| | | |
|---|---|---|
| CN | 103339509 A | 10/2013 |
| CN | 103384827 A | 11/2013 |

(Continued)

OTHER PUBLICATIONS

Althammer et al, "Biomarkers and Immune Monitoring", Journal for Immunotherapy of Caner, vol. 4, No. 91, pp. 223-242, Dec 8, 2016.
Biodesix's Diagnostic Cortex™ Platform Used in Three Studies Presented at SITC, Nov. 15, 2016, Retrieved from the Internet Oct. 26, 2020, URL: https://www.biodesix.com/press-releases/biodesixs-diagnostic-cortex-platform-used-three-studies-presented-sitc*.
Blanco et al, "Feature selection in Bayesian classifiers for the prognosis of survival of cirrhotic patients treated with TIPS", Journal of Biomedical Informatics, vol. 38, pp. 376-388, (2005).

(Continued)

*Primary Examiner* — Soren Harward
*Assistant Examiner* — Dawn Bickham
(74) *Attorney, Agent, or Firm* — Lathrop GPM LLP; Lisa Hillman

(57) ABSTRACT

A blood-based sample from a cancer patient is subject to mass spectrometry and the resulting mass spectral data is classified with the aid of a computer to see if the patient is a member of a class of patients having a poor prognosis. If so, the mass spectral data is further classified with the aid of the computer by a second classifier which identifies whether the patient is nevertheless likely to obtain durable benefit from immunotherapy drugs, e.g., immune checkpoint inhibitors, anti-CTLA4 drugs, and high dose interleukin-2.

11 Claims, 20 Drawing Sheets

(56) References Cited

U.S. PATENT DOCUMENTS

| | | | |
|---|---|---|---|
| 2007/0231921 | A1 | 10/2007 | Roder et al. |
| 2007/0269804 | A1 | 11/2007 | Liew |
| 2008/0032299 | A1 | 2/2008 | Burczynski et al. |
| 2008/0306898 | A1 | 12/2008 | Tsypin et al. |
| 2010/0174492 | A1 | 7/2010 | Roder et al. |
| 2010/0240546 | A1 | 9/2010 | Lo et al. |
| 2011/0208433 | A1 | 8/2011 | Grigorieva et al. |
| 2011/0271358 | A1 | 11/2011 | Freeman et al. |
| 2012/0199203 | A1 | 8/2012 | Nishzawa et al. |
| 2013/0131996 | A1 | 5/2013 | Roder et al. |
| 2013/0344111 | A1 | 12/2013 | Roder et al. |
| 2014/0012514 | A1 | 1/2014 | Roder et al. |
| 2014/0044673 | A1 | 2/2014 | Caprioli |
| 2014/0200825 | A1 | 7/2014 | Roder et al. |
| 2014/0341902 | A1 | 11/2014 | Maecker et al. |
| 2015/0071910 | A1 | 3/2015 | Kowanetz et al. |
| 2015/0102216 | A1 | 4/2015 | Roder et al. |
| 2015/0125463 | A1 | 5/2015 | Cogswell et al. |
| 2015/0283206 | A1 | 10/2015 | Roder et al. |
| 2015/0285817 | A1 | 10/2015 | Roder et al. |
| 2016/0018410 | A1 | 1/2016 | Roder et al. |
| 2016/0019342 | A1 | 1/2016 | Roder et al. |
| 2016/0098514 | A1 | 4/2016 | Roder et al. |
| 2016/0163522 | A1 | 6/2016 | Roder et al. |
| 2016/0299146 | A1 | 10/2016 | Garraway et al. |
| 2017/0039345 | A1 | 2/2017 | Roder et al. |
| 2017/0271136 | A1 | 9/2017 | Roder et al. |
| 2018/0021431 | A1 | 1/2018 | Maecker et al. |
| 2018/0027249 | A1 | 1/2018 | Maeda et al. |
| 2019/0018929 | A1 | 1/2019 | Steingrimsson et al. |
| 2019/0035364 | A1 | 1/2019 | Iwasaki |

FOREIGN PATENT DOCUMENTS

| | | | |
|---|---|---|---|
| CN | 103842030 | A | 6/2014 |
| CN | 104470949 | A | 3/2015 |
| CN | 104685360 | A | 6/2015 |
| CN | 105512669 | A | 4/2016 |
| CN | 105745659 | A | 7/2016 |
| EP | 1043676 | A2 | 10/2000 |
| EP | 2241335 | A1 | 10/2010 |
| WO | 2010085234 | A1 | 7/2010 |
| WO | 2012069462 | A1 | 5/2012 |
| WO | 2014003853 | A1 | 1/2014 |
| WO | 2014007859 | A1 | 1/2014 |
| WO | 2014055543 | A2 | 4/2014 |
| WO | 2014149629 | A1 | 9/2014 |
| WO | 2015039021 | A2 | 3/2015 |
| WO | 2015153991 | A1 | 10/2015 |
| WO | 2015157109 | A1 | 10/2015 |
| WO | 2015176033 | A1 | 11/2015 |
| WO | 2016049385 | A1 | 3/2016 |
| WO | 2016054031 | A1 | 4/2016 |
| WO | 2016089553 | A1 | 6/2016 |
| WO | 2017011439 | A1 | 1/2017 |

OTHER PUBLICATIONS

Bruno et al, "Overexpression of PD-1 and PD-L 1 in Penal Cell Carcinoma is associated with poor prognosis in metastatic patients treated with subtinib", Annals of Oncology, vol. 26, No. 2, Annual Meeting Poster, (2015).

Carvajal-Hausdorf et al, "Quantitative Measurement of Cancer Tissue Biomarkers in the Lab and in the Clinic", Lab Invest, vol. 95, No. 4, pp. 385-396, (2015).

Girosi et al, "Regularization Theory and Neural Architectures", Neural Computation, vol. 7, pp. 219-269, (1995).

Grivennikov et al, "Immunity, inflammation, and cancer", Cell, vol. 140, pp. 883-899, (2010).

Gunn et al, "Opposing roles for complement component C5a in tumor progression and the tumor microenvironment", J Immunol, vol. 189, pp. 2985-2994, (2012).

International Search Report and Written Opinion for PCT Application No. PCT/US2016/041860 dated Oct. 6, 2016.

International Search Report for PCT application No. PCT/US17/13920, dated May 19, 2017.

International Search Report for PCT application No. PCT/US2018/12564, dated Mar. 26, 2018.

International Search Report for PCT application No. PCT/US2019/021641, dated Jul. 3, 2019, 7 pages.

Janelle et al, "Role of the complement system in NK cell-mediated antitumor T-cell responses", Oncoimmunology, vol. 3, e27897, (2014).

Janelle et al, "Transient complement inhibition promotes a tumor-specific immune response through the implication of natural killer cells", Cancer Immunol Res, vol. 2, pp. 200-206, (2014).

Jiang et al, "Role of IL-2 in Cancer Immunotherapy", ONcoimmunology, vol. 5, No. 6, May 31, 2016.

Kani et al, "Quantitative Proteomic profiling identifies protein correlates to EGFR kinase inhibition", Mol Cancer Ther., Vo. 11, No. 5, pp. 1071-1081, (2012).

Karpievitch et al, "Liquid Chromatography Mass Spectrometry-Based Proteomics: Biological and Technological Aspects", Ann Appl Stat., vol. 4, No. 4, pp. 1797-1823, (2010).

Kennedy-Crispin et al, "Human keratinocytes' response to injury upregulates CCl20 and other genes linking innate and adaptive immunity", J Invest Dermatol., vol. 132, No. 1, pp. 105-113, (2012).

Larkin et al, "Combined Nivolumab and Ipilimumab or Monotherapy in Untreated Melanoma", The New England Journal of Medicine, vol. 373, No. 1, pp. 23-34, (2015).

Lundqvist et al, "Adoptive Cellular Therapy", Journal for Immunotherapy of Cancer, vol. 4, No. 82, pp. 1-221, Nov. 16, 2016.

Mantovani et al, "Cancer-related inflammation", Nature, vol. 454, pp. 436-444, (2008).

Markiewski et al, "Modulation of the antitumor immune response by complement", Natl Immunol, vol. 9, pp. 1225-1235, (2008).

Mathern et al, "Molecules Great and Small: The Complement System", Clin J Am Soc Nephrol, vol. 10, pp. 1636-1650, (2015).

McDermott et al, "Durable benefit and the potential for long-term survival with immunotherapy in advanced melanoma", Cancer Treatment, vol. 40, No. 9, pp. 1056-1064, Apr. 8, 2014.

Mootha et al, "PGC-1 a-responsive genes involved in oxidative phosphorylation are coordinately downregulated in human diabetes", Nat Genet., vol. 34, No. 3, pp. 267-273, (2003).

Pearson et al, J. Clinical Oncology, vol. 34, No. 15, Meeting Abstract, May 2016.

Pio et al, "The role of complement in tumor growth", Adv Exp Med Biol, vol. 772, pp. 229-262, (2014).

Porta et al, "Cellular and molecular pathways linking inflammation and cancer", Immunobiology, vol. 214, pp. 461-777, (2009).

Postow et al, "Peripheral and tumor immune correlates in patients with advanced melanoma treated with nivolumab (aniti-PD-1, BMS-936558, ONO-4538) monotherapy or in combination with ipilimumab", Journal of Translational Medicine, vol. 12, No. 1, pp. 1-2, (2014).

Qi et al, "Advances in the study of serum tumor markers of lung cancer", Journal of Cancer and Therapeutics, vol. 10, No. 2, pp. C95-C101, (2014).

Redman et al, "Advances in immunotherapy for melanoma", BNC Medicine, vol. 14, No. 1, pp. 1-11, (2016).

Romano et al, "The therapeutic promise of disrupting the PD-1/PD-L1 immune checkpoint in cancer: unleashing the CD8 cell mediated anti-tumor activity results in significant, unprecedented clinical efficacy in various solid tumors", J. Immuno Ther. Can., vol. 3, No. 15, pp. 1-5, (2015).

Shrivastava, "Improving Neural Networks with Dropout", Master's Thesis, Graduate Department of Computer Science, University of Toronto, (2013).

Subramanian et al, "Gene set enrichment analysis: A knowledge-based approach for interpreting genome-wide expression profiles", Proc Natl Acad Sci USA, vol. 102, No. 43, pp. 15545-15550, (2005).

Taguchi et al, "Mass Spectrometry to Classify Non-Small-Cell Lung Cancer Patients for Clinical Outcome after Treatment with Epidermal Growth Factor Receptor Tyrosine Kinase Inhibitors: A Multicohort

(56) References Cited

OTHER PUBLICATIONS

Cross-Institutional Study", UNCI Journal of the National Cancer Institute, vol. 99, No. 11, pp. 838-846, (2007).
Taneja et al, "Markers of Small Cell Lung Cancer", World Journal of Surgical Oncology, vol. 2, No. 10, 5 pages, May 5, 2004.
The National Intellectual Property Administration, P.R. China Serial No. 201880015865.1, First Office Action dated Feb. 26, 2020.
Tibshirani, "Regression shrinkage and selection via the lasso", J. Royal. Statist. Soc B, vol. 58, No. 1, pp. 267-288, (1996).
Tikhonov, "On the stability of inverse problems", Doklady Akademii Nauk SSSR, vol. 39, No. 5, pp. 195-198, (1943).
Vadrevu et al, "Complement c5a receptor facilities cancer metastasis by altering T-cell responses in the metastatic niche", Cancer Res, vol. 74, pp. 3454-3565, (2014).
Vu et al, "RAC1 P29S regulates PD-L1 expression in melanoma", Pigment Cell Melanoma Res., vol. 28, No. 5, pp. 590-598, (2015).
Weber et al, "Pre-treatment selection for nivolumab benefit based on serum mass spectra", Journal for Immunotherapy of Cancer, No. 3, pp. 1-2, Nov. 4, 2015.
Weber et al, "A Serum Protein Signature Associated with Outcome After Anti-PD-1 Therapy in Metastatic Melanoma", ACCR Special Conference on Tumor Immunology and Immunotherapy, Boston, MA, vol. 6, No. 1, pp. 79-86, (2016).
Weber et al, "A test identifying advanced melanoma patients with long survival outcomes on nivolumab shows potential for selection for benefit from combination checkpoint blockade", 31st Annual Meeting and Associated Programs of the Society for Immunotherapy of Cancer, vol. 4, No. 82, (2016).
Weber et al, "Safety, Efficacy, Biomarkers of Nivoluamb With Vaccine in Ipilimumab or -Naïve Melanoma", J. Clin. Oncol., vol. 31, pp. 4311-4318, (2013).
Written Opinion of the International Searching Authority for PCT/US219/021641, dated Jul. 3, 2019, 12 pages.
Zang et al, "Progress in immunotherapy of melanoma", Chinese Journal of Cancer Biotherapy, vol. 20, No. 3, Jun. 30, 2013.
Zhang et al, "A Protective Role for C5a in the Development of Allergic Asthma Associated with Altered Levels of B7—H1 and B7-DC on Plasmacytoid Dendritic Cells", J. Immunol., vol. 182, pp. 5123-5130, (2009).
Zhang et al, "Simultaneous blocking of PD-1 and CTLA-4 increases in T cell infiltration in melanoma and reduces the number of Treg and bone-marrow derived suppressor cells", Progress in Physiological Sciences, vol. 43, No. 2, Dec 31, 2012.

Example plot illustrating how features are defined. Each separate hatched region represents one feature. The y scale shows normalized intensity and the x axis shows m/z.

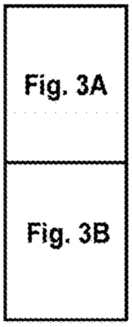
Fig. 3
Fig. 3A
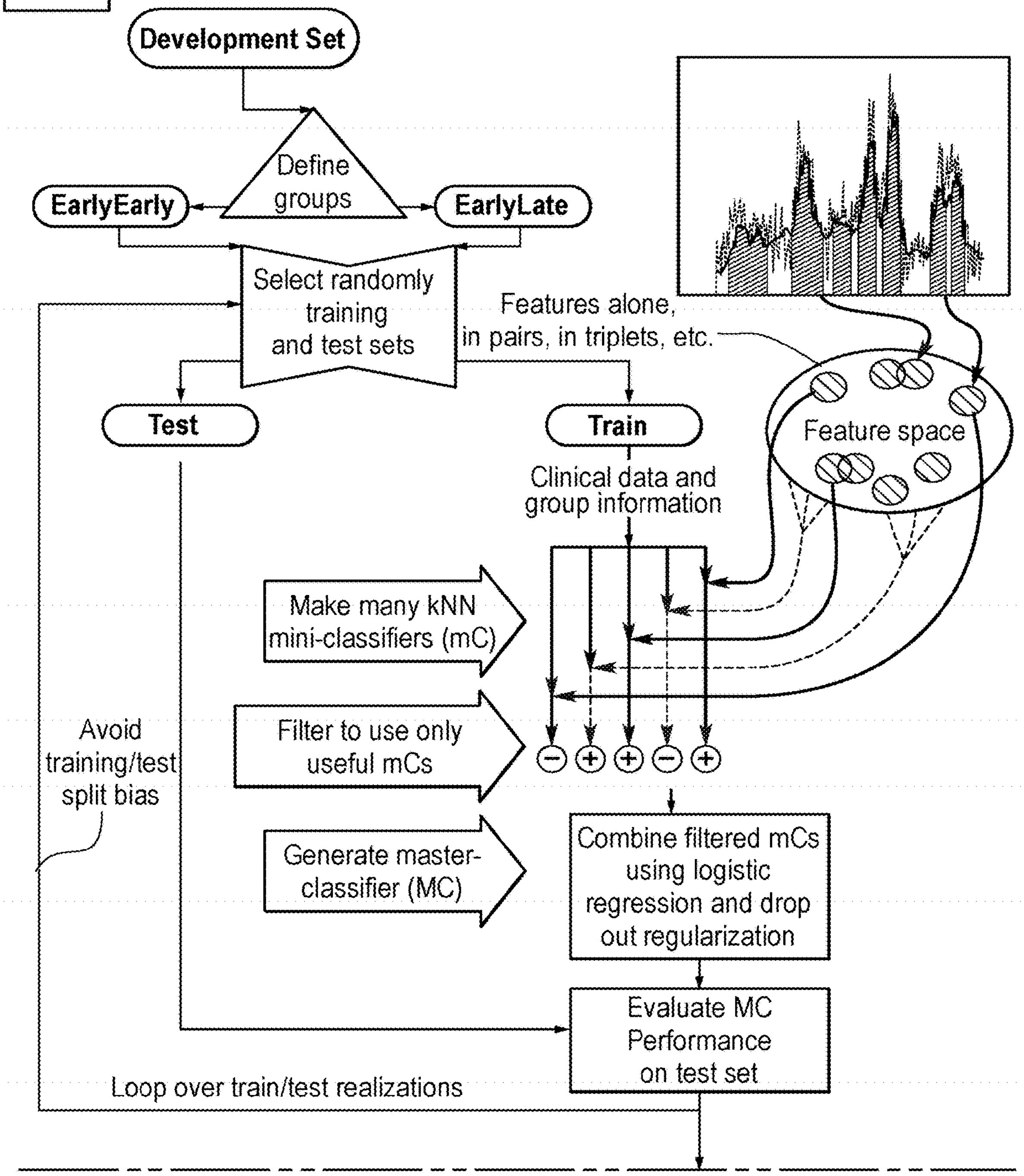

Fig. 13A

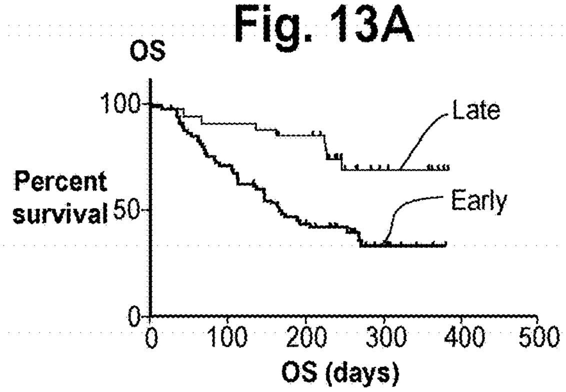

Fig. 13B

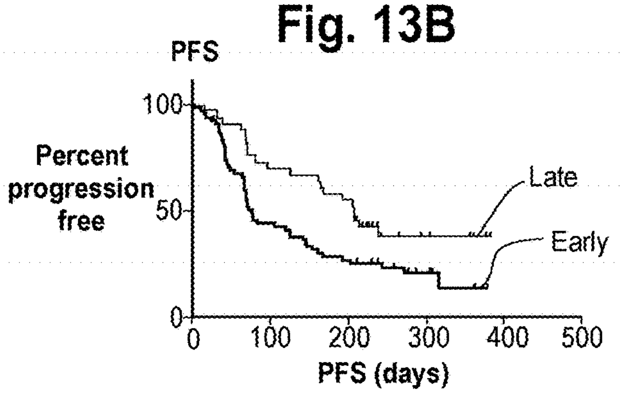

Fig. 14A

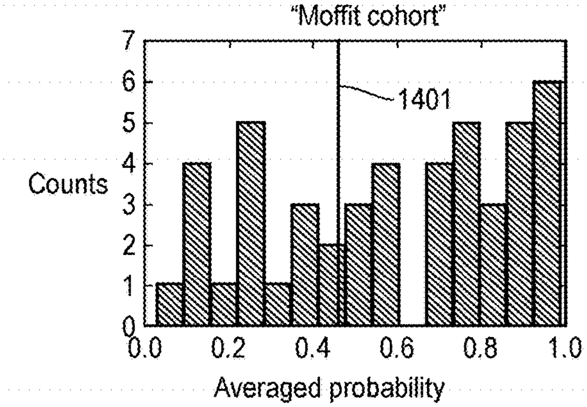

Fig. 14B

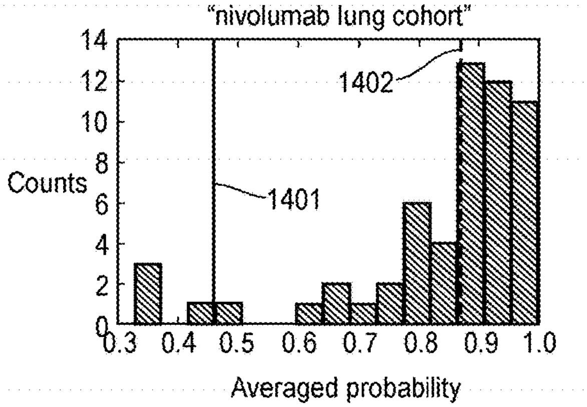

Left (Figure 14A): distribution of the averaged probabilities for the samples in the "Moffitt" cohort that are BDX008-
RIght (Figure 14B): distribution of the averaged probabilities for the samples in the "nivolumab lung" cohort classified as BDX008-
The black vertical lines1401 represent the cutoff of 0.459 that defines the "New classifier 1" and the dashed line 1402 represents the cutoff of 0.869 chosen to define the "New classifier 2"

OS ("NSCLC classifier")

OS ("NSCLC classifier"combined with "New classifier 2")

PFS ("NSCLC classifier")

PFS ("NSCLC classifier"combined with "New classifier 2")

METHOD FOR IDENTIFICATION OF CANCER PATIENTS WITH DURABLE BENEFIT FROM IMMUNOTHERAPY IN OVERALL POOR PROGNOSIS SUBGROUPS

PRIORITY

This application is a continuation of U.S. application Ser. No. 16/475,752, filed Jul. 3, 2019, which is a 371 of International application serial no. PCT/US2018/012564, filed Jan. 5, 2018, which claims priority benefits of U.S. provisional application Ser. No. 62/442,557, filed Jan. 5, 2017, the contents of which are incorporated by reference herein.

RELATED APPLICATION

This application is related to U.S. patent application Ser. No. 15/207,825 filed Jul. 12, 2016, the entire content of which, including appendices, is incorporated by reference herein.

FIELD

This invention relates to the fields of biomarker discovery and cancer treatment. More particularly it relates to methods of guiding cancer patient treatment with immunotherapy drugs, including immune checkpoint inhibitors such as for example antibody drugs blocking ligand activation of the PD-1 checkpoint protein, such as nivolumab. More particularly, this disclosure relates to the discovery of methods for identifying patients who are likely to have long term, durable benefit from immunotherapy drugs, e.g., administration of nivolumab or nivolumab combination therapy (i.e., relatively long term time-to-event outcomes) despite being members of a class of patients who, as a general matter, have a poor prognosis.

BACKGROUND

In our work developing classifiers with application for treatment guidance in the immunotherapy setting, see U.S. patent application Ser. No. 15/207,825 filed Jul. 12, 2016, we have described a mass spectrometry test which is performed on a blood based sample in advance of treatment of a cancer patient which identifies or classifies a sample as a member of a group with different (i.e., better or worse) outcomes in treatment with immunotherapy drugs. The test makes use of a computer configured as a classifier which is described in that document in Example 1, at pages 27-68 as the "full set, approach 1 classifier", or "IS2". This test is also described interchangeably in this document as BDX008. This test classifies a patient sample into the BDX008− ("Early" class label in the nomenclature of IS2) and BDX008+ groups ("Late" class label in the nomenclature of IS2) according to the likelihood of their benefit from treatment with nivolumab. In particular, if the patient is classified with the Early class label, they are predicted to have relatively little benefit whereas the Late class label predicts that the patient is likely to have substantial benefit from the treatment.

FIGS. 1A and 1B show the Kaplan-Meier plots for Overall Survival (OS) and Progression-free Survival (PFS) by BDX008− and BDX008+ classification groups for the patient cohort used in the development of the BDX008 classifier: 119 samples obtained from melanoma patients taken before treatment with nivolumab, referred to in this document as the "Moffitt set." Further details on the development of the BDX008 classifier are described in the '825 application filed Jul. 12, 2016, Example 1.

The test achieved a good performance for the split of the patients according to their outcome under treatment with nivolumab: Hazard Ratio (HR) of 0.38 (95% CI of 0.19-0.55) for OS with a median of 61 weeks for the BDX008− group and not reached for the BDX008+ group; HR of 0.50 (95% CI of 0.29-0.71) for PFS with medians of 84 days for the BDX008-group and 230 days for the BDX008+ group. In the development set, the classifier assigned 47 samples to the BDX008− group and 72 to the BDX008+ group.

This performance is considered good, but some samples from patients with long outcomes are still classified as being BDX008−, as can be observed in the long tails (plateaus) of the Early curves of FIG. 1A-1B, for both OS and PFS. Namely, 7 patients (out of 31) with Partial Response (PR) to the treatment are assigned to this poor prognosis group. This behavior was observed also in other sample sets used for the validation of the BDX008 test.

This document describes new classifiers (i.e., programmed computers with stored reference data and classification algorithms) and practical tests whose goal is to identify, among the samples classified as BDX008− (and in other subgroups of patients with poor prognosis, as will be described subsequently), which ones are likely to have long term, durable benefit from immunotherapy, i.e., relatively longer time-to-event outcomes. The classifiers and tests are particularly applicable to guide immunotherapy for melanoma and lung cancer patients. This document also describes tests which are able to identify cancer patients with particularly poor or bad prognosis on immunotherapy.

BRIEF DESCRIPTION OF THE DRAWINGS

FIGS. 13A-13B are Kaplan-Meier plots for OS and PFS split by final classifications of the NSCLC classifier for the nivolumab lung cohort.

FIG. 14A is a distribution of the averaged probabilities for the samples in the "Moffitt" cohort that are BDX008−: FIG. 14B is a distribution of the averaged probabilities for the samples in the "nivolumab lung" cohort classified as BDX008−. The vertical lines 1401 represent the cutoff of 0.459 that defines the "New classifier 1" and line 1402 represents the cutoff of 0.869 chosen to define the "New classifier 2".

DETAILED DESCRIPTION

Overview and Summary

Figure 1A:
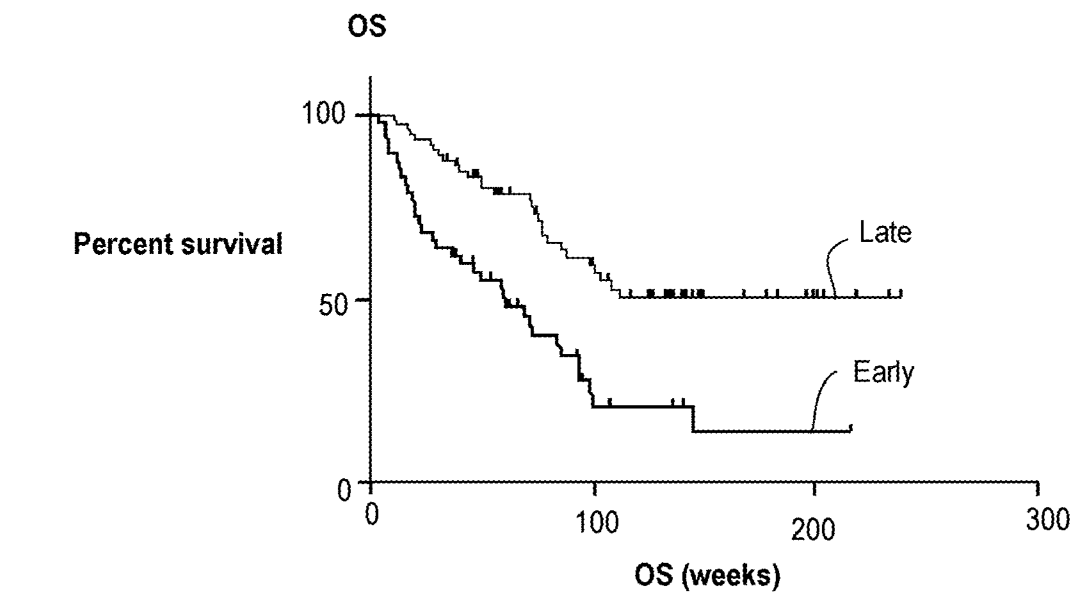
FIGS. 1A-1B are Kaplan-Meier plots for OS and PFS by BDX008− and BDX008+ classification groups for the "Moffitt set".
Figure 1B:
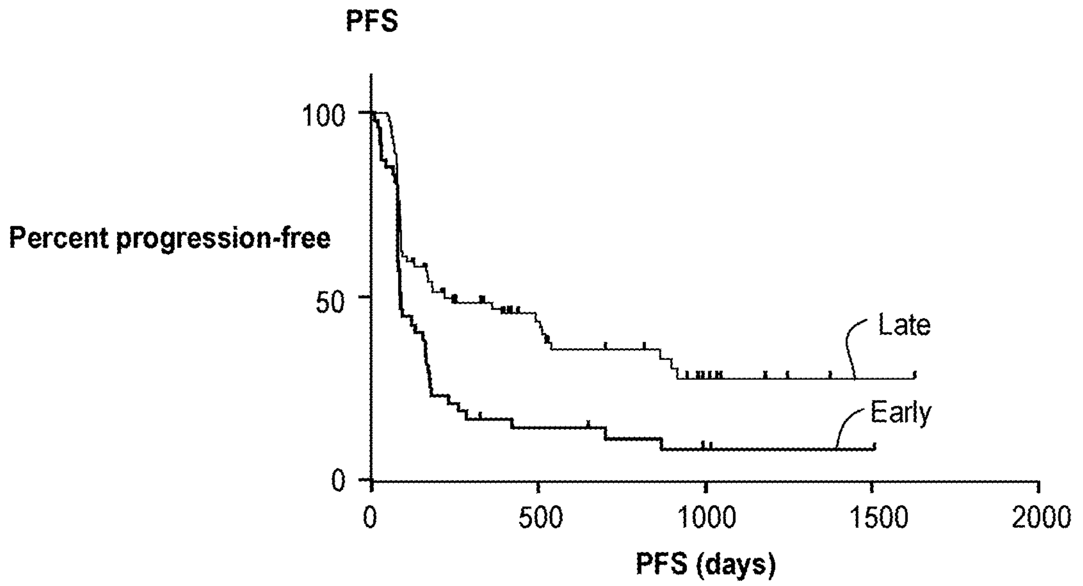

We identify several different methods for determining whether a patient is in a poor prognosis subgroup. These methods include testing in accordance with the Example 1 "IS2" classifier (BDX008) of our prior application Ser. No. 15/207,825 filed Jul. 12, 2016. A class label of Early or the equivalent produced by that test indicates the patient is likely to have a poor prognosis and obtain relatively less benefit from immunotherapy drugs.

Alternatively, the test known as VeriStrat® and described in the U.S. Pat. No. 7,736,905, which is incorporated by reference herein, can be used to identify such poor prognosis patients. This test again uses mass spectral data from a blood-based sample with a classifier trained on NSCLC patient samples treated with an EGFR-inhibitor. The test uses a k-nearest neighbor classifier to compare features from the test spectrum and a feature table from the reference set of class labeled mass spectra from a multitude of NSCLC cancer patients treated with an EGFR-inhibitor (erlotinib) and identifies the spectrum as either Poor or Good. The class label Poor or the equivalent is associated with poor prognosis and unlikely to obtain benefit from treatment from EGFR-inhibitor drugs.

Later in this disclosure we identify a still further method for identifying patients with poor prognosis, using a classifier we have termed the "NSCLC classifier." This classifier is developed from blood-based samples of NSCLC patients in advance of treatment with nivolumab.

Additionally, we have used Gene Set Enrichment Analysis (GSEA) methods to establish correlations between test classifications and biological processes which lead to possible biological mechanisms related to good and poor responses to immunotherapies. Basically, all three of these tests have a particular characteristic that there remains a small proportion of patients in the poor prognosis groups (BDX008−, VeriStrat Poor, or NSCLC classifier Early) who have a durable benefit from immunotherapy treatment. We have determined from GSEA (a technique which is also described in our prior '825 application, and in the scientific literature, see Mootha, et al., *PGC-1α-responsive genes involved in oxidative phosphorylation are coordinately downregulated in human diabetes*. Nat Genet. 2003; 34(3): 267-73 and Subramanian, et al., *Gene set enrichment analysis: A knowledge-based approach for interpreting genome-wide expression profiles*. Proc Natl Acad Sci USA 2005; 102(43): 15545-50, the content of which are incorporated by reference herein) that these patients typically have high complement activation and high levels of acute phase reactants, so they get put firmly in our poor prognosis groups. Yet, despite these characteristics of general poor prognosis, they get durable benefit from therapy. So any test we build that is associated with complement, acute response or inflammation is very likely to identify these patients into the poor prognosis group and we would expect that the new classifiers of this disclosure (identified as New classifier 1 and New classifier 2) would be able to identify them as likely to do better than other patients in these poor prognosis groups.

One of the goals of this document is to describe tests (classification exercises making use of mass spectral data from a blood-based sample and a programmed computer implementing a classifier) which are capable of the further step of identifying patients which obtain durable benefit from immunotherapy drugs despite being classified or identified in a poor prognosis subgroup, e.g., VeriStrat Poor, BDX008− or IS2 Early, or NSCLC classifier Early, or otherwise. These classifiers, identified as New classifier 1 and New classifier 2, and associated tests are described in further detail in the discussion which follows. The performance of these tests is described below and in conjunction with the appended figures. We further describe the insights and discoveries we have made regarding the biological functions of such patients with durable responses to immunotherapy, see Appendix B of our prior provisional application.

Furthermore, in our work with the new NSCLC classifier, in the second line advanced lung cancer setting, we were able to identify subgroups of patients, by combination of VeriStrat (test described in U.S. Pat. No. 7,736,905) or a new lung cancer immunotherapy test ("NSCLC classifier") with "New classifier 2," that had especially poor outcomes when treated with nivolumab. Within these subgroups, outcomes on nivolumab did not show any superiority and be slightly inferior to standard docetaxel chemotherapy. This indicates the potential of the application of New classifier 2 in combination with the "NSCLC classifier" or VeriStrat to identify patients likely to have better or similar outcomes on docetaxel rather than a checkpoint inhibitor in second line treatment of NSCLC.

In one embodiment, a method for identifying a cancer patient likely to have durable benefit from an immunotherapy drug is disclosed. The method includes the steps of:

a. conducting a test on a blood-based sample of the cancer patient that identifies the patient as being in a class of patients determined to be a poor prognosis subgroup, and
b. classifying mass spectral data obtained from the blood-based sample with a classifier which produces a class label of Late or the equivalent which identifies the patient as likely to have durable benefit from the immunotherapy drug.

In one possible embodiment, the cancer patient has lung cancer, renal cell carcinoma, or melanoma. In one embodiment the drug takes the form of an antibody drug blocking ligand activation of the PD-1 checkpoint protein, anti-CTLA4 drugs, high dose interleukin-2, and combination therapies. The immunotherapy drug can take the form of a combination of two immunotherapy drugs.

In another aspect, we have disclosed a computer configured as a classifier generated from mass spectrometry data of blood-based samples obtained from a subset of cancer patients who are determined to be in a poor performing subgroup, wherein the classifier generates a class label from mass spectrometry data obtained from a blood-based sample that identifies a patient has likely to have a durable response on an immunotherapy drug. Again, the immunotherapy drug can take the form of an antibody drug blocking ligand activation of the PD-1 checkpoint protein, anti-CTLA4 drugs, high dose interleukin-2, and combination therapies. The immunotherapy drug can also take the form of a combination of two immunotherapy drugs.

Figure 17:
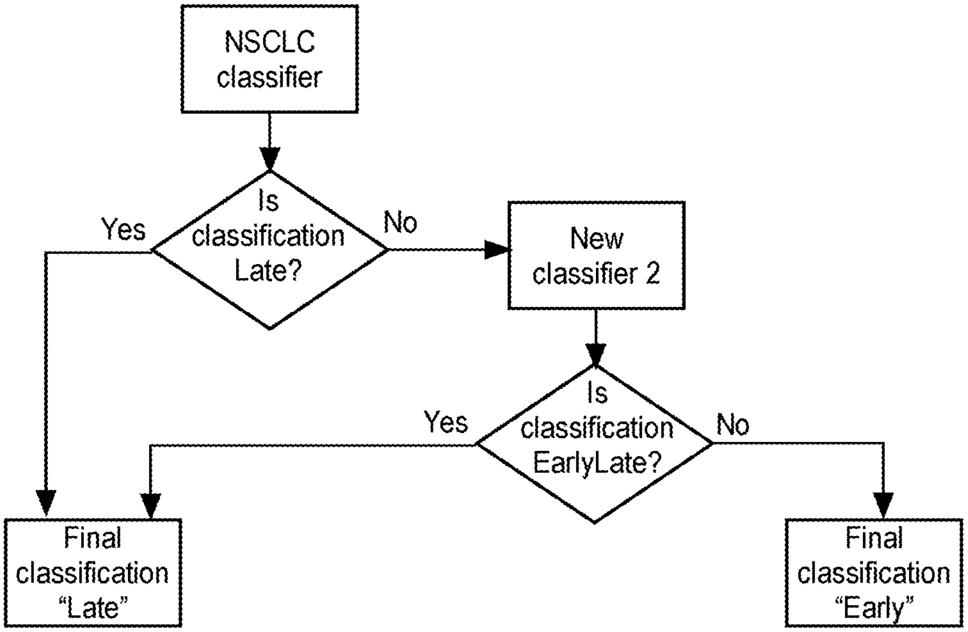
FIG. 17 is a schema of a hierarchical classification schema including a new classifier "NSCLC (non-small cell lung cancer) classifier" which identifies patients in good and poor prognosis subgroups (Late and Early, respectively), and a new classifier 2 which identifies patients in the Early subgroup which have durable response to immunotherapy, class label EarlyLate.
Figure 18A:
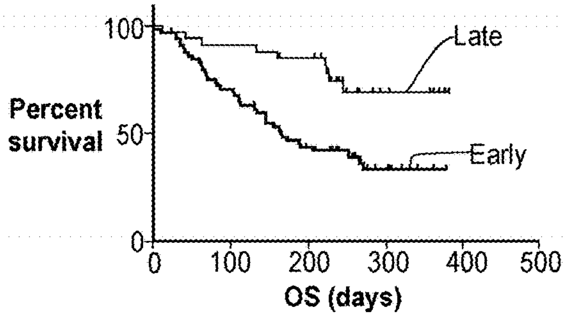
FIGS. 18A-18D are Kaplan-Meier plots split by classification group ("NSCLC classifier"—18A and 18C—and combination of "NSCLC classifier" with "New classifier 2"—18B and 18D) for the "nivolumab lung" cohort.
Figure 18B:
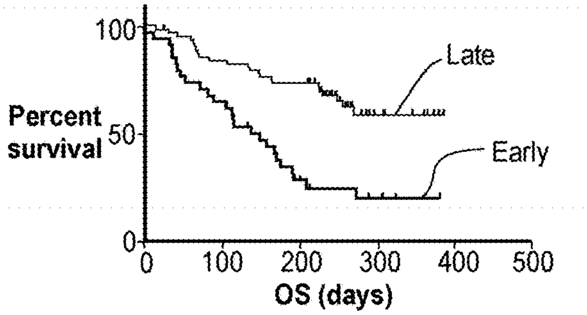
Figure 18C:
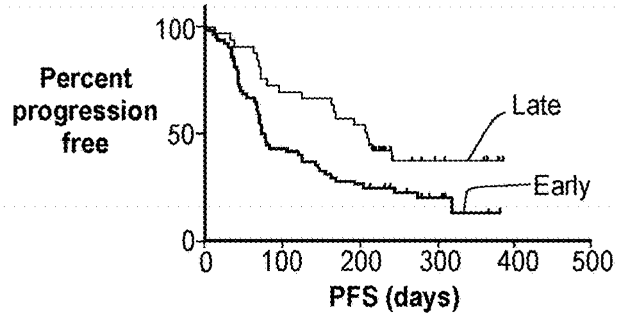
Figure 18D:
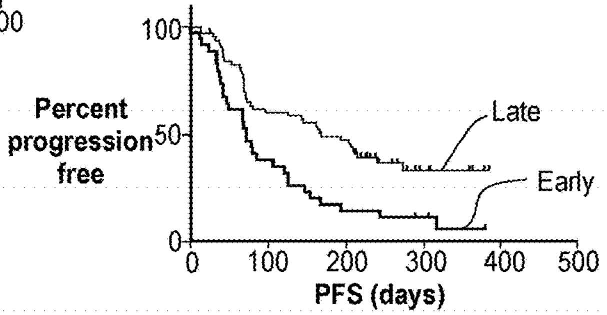
Figure 19A:
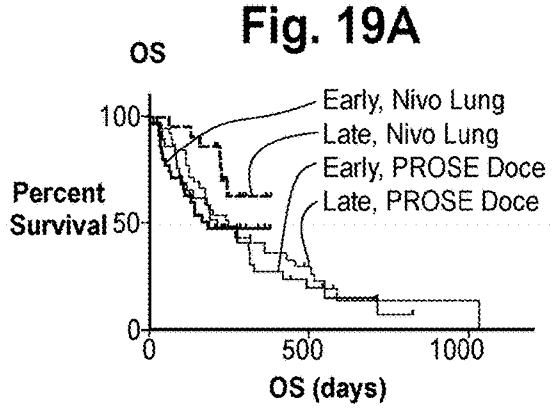
FIGS. 19A-19D are Kaplan-Meier plots showing the subgroups defined by the NSCLC classifier (FIGS. 19A and 19C) and the combination of the NSCLC classifier with New classifier 2 (FIGS. 19B and 19D) for patients in second line of treatment within the nivolumab cohort compared with patients treated with docetaxel in the PROSE study.
Figure 19B:
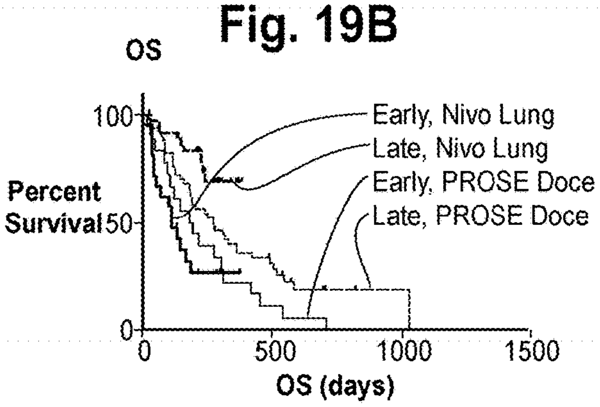
Figure 19C:
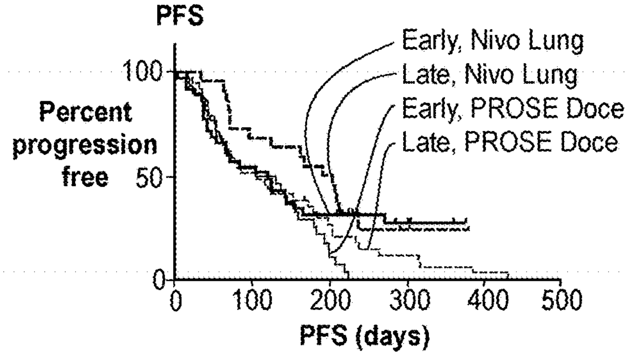
Figure 19D:
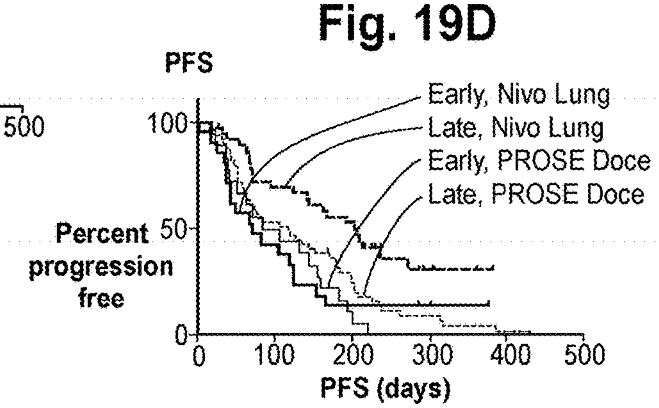
Figure 20A:
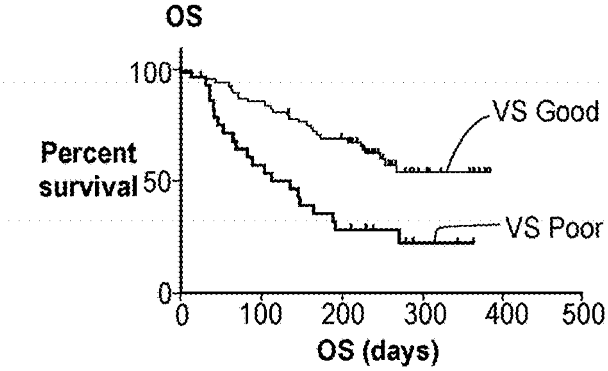
FIGS. 20A-20D are Kaplan-Meier plots split by classification group VeriStrat (20A and 20C) and combination of VeriStrat with "New classifier 2" (20B and 20D) for the nivolumab lung cohort.
Figure 20B:
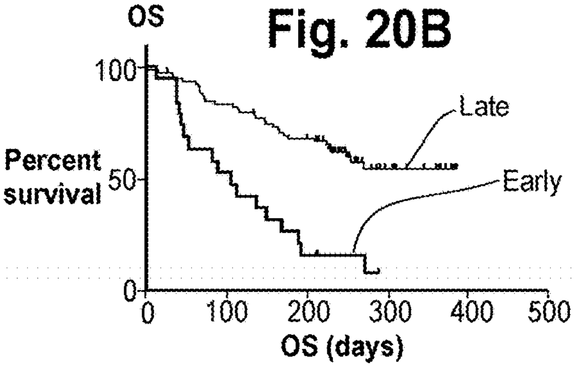
Figure 20C:
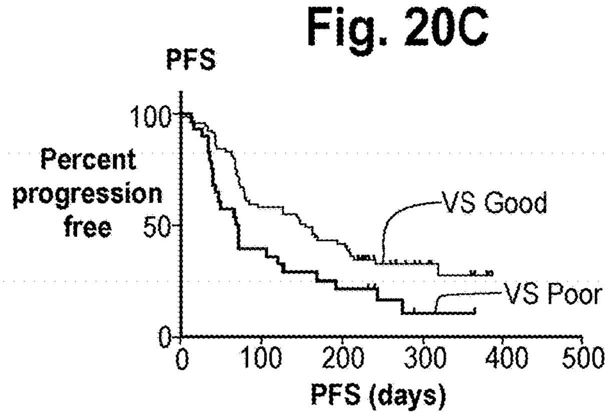
Figure 20D:
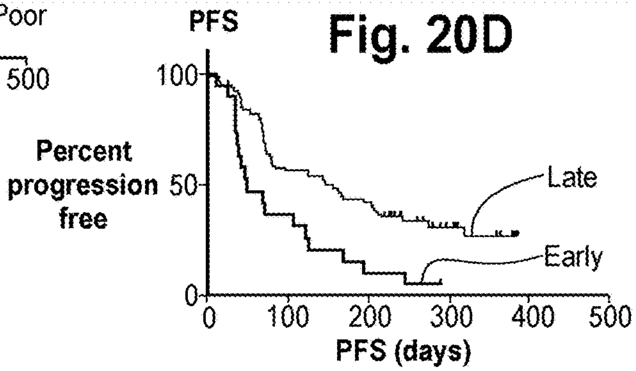
Figure 21A:
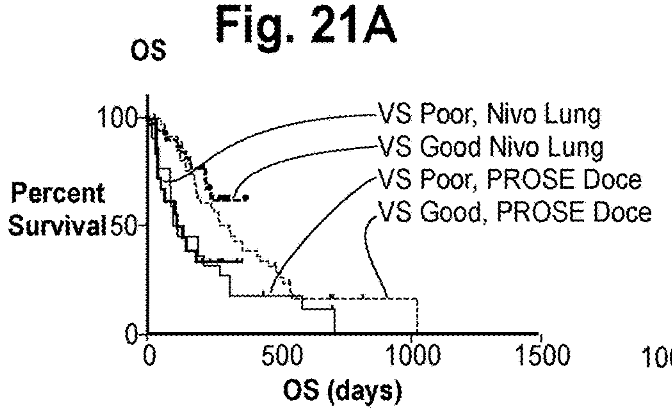
FIGS. 21A-21D are Kaplan-Meier plots showing the subgroups defined by the VeriStrat test (21A and 21C) and by the combination of the VeriStrat with New classifier 2 (21B and 21D) for patients in second line of treatment within the nivolumab cohort compared with patients treated with docetaxel in the PROSE study.
Figure 21B:
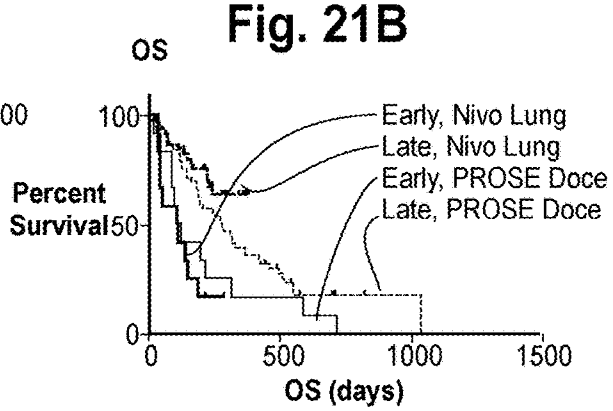
Figure 21C:
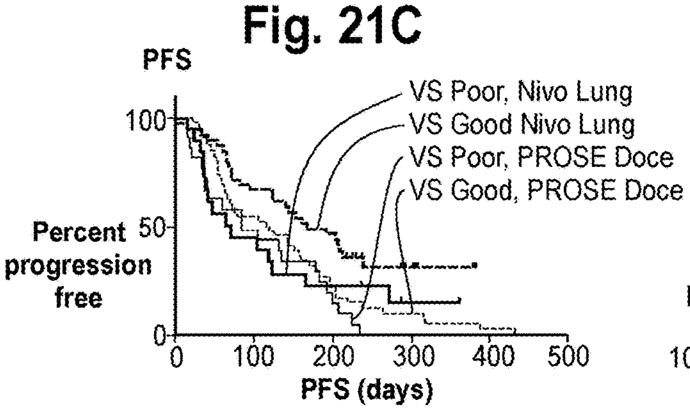
Figure 21D:
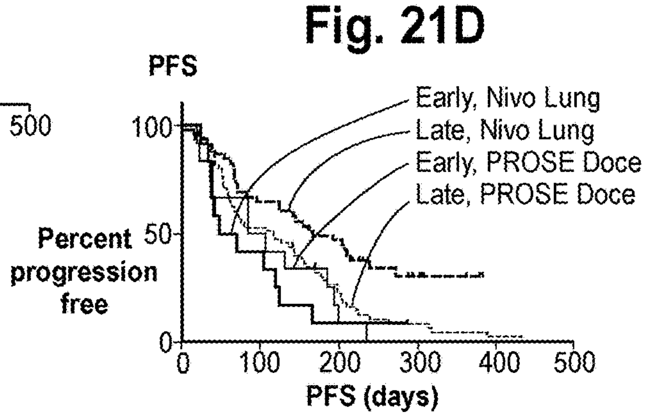
Figure 22:
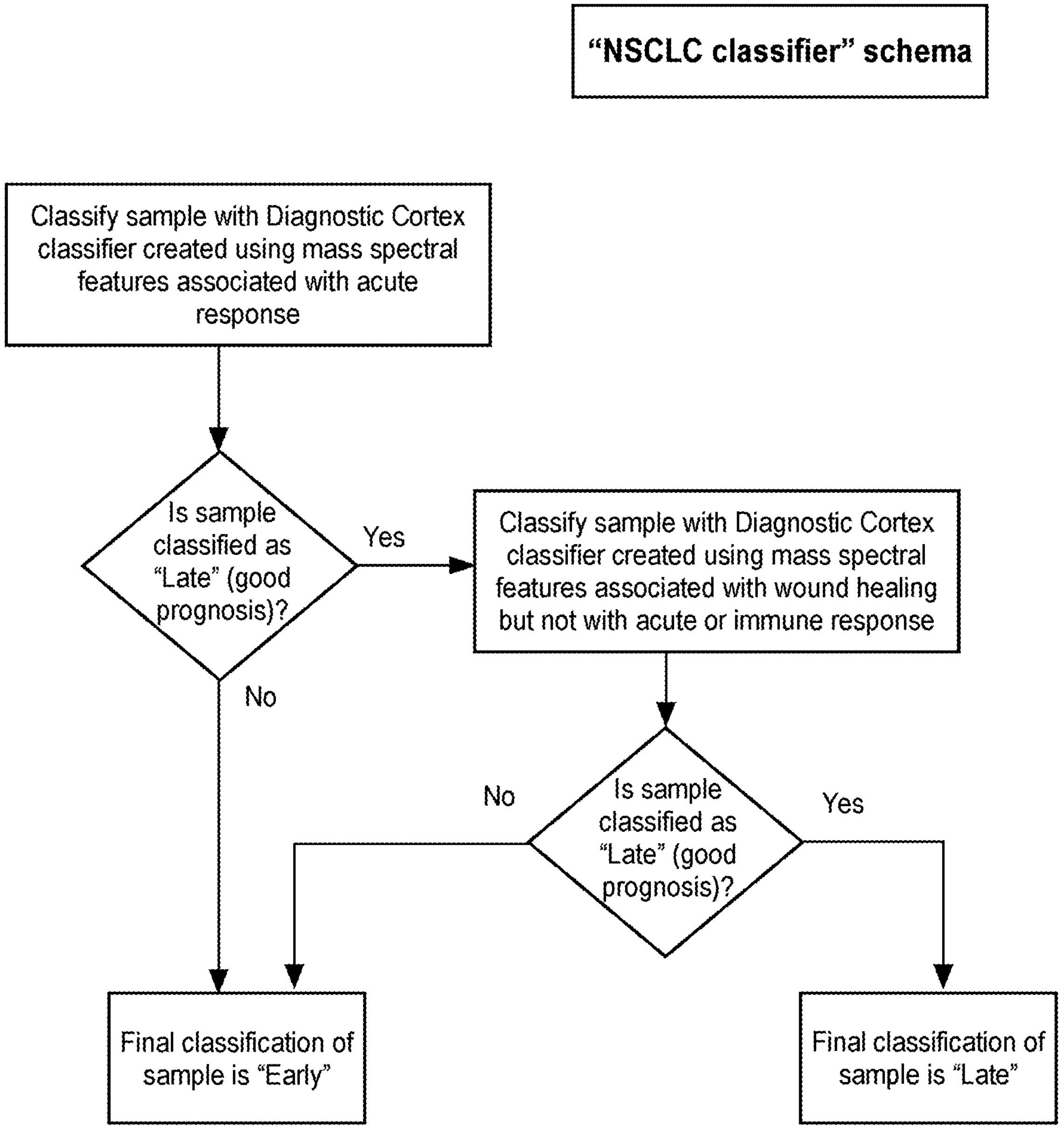
FIG. 22 is a schema of the "NSCLC classifier" of FIG. 17.

In another aspect, a method for classifying mass spectral data from a blood-based sample from a cancer patient with a computer configured as a classifier is described. The method includes the steps of:

a) classifying the sample with a first stage classifier, the first stage classifier identifying whether the patient is a member of a subgroup of patients having a poor prognosis, (see e.g., FIG. 5) and, if so,
b) classifying the sample with a second stage classifier (New classifier 1, or new classifier 2 of FIG. 5) which generates a class label of Early or the equivalent or Late or the equivalent, wherein a class label of Late or the equivalent indicates the patient is likely to obtain durable benefit from immunotherapy drugs. In this embodiment, the first stage classifier BDX008, VeriStrat, or the "NSCLC classifier" (FIGS. 17 and 22). The second stage classifier can take the form of either New classifier 1 or New classifier 2 as described below. In this method the patient can be a NSCLC patient, a renal cell carcinoma patient or a melanoma patient. The drug can take the form of an antibody drug blocking ligand activation of the PD-1 checkpoint protein, anti-CTLA4 drugs, high dose interleukin-2, and combination therapies. The immunotherapy drug can take the form of a combination of two immunotherapy drugs.

In still another configuration, the invention can take the form of a computer configured with a memory storing a reference set of mass spectral data and program code implementing a classification procedure in accordance with either New classifier 1 or New classifier 2 or the "NSCLC classifier", FIGS. 17 and 22. In the above configuration the reference set of mass spectral data includes feature values of the features listed in table 25.

In still another possible configuration, a laboratory test center is described which includes a mass spectrometer. e.g., MALDI TOF mass spectrometer, and a computer as recited in the previous paragraph.

In still another possible configuration, as described below in FIG. 22, the invention can take the form of a lung cancer classifier including a first classifier trained with mass spectrometry features associated with an acute response biological function, and a second classifier trained on mass spectrometry features associated with a wound healing function but not acute response or immune response biological functions, and wherein the mass spectrometry features are obtained from a mass spectrometry performed on a blood based samples from a set of lung cancer patients subsequently treated with an immunotherapy drug.

Another embodiment of the invention is directed to a method for guiding treatment of cancer patients. The method includes a step of using a computer configured as New classifier 1 or New classifier 2, in combination with a first classifier identifying patients in a poor prognosis subgroup, to identify patients which are unlikely to benefit much if any from immunotherapy, including immune checkpoint inhibitors, but who might do as well or possibly better on standard chemotherapy such as docetaxel.

Samples

The samples available for this study belong to 5 different sample cohorts:

"Moffitt": 119 samples taken before nivolumab treatment from patients with unresectable melanoma and used for the development of the BDX008 test. Forty-seven of these samples had been classified as BDX008− and seventy two as BDX008+. Baseline clinical characteristics and further details of this cohort can be found in our prior patent application Ser. No. 15/207,825 filed Jul. 12, 2016, Example 1.

"Yale Nivo": 30 pre-treatment samples from patients with advanced unresectable melanoma treated with anti-PD-1 antibodies at Yale University. Ten of these samples had been classified as BDX008− and 20 as BDX008+. Baseline clinical characteristics and further details of this cohort can be found in our prior patent application Ser. No. 15/207,825 filed Jul. 12, 2016, pages 79-80.

"Yale Ipi": 48 pre-treatment samples from patients with advanced unresectable melanoma treated with anti-CTLA4 antibodies at the Yale University. Twenty of these samples had been classified as BDX008− and 28 as BDX008+. Baseline clinical characteristics and further details of this set can be found in prior patent application Ser. No. 15/207,825 filed Jul. 12, 2016, pages 80-81.

"IL2 MGH": 112 samples from melanoma patients collected prior to IL2 (interleukin-2) therapy in the SELECT trial. Twenty-three of these samples had been classified as BDX008− and 89 as BDX008+. The sample cohort did not have baseline clinical data available.

"IL2 Curti": 37 samples from melanoma patients. Eleven of these patients had been classified as BDX008− and 26 as BDX008+.

A sixth set of samples, referred to as "the nivolumab lung" cohort, was used in development of the "NSCLC classifier" described later on. The five sample sets listed above were used to develop New classifiers 1 and 2.

The present document used the samples that had been classified as BDX008− from all the 5 aforementioned sample sets for classifier development. Samples with OS greater or equal to 100 weeks or PFS greater or equal to 75 weeks were assigned a training class label of "EarlyLate" and all other samples were assigned the training label of "EarlyEarly". Table 1 details the number of training samples belonging to each class by sample set.

TABLE 1

Number of samples in each training class by cohort

| Sample set | # of samples with training class label EarlyLate | # of samples with training class label EarlyEarly |
|---|---|---|
| Moffitt | 8 | 39 |
| Yale Nivo | 1 | 9 |
| Yale Ipi | 3 | 17 |
| IL2 MGH | 5 | 18 |
| IL2 Curti | 2 | 9 |
| Total | 19 | 92 |

The mass spectra used for test development had already been generated in prior studies of each of the five sample cohorts. The details of sample preparation and spectral acquisition are repeated here for completeness. Spectral processing was performed using parameters previously designed for a prior investigation, and full details are provided below.

Sample Preparation

Samples were thawed and 3 μl aliquots of each test sample (from patients treated with immunotherapy) and quality control serum (a pooled sample obtained from serum of five healthy patients, purchased from ProMedDx, "SerumP3") spotted onto VeriStrat serum cards (Therapak). The cards were allowed to dry for 1 hour at ambient temperature after which the whole serum spot was punched out with a 6 mm skin biopsy punch (Acuderm). Each punch was placed in a centrifugal filter with 0.45 μm nylon membrane (VWR). One hundred μl of HPLC grade water (JT Baker) was added to the centrifugal filter containing the punch. The punches were vortexed gently for 10 minutes then spun down at 14,000 rcf for two minutes. The flow-through was removed and transferred back on to the punch for a second round of extraction. For the second round of extraction, the punches were vortexed gently for three minutes then spun down at 14,000 rcf for two minutes. Twenty microliters of the filtrate from each sample was then transferred to a 0.5 ml eppendorf tube for MALDI analysis.

All subsequent sample preparation steps were carried out in a custom designed humidity and temperature control chamber (Coy Laboratory). The temperature was set to 30° C. and the relative humidity at 10%.

An equal volume of freshly prepared matrix (25 mg of sinapinic acid per 1 ml of 50% acetonitrile:50% water plus 0.1% TFA) was added to each 20 μl serum extract and the mix vortexed for 30 sec. The first three aliquots (3×2 μl) of sample:matrix mix were discarded into the tube cap. Eight aliquots of 2 μl sample:matrix mix were then spotted onto a stainless steel MALDI target plate (SimulTOF). The MALDI target was allowed to dry in the chamber before placement in the MALDI mass spectrometer.

QC samples were added to the beginning (two preparations) and end (two preparations) of each batch run.

Spectral Acquisition

The mass spectral data acquisition and processing described below makes use of the features of the method we refer to as DEEP MALDI, described in prior U.S. Pat. No. 9,279,798 assigned to Biodesix, Inc., the content of which is incorporated by reference herein.

MALDI (matrix-assisted laser desorption and ionization) spectra were obtained using a MALDI-TOF mass spectrometer (SimulTOF 100 s/n: LinearBipolar 11.1024.01 from Virgin Instruments, Sudbury, MA, USA). The instrument was set to operate in positive ion mode, with ions generated using a 349 nm, diode-pumped, frequency-tripled Nd:YLF laser operated at a laser repetition rate of 0.5 kHz. External calibration was performed using a mixture of standard proteins (Bruker Daltonics, Germany) consisting of insulin (m/z 5734.51 Da), ubiquitin (m/z, 8565.76 Da), cytochrome C (m/z 12360.97 Da), and myoglobin (m/z 16952.30 Da).

Spectra from each MALDI spot were collected as 800 shot spectra that were 'hardware averaged' as the laser fires continuously across the spot while the stage is moving at a speed of 0.25 mm/sec. A minimum intensity threshold of 0.01 V was used to discard any 'flat line' spectra. All 800 shot spectra with intensity above this threshold were acquired without any further processing.

Spectral Processing

Raster Spectra Preprocessing

Alignment and Filtering

Each raster spectrum of 800 shots was processed through an alignment workflow to align prominent peaks to a set of 43 alignment points (see table 2). A filter was applied to each spectrum that essentially smooths noise followed by background subtraction in preparation for peak identification. Given the identified peaks, the filtered spectra (without background subtraction) were aligned. Additional filtering parameters required that raster spectra have at least 20 peaks and at least 5 alignment points are used to be included in the pool of rasters used to assemble the average spectrum.

TABLE 2

| Alignment points used to align the raster spectra |
|---|
| m/z |
| 3168.00 |
| 4153.48 |
| 4183.00 |
| 4792.00 |
| 5773.00 |
| 5802.00 |
| 6432.79 |
| 6631.06 |
| 7202.00 |
| 7563.00 |
| 7614.00 |
| 7934.00 |
| 8034.00 |
| 8206.35 |
| 8684.25 |
| 8812.00 |
| 8919.00 |
| 8994.00 |
| 9133.25 |
| 9310.00 |
| 9427.00 |
| 10739.00 |
| 10938.00 |
| 11527.06 |
| 12173.00 |
| 12572.38 |
| 12864.24 |
| 13555.00 |
| 13762.87 |
| 13881.55 |
| 14039.60 |
| 14405.00 |
| 15127.49 |
| 15263.00 |
| 15869.06 |
| 17253.06 |
| 18629.76 |
| 21065.65 |
| 23024.00 |
| 28090.00 |
| 28298.00 |

Raster Averaging

Averages were created from the pool of aligned and filtered raster spectra. A random selection of 500 raster spectra was averaged to create a final analysis spectrum for each sample of 400,000 shots.

Deep MALDI Average Spectra Preprocessing

Background Estimation and Subtraction

The two window method of background estimation and subtraction was used to control for background in regions where small peaks are surrounded by much larger peaks. Table 3 lists the windows that were used for estimation and subtraction of background from the analysis spectra (averages).

TABLE 3

| Background estimation windows | |
|---|---|
| m/z | width |
| Wide windows | |
| 3000 | 80000 |
| 30000 | 80000 |
| 31000 | 160000 |

TABLE 3-continued

| Background estimation windows | |
|---|---|
| m/z | width |
| Medium windows | |
| 3000 | 5000 |
| 30000 | 5000 |
| 31000 | 10000 |

Normalization by Bin Method

Initial normalization uses relatively wide regions of the spectra for normalization. The spectral intensity is integrated across these regions and summed together to create a normalization coefficient. This is done separately for each spectrum. Each spectrum is then scaled by dividing the spectral intensity at each m/z value by the normalization coefficient for the spectrum. A total of 16 bins (spectral regions) had already been identified for use as the normalization windows. These are listed in table 4.

TABLE 4

| Iteration1 normalization bins | |
|---|---|
| Left m/z | Right m/z |
| 3530.679 | 3784.658 |
| 3785.029 | 4078.739 |
| 4220.21 | 4323.065 |
| 4875.581 | 4943.903 |
| 5260.635 | 5435.524 |
| 5436.47 | 5682.433 |
| 6050.421 | 6376.807 |
| 6510.852 | 6601.081 |
| 7751.414 | 7898.826 |
| 10606.12 | 10897.2 |
| 10908.61 | 11356.51 |
| 12425.27 | 12527.26 |
| 17710.35 | 18504.69 |
| 19212.92 | 20743.82 |
| 22108.95 | 22959.15 |
| 23738.5 | 24739.04 |

A second iteration of normalization by bin had been previously specified. These normalization bins are listed in table 5. The spectra were normalized again in the same way explained above using these normalization bins (windows).

TABLE 5

| iteration2 normalization | |
|---|---|
| Left m/z | Right m/z |
| 4168.226 | 4219.839 |
| 4875.581 | 4943.903 |
| 4946.131 | 5077.576 |
| 5080.918 | 5259.892 |
| 5260.635 | 5435.524 |
| 6510.852 | 6601.081 |
| 7751.414 | 7898.826 |
| 10606.12 | 10897.2 |
| 10908.61 | 11356.51 |

Average Spectra Alignment

The peak alignment of the average spectra is typically very good; however, a fine-tune alignment step was performed to address minor differences in peak positions in the spectra. A set of peaks typically found in human serum were used as alignment points and applied to the analysis spectra (table 6) with a calibration tolerance of 1200 ppm.

TABLE 6

| Calibration points used to align the spectral averages |
|---|
| m/z |
| 3315 |
| 4153 |
| 4457 |
| 4710 |
| 5066 |
| 6433 |
| 6631 |
| 7934 |
| 8916 |
| 9423 |
| 9714 |
| 12868 |
| 13766 |
| 14045 |
| 14093 |
| 15131 |
| 15872 |
| 16078 |
| 17256 |
| 17383 |
| 18631 |
| 21069 |
| 21168 |
| 28084 |
| 28293 |
| 67150 |

Feature Definitions

Figure 2:
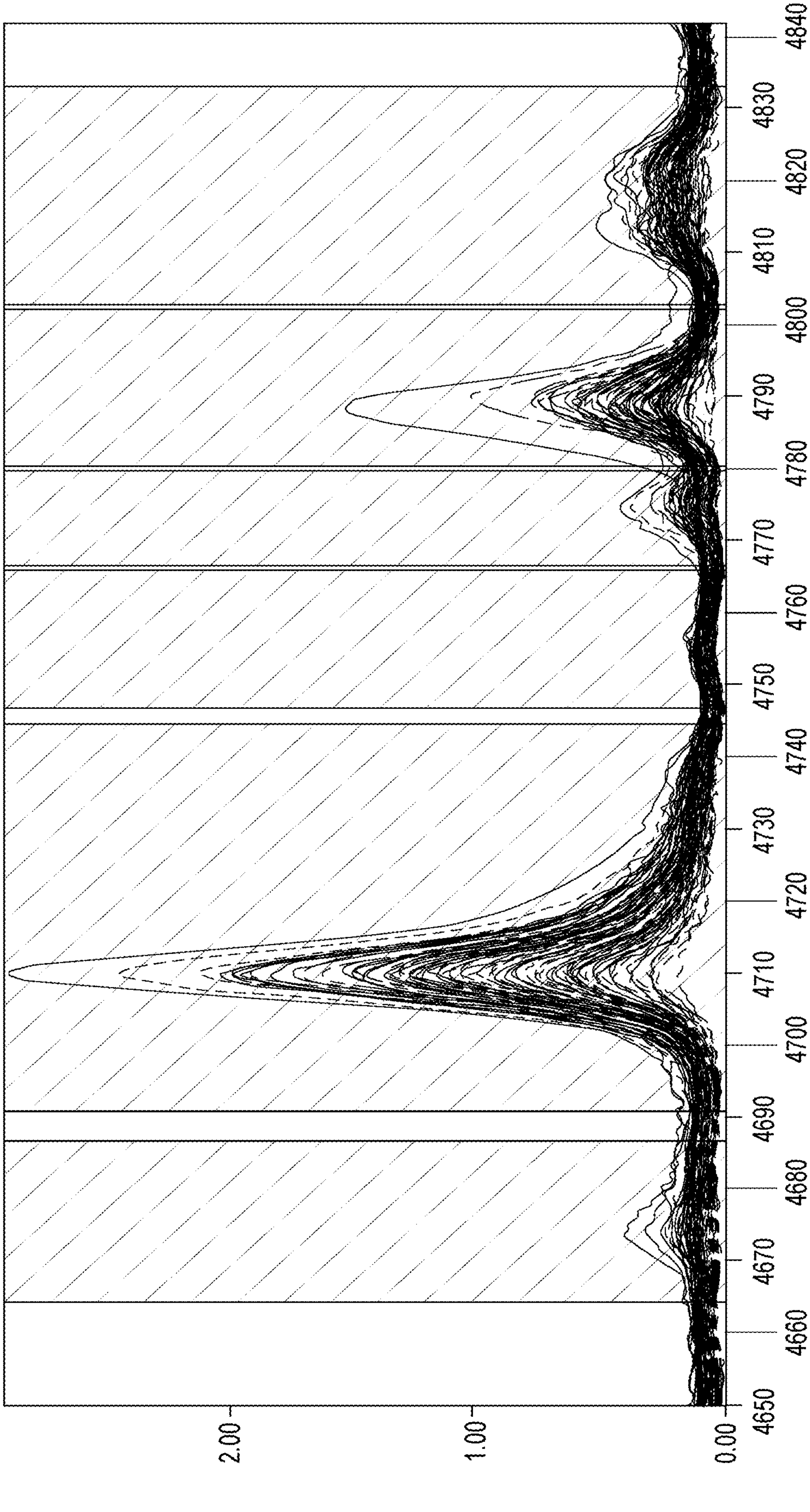
FIG. 2 is plot of a portion of a mass spectrum illustrating how features are defined. Each separate hatched region represents one feature. The y scale shows normalized intensity and the x axis shows m/z.

Feature definitions are regions of spectra of interest (peaks) defined by a left and right mass/charge (m/z) boundary. Feature values are computed as the sum of the area between the boundaries (integration of the peak signal) and are computed for each feature and spectrum independently. A set of 298 features had already been defined in a previous project. FIG. 2 is an example plot illustrating how the features are defined. Each separate hatched region represents one feature. The y scale shows the normalized intensity and the x axis shows m/z.

The full list of feature definitions we used for classifier training can be found in Table 25.

Batch Correction of Analysis Spectra

SerumP3 Analysis

Two preparations of the reference sample, SerumP3, were plated at the beginning (1,2) and end (3,4) of each batch of samples run. The purpose of these samples is to ensure that variations by batch due to slight changes in instrument performance (for example, aging of the detector) can be corrected for.

To perform batch correction, one spectrum, which is an average of one of the preparations from the beginning and one from the end of the batch, must serve as the reference for the batch. The procedure used for selecting the pair is described first.

The reference samples were preprocessed as described above. All 298 features were used to evaluate the possible combinations (1-3, 1-4, 2-3, 2-4). We compared each possible combination of replicates using the function:

$$A=\min(\mathrm{abs}(1-\mathrm{ftrval1}/\mathrm{ftrval2}),\mathrm{abs}(1-\mathrm{ftrval2}/\mathrm{ftrval1}))$$

where ftrval1 (ftrval2) is the value of a feature for the first (second) replicate of the replicate pair. This quantity A gives a measure of how similar the replicates of the pair are. For each feature, A is reported. If the value is >0.5, then the feature is determined to be discordant, or 'Bad'. A tally of the bad features is reported for each possible combination. If the value of A is <0.1, then the feature is determined to be concordant and reported as 'Good'. A tally of the Good features is reported for each possible combination. Using the tallies of Bad and Good features from each possible combination, we computed the ratio of Bad/Good. The combination with the lowest ratio was reported as the most similar combination, unlikely to contain any systematic or localized outlier behavior in either of the reference spectra. If no ratio can be found that is less than 0.12, then the batch is declared a failure.

Batch Correction

A gold standard reference spectrum for batch correction had been established for this spectral processing workflow. All batches of spectra used in development of the current test were batch corrected to this gold standard using the following approach.

Within each batch $j(2 \le j \le N_{batches})$, the ratio $$\hat{r}_i^j = \frac{A_i^j}{A_i^1}$$

and the average amplitude $$\overline{A}_i^j = \frac{1}{2}\left(A_i^j + A_i^1\right)$$

are defined for each $i^{th}$ feature centered at $(m/z)_i$, where $$A_i^j$$

is the average reference spectra amplitude of feature i in the batch being corrected and $$A_i^1$$

is the reference spectra amplitude of feature i in batch 1 (the reference standard). It is assumed that the ratio of amplitudes between two batches follows the dependence $$r(\overline{A},(m/z))=(a_0+a_1\ln(\overline{A}))+(b_0+b_1\ln(\overline{A}))(m/z)+c_0(m/z)^2.$$

On a batch to batch basis, a continuous fit is constructed by minimizing the sum of the square residuals, $$\Delta^j = \sum_i \left(\hat{r}_i^j - r^j(a_0, a_1, b_0, b_1, c_0)\right)^2$$

and using the experimental data of the reference sample. The SerumP3 reference samples are used to calculate the correction function. Steps were taken to not include outlier points in order to avoid bias in the parameter estimates. The values of the coefficients $a_0$, $a_1$, $b_0$, $b_1$ and $c_0$, obtained for the different batches are omitted for the sake of brevity.

Once the final fit, $r^j(\overline{A}, (m/z))$, is determined for each batch, the next step is to correct, for all the samples, all the features (with amplitude A at (m/z)) according to $$A_{corr} = \frac{A}{r^j(\overline{A}, (m/z))}.$$

After this correction, the corrected $$(\overline{A}_i^j, (m/z)_i, \hat{r}_i^j)$$

feature values calculated for reference spectra lie around the horizontal line defined by r=1.

Partial Ion Current (PIC) Normalization

A set of 10 features were used to normalize the final table to be used in the diagnostic cortex classifier development procedure of FIG. 3 (Table 7).

TABLE 7

| Features used for PIC normalization |
| --- |
| Feature m/z |
| 3553 |
| 3907 |
| 3952 |
| 4010 |
| 6194 |
| 7472 |
| 7789 |
| 7827 |
| 11152 |
| 12290 |

To normalize, the feature values from the listed features were summed for each spectrum to compute a normalization scalar. All feature values were then divided by the normalization scalar per sample to arrive at the final table of feature values for all spectra.

Figure 3B:
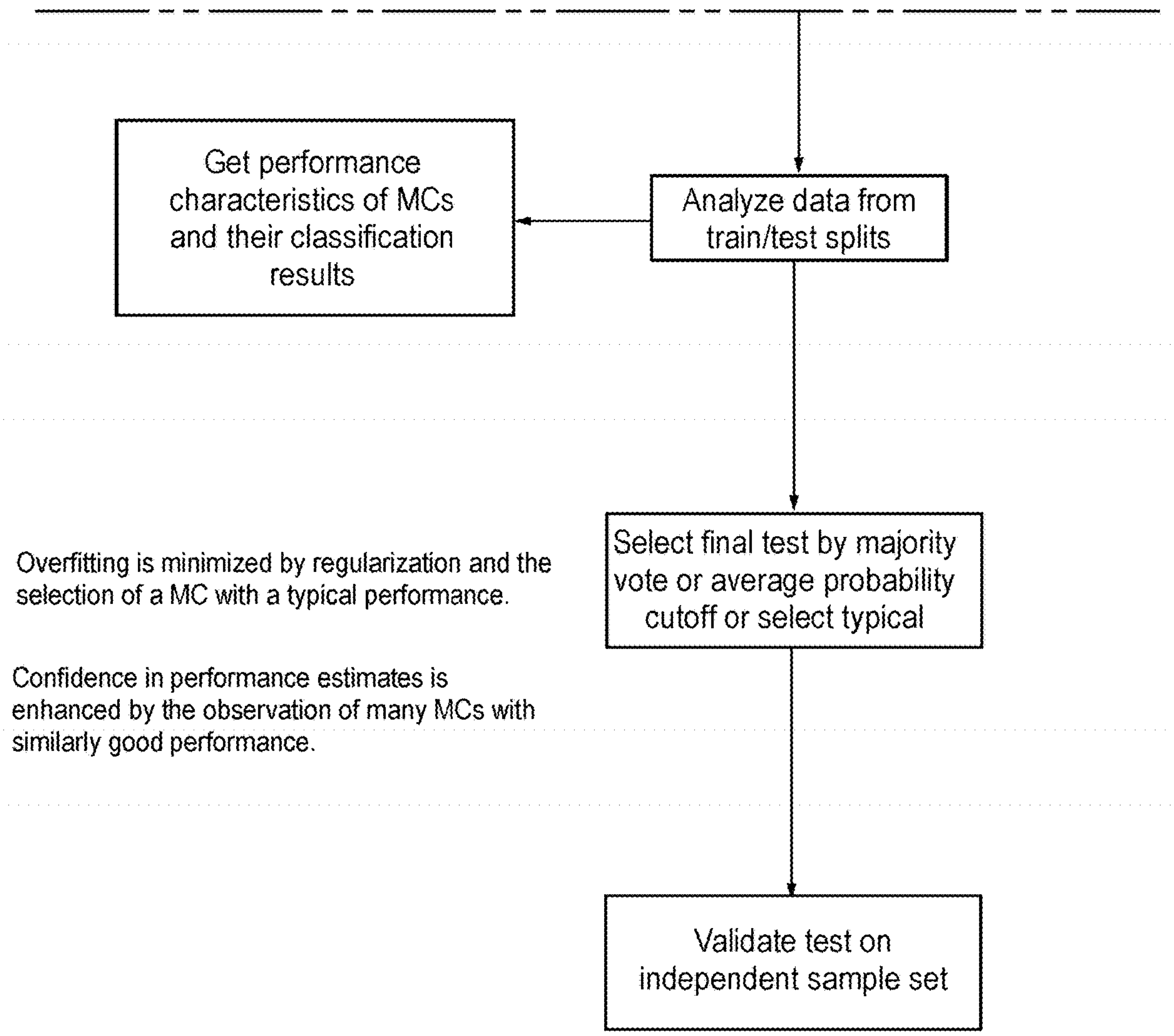
FIG. 3, consisting of FIGS. 3A and 3B, is a flow chart of a classifier development methodology we refer to herein as the "Diagnostic Cortex". The methodology is described extensively in the patent literature, particularly U.S. Pat. No. 9,477,906 to Heinrich Röder et al., assigned to Biodesix, Inc., the content of which is incorporated by reference herein. We used the procedure of FIGS. 3A-3B to develop the BDX008 classifier as well as the new classifiers of this disclosure which identify patients from poor prognosis subgroups which are likely to have durable benefit from immunotherapy.

New Classifier Development (FIGS. 3A and 3B)

The new classifier development process was carried out using the Diagnostic Cortex™ procedure shown in FIG. 3, consisting of FIGS. 3A and 3B. This procedure is described at length in the patent literature, see U.S. Pat. No. 9,477,906. See also pages 44-54 and FIG. 8A-8B of our prior patent application Ser. No. 15/207,825 filed Jul. 12, 2016, the content of which is incorporated by reference herein. An overview of the process will be described and then the specifics for the present classifier generation exercise will be described later on.

In contrast to standard applications of machine learning focusing on developing classifiers when large training data sets are available, the big data challenge, in bio-life-sciences the problem setting is different. Here we have the problem that the number (n) of available samples, arising typically from clinical studies, is often limited, and the number of attributes (measurements) (p) per sample usually exceeds the number of samples. Rather than obtaining information from many instances, in these deep data problems one attempts to gain information from a deep description of individual instances. The present methods take advantage of this insight, and are particularly useful, as here, in problems where p>>n.

The method includes a first step a) of obtaining measurement data for classification from a multitude of samples, i.e., measurement data reflecting some physical property or characteristic of the samples. The data for each of the samples consists of a multitude of feature values, and a class label. In this example, the data takes the form of mass spectrometry data, in the form of feature values (integrated peak intensity values at a multitude of m/z ranges or peaks, see Table 25) as well as a label indicating some attribute of the sample (for example, patient. Early or Late death or disease progression). In this example, the class labels were assigned by a human operator to each of the samples after investigation of the clinical data associated with the sample. The development sample set is then split into a training set and a test set and the training set is used in the following steps b), c) and d).

The method continues with a step b) of constructing a multitude of individual mini-classifiers using sets of feature values from the samples up to a pre-selected feature set size s (s=integer 1 . . . n). For example a multiple of individual mini- or atomic classifiers could be constructed using a single feature (s=1), or pairs of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measurement data values (p) in the data set, and where p is in the hundreds, thousands or even tens of thousands, s will typically be 1, or 2 or possibly 3, depending on the computing resources available. The mini-classifiers execute a supervised learning classification algorithm, such as k-nearest neighbors (kNN), in which the values for a features, pairs or triplets of features of a sample instance are compared to the values of the same feature or features in a training set and the nearest neighbors (e.g., k=9) in an s-dimensional feature space are identified and by majority vote a class label is assigned to the sample instance for each mini-classifier. In practice, there may be thousands of such mini-classifiers depending on the number of features which are used for classification.

The method continues with a filtering step c), namely testing the performance, for example the accuracy, of each of the individual mini-classifiers to correctly classify the sample, or measuring the individual mini-classifier performance by some other metric (e.g. the Hazard Ratios (HRs) obtained between groups defined by the classifications of the individual mini-classifier for the training set samples) and retaining only those mini-classifiers whose classification accuracy, predictive power, or other performance metric, exceeds a pre-defined threshold to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained. Alternative supervised classification algorithms could be used, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible kNN classifiers using feature sets up to a pre-selected size (parameter s). This gives us many "mini-classifiers": e.g. if we start with 100 features for each sample (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step c) we only use those "mini-classifiers" that pass predefined criteria. These filtering criteria are chosen dependent on the particular problem: If one has a two-class classification problem, one would select only those mini-classifiers whose classification accuracy exceeds a predefined threshold, i.e., are predictive to some reasonable degree. Even with this filtering of "mini-classifiers" we end up with many thousands of "mini-classifier" candidates with performance spanning the whole range from borderline to decent to excellent performance.

The method continues with step d) of generating a master classifier (MC) by combining the filtered mini-classifiers using a regularized combination method. In one embodiment, this regularized combination method takes the form of repeatedly conducting a logistic training of the filtered set of mini-classifiers to the class labels for the samples. This is done by randomly selecting a small fraction of the filtered mini-classifiers as a result of carrying out an extreme dropout from the filtered set of mini-classifiers (a technique referred to as drop-out regularization herein), and conducting logistical training on such selected mini-classifiers. While similar in spirit to standard classifier combination methods (see e.g. S. Tulyakov et al., Review of Classifier Combination Methods, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. This is a regularization of the problem in the spirit of dropout as used in deep learning theory. In this case, where we have many mini-classifiers and a small training set we use extreme dropout, where in excess of 99% of filtered mini-classifiers are dropped out in each iteration.

In more detail, the result of each mini-classifier is one of two values, either "Early" or "Late" in this example. We can then combine the results of the mini-classifiers by defining the probability of obtaining an "Early" label via standard logistic regression (see e.g. http://en.wikipedia.org/wiki/Logistic_regression)

$$P(\text{"Early"} \mid \text{feature for a spectrum}) = \frac{\exp\left(\sum w_{mc} I(\text{mc(feature values)})\right)\text{mini classifiers}}{\text{Normalization}} \quad \text{Eq. (1)}$$

where I(mc(feature values))=1, if the mini-classifier mc applied to the feature values of a sample returns "Early", and 0 if the mini-classifier returns "Late". The weights $w_{mc}$ for the mini-classifiers are unknown and need to be determined from a regression fit of the above formula for all samples in the training set using +1 for the left hand side of the formula for the Late-labeled samples in the training set, and 0 for the Early-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same time, we use only a few of the mini-classifiers for a regression, but repeat this process many times in generating the master classifier. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the master classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

Other methods for performing the regularized combination method in step (d) that could be used include.

- Logistic regression with a penalty function like ridge regression (based on Tikhonov regularization, Tikhonov, Andrey Nikolayevich (1943). " Об устойчивости обратных задач" [On the stability of inverse problems]. Doklady Akademii Nauk SSSR 39 (5): 195-198.)
- The Lasso method (Tibshirani, R. (1996). Regression shrinkage and selection via the lasso. J. Royal. Statist. Soc B., Vol. 58, No. 1, pages 267-288).
- Neural networks regularized by drop-out (Nitish Shrivastava. "Improving Neural Networks with Dropout", Master's Thesis, Graduate Department of Computer Science, University of Toronto), available from the website of the University of Toronto Computer Science department.
- General regularized neural networks (Girosi F. et al, Neural Computation, (7), 219 (1995)).

The above-cited publications are incorporated by reference herein. Our approach of using drop-out regularization has shown promise in avoiding over-fitting, and increasing the likelihood of generating generalizable tests, i.e. tests that can be validated in independent sample sets.

"Regularization" is a term known in the art of machine learning and statistics which generally refers to the addition of supplementary information or constraints to an underdetermined system to allow selection of one of the multiplicity of possible solutions of the underdetermined system as the unique solution of an extended system. Depending on the nature of the additional information or constraint applied to "regularize" the problem (i.e. specify which one or subset of the many possible solutions of the unregularized problem should be taken), such methods can be used to select solutions with particular desired properties (e.g. those using fewest input parameters or features) or, in the present context of classifier training from a development sample set, to help avoid overfitting and associated lack of generalization (i.e., selection of a particular solution to a problem that performs very well on training data but only performs very poorly or not all on other datasets). See e.g., https://en.wikipedia.org/wiki/Regularization_(mathematics). One example is repeatedly conducting extreme dropout of the filtered mini-classifiers with logistic regression training to classification group labels. However, as noted above, other regularization methods are considered equivalent. Indeed it has been shown analytically that dropout regularization of logistic regression training can be cast, at least approximately, as L2 (Tikhonov) regularization with a complex, sample set dependent regularization strength parameter L. (S Wager. S Wang, and P Liang, Dropout Training as Adaptive Regularization. Advances in Neural Information Processing Systems 25, pages 351-359, 2013 and D Helmbold and P Long, On the Inductive Bias of Dropout, JMLR, 16:3403-3454, 2015). In the term "regularized combination method" the "combination" simply refers to the fact that the regularization is performed over combinations of the mini-classifiers which pass filtering. Hence, the term "regularized combination method" is used to mean a regularization technique applied to combinations of the filtered set of mini-classifiers so as to avoid overfitting and domination by a particular mini-classifier.

The performance of the master classifier is then evaluated by how well it classifies the subset of samples forming the test set.

In step e), steps b)-d) are repeated in the programmed computer for different realizations of the separation of the set of samples into test and training sets, thereby generating a plurality of master classifiers, one for each realization of the separation of the set of samples into training and test sets. The performance of the classifier is evaluated for all the realizations of the separation of the development set of samples into training and test sets. If there are some samples which persistently misclassify when in the test set, the process optionally loops back and steps b), c) and d) and e) are repeated with flipped class labels for such misclassified samples.

The method continues with step f) of defining a final classifier from one or a combination of more than one of the plurality of master classifiers. In the present example, the final classifier is defined as a majority vote of all the master classifiers resulting from each separation of the sample set into training and test sets, or alternatively by an average probability cutoff. See the discussion of the ROC curves described below.

Referring now to FIG. 3, at the top of the figure, the Development Set for New classifier 1 and New classifier 2, is the set of samples from the five sample sets listed previously that all tested as BDX008− (i.e., the Early class label was generated by the IS2 classifier of Example 1 of our prior U.S. patent application Ser. No. 15/207,825.)

Definition of Class Labels (EarlyEarly and EarlyLate boxes as the top of FIG. 3.)

Only samples classified as BDX008− were used for development. As explained previously, the time-to-event data of the samples were dichotomized by assigning the class label of EarlyLate to samples with OS higher or equal to 100 weeks or PFS higher or equal to 75 weeks, and the class label of EarlyEarly to all other BDX008− samples.

Creation and Filtering of Mini-Classifiers

In the flow chart of FIG. 3 we select randomly training and test sets of the class-labeled samples in the development set. In particular, the development set samples were split into training and test sets in multiple different random realizations. One thousand two hundred twenty five realizations were used. The procedure of FIG. 3 works best when training classes have the same number of samples. Hence, the training classes were split in different ratios into training and test: 13/79 for the EarlyEarly class and 13/6 for the EarlyLate class.

In the module "Make Many kNN mini-classifiers (mC)" in FIG. 3, many k-nearest neighbor (kNN) mini-classifiers (mCs) that use the training set as their reference set and k=9 were constructed using subsets of all the available 298 features (Table 25). Subsets of single and two mass spectral (MS) features were used in the construction of the kNNs, yielding a total of 44,551 mCs created.

In the next step in the Figure, to target a final classifier that has certain performance characteristics, these mCs were filtered as follows. Each mC is applied to its training set and performance metrics are calculated from the resulting classifications of the training set. Only mCs that satisfy thresholds on these performance metrics pass filtering to be used further in the process. The mCs that fail filtering are discarded. For this project accuracy filtering was used: the accuracy of the resulting classification had to lie in the [0.7-1.0] interval.

In the next step in FIG. 3 ("Generate Master classifier (MC)"), once the filtering of the mCs was complete, the mCs were combined in one master classifier (MC) using a logistic regression trained using the training set class labels. To help avoid overfitting the regression is regularized using extreme drop out with only a small number of the mCs chosen randomly for inclusion in each of the logistic regression iterations. The number of dropout iterations was selected based on the typical number of mCs passing filtering to ensure that each mC was likely to be included within the drop out process multiple times. Ten randomly selected mCs were left in per drop out iteration, in a total of 100,000 performed drop out iterations. We calculated the weights ($w_{mc}$) for each of the mini-classifiers in accordance with the Eq. (1).

Training/Test Splits

The use of multiple training/test splits avoids selection of a single, particularly advantageous or difficult, training set for classifier creation and avoids bias in performance assessment from testing on a test set that could be especially easy or difficult to classify.

The output of the logistic regression that defines each MC is a probability of being in one of the two training classes (EarlyEarly or EarlyLate). These MC probabilities can be averaged to yield one average probability for a sample. When working with the development set, this approach is adjusted to average over MCs for which a given sample is not included in the training set ("out-of-bag" estimate). These average probabilities can be converted into a binary classification by applying a threshold (cutoff). ROC (Receiver Operating Characteristic) curves can be used to investigate the performance of the whole family of classifiers created from the procedure of FIG. 3 which are parameterized by different choices of cutoff and to help choose a cutoff suitable for the clinical question.

Results

The performance of the classifiers was assessed using ROC curves, which allow the visualization of the sensitivity and specificity obtained for different values of the cutoff applied to the average probabilities obtained for each sample. When samples were used in training, the average probability was calculated across the realizations (MCs) where the sample was in the test set (out of bag estimate). For samples never used in training, the probability was simply averaged over all realizations (MCs).

Figure 4:
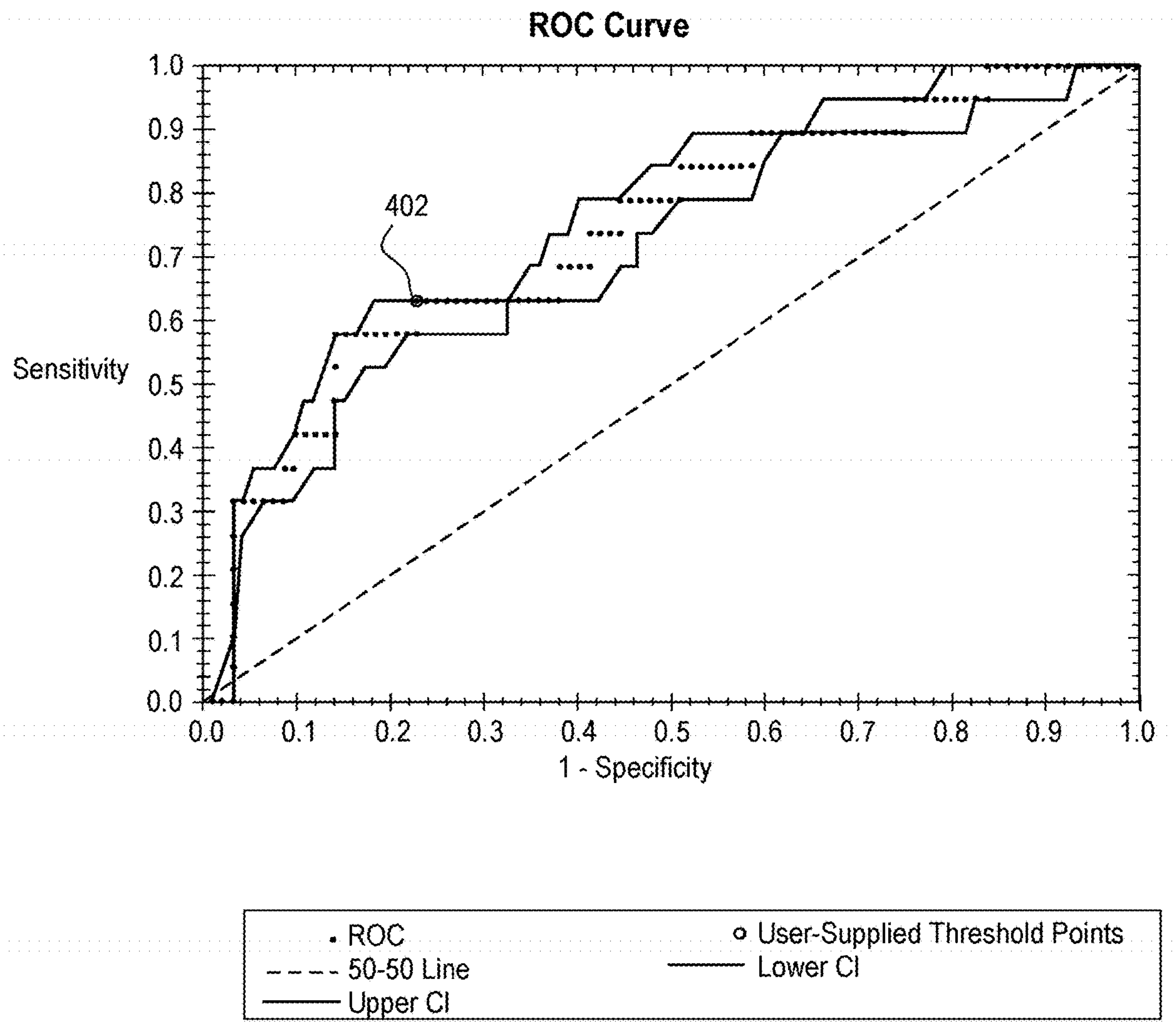
FIG. 4 is a Receiver Operating Characteristic (ROC) curve showing performance of the "New classifier 1" we developed. The upper and lower confidence interval (CI) lines in the figure should be ignored.

FIG. 4 shows the ROC curve, plotted using all 111 development set samples (classified previously as BDX008−). The corresponding area under the curve (AUC) is 0.739. The chosen cutoff to be applied to the average probabilities was set to 0.459 and is represented in the plot as reference 402. That point corresponds to a sensitivity of 63.2% and a specificity of 77.2% (assuming that the "positive" classification label, corresponding to smaller averaged probabilities, is EarlyLate). The classifier defined by the cutoff of 0.459 is referred to as "New classifier 1" in this document.

Relation of Class Labels to Protein Functional Groups

Protein Set Enrichment Analysis (PSEA), a method inspired by gene set enrichment analysis (see Example 1 and pages 126-131 of our prior application Ser. No. 15/207,825 and the literature cited therein, including the Subramanian and Mootha papers, see footnote 1), was used to look for an association of the test classifications with protein functional groups. For this an independent set of 49 samples was used where paired deep MALDI spectra and protein panel (Somalogic, Boulder, CO) results were available. Of the 49 samples 24 classified as EarlyEarly and 25 as EarlyLate according to New classifier 1.

The results for 29 different protein functional groups are shown in Table 8. P values are not corrected for multiple comparisons. At the $\alpha=0.05$ significance level, association of the test classifications was found with Immune Response Type 2. The list of proteins that comprises the functional group Immune Response Type 2 is shown in Table 9 together with the corresponding correlation coefficients between individual proteins and classification labels and the associated p-values. More details on this analysis method can be found in the patent application and literature cited above.

TABLE 8

Results of Protein Set Enrichment Analysis

| Protein Set Description | Enrichment score | p value |
|---|---|---|
| Acute inflammation | 0.277 | 0.401 |
| Innate Immune Response | 0.574 | 0.192 |
| Adaptive immune response | −0.218 | 0.939 |
| Glycolytic Process | 0.322 | 0.807 |
| Immune T-cells | −0.286 | 0.262 |
| Immune B-cells | −0.226 | 0.873 |
| Cell cycle | −0.195 | 0.879 |
| NK regulation | −0.467 | 0.244 |
| Complement | 0.237 | 0.732 |
| Cancer - experimental | 0.776 | 0.459 |
| Acute response | 0.428 | 0.321 |
| Cytokine activity | −0.285 | 0.371 |
| Wound healing | 0.186 | 0.907 |
| Interferon | −0.324 | 0.154 |
| Interleukin-10 | −0.165 | 0.941 |
| GFR* signaling | −0.186 | 0.800 |
| Immune response | −0.163 | 0.928 |
| Immune Response Type 1 | −0.573 | 0.159 |
| Immune Response Type 2 | −0.799 | 0.023 |
| Immune Response - Complement | −0.189 | 0.721 |
| Immune Response - Complement - Acute Response | −0.183 | 0.804 |
| Acute phase | 0.331 | 0.450 |
| Hypoxia | −0.249 | 0.636 |
| Cancer | 0.166 | 0.874 |
| Cell adhesion | −0.208 | 0.631 |
| Mesenchymal transition | −0.354 | 0.599 |
| Extracellular matrix - restricted source, UNIPROT | −0.269 | 0.640 |
| Extracellular matrix - from different sources | −0.240 | 0.618 |
| Angiogenesis | −0.257 | 0.399 |

TABLE 9

Correlation of the individual proteins in the Immune Response Type 2 functional group with classification labels

| UniProtID | Protein Name | Correlation | P value |
|---|---|---|---|
| P05112 | Interleukin-4 | 0.017 | 0.920 |
| P01563 | Interferon-alpha2 | −0.020 | 0.904 |
| P17706 | Tyrosine-protein phosphatase non-receptor type 2 | −0.037 | 0.826 |
| Q8IU54 | Interferon-lambda 1 | −0.330 | 0.048 |

(In table 9 the correlation is rank sum based correlation). These results indicate a potential association of the "New classifier 1" test classification with immune response type 2 and the protein interferon-lambda 1 in particular.

This observation indicates that Type 2 immunity is down-regulated in patients classified as EarlyLate (better prognosis) as compared to EarlyEarly (poor prognosis). This finding is in line with existing body of information implicating Immune Response Type 2, in contrast to Immune Response Type 1, in cancer-promoting processes. Type 2 immunity has evolved as a mechanism of resistance to metazoan parasites such as helminthes; however, it can be activated by complex interactions between the host and the tumor and has been shown to regulate aspects of innate and adaptive immunity directly related to cancer. It involves an ever-expanding group of innate immune cells, such as basophils, eosinophils, mast cells, M2 macrophages (also known as alternatively activated macrophages), with CD4+ T helper cell type 2(Th2) functioning as the central mediators of the adaptive immune response (Gause, W. C., Wynn, T. A. & Allen, J. E. Type 2 immunity and wound healing: evolutionary refinement of adaptive immunity by helminths. *Nat Rev Immunol* 13, 607-14 (2013).)

While macrophages with M1 phenotype are characterized by high production of IL-12 and low expression of IL-10 cytokines, and can contribute to tumor control, the M2 phenotype, characteristic of immune response type 2 has an IL-12 low and IL-10 and TGFβ high profile that blocks the activity of anti-tumor effector immune cells and has protumorigenic role (Woo, S. R., Corrales, L. & Gajewski, T. F. Innate immune recognition of cancer. *Annu Rev Immunol* 33, 445-74 (2015). Berraondo, P. et al. Innate immune mediators in cancer: between defense and resistance. *Immunol Rev* 274, 290-306 (2016)). Markedly, M2 macrophages were shown to produce an array of cytokines and growth factors that promote angiogenesis and wound healing (Wynn, T. A. & Ramalingam, T. R. Mechanisms of fibrosis: therapeutic translation for fibrotic disease. *Nat Med* 18, 1028-40 (2012)), which, on the one hand, trended towards a significant association with our test, and, on the other hand, are known to be associated with tumorigenesis(Arwert, E. N., Hoste, E. & Watt, F. M. Epithelial stem cells, wound healing and cancer. *Nat Rev Cancer* 12, 170-80 (2012)). Furthermore, differentiation of CD4+T helper cells towards type I or type 2 phenotypes is defined by a complex interplay of cytokines (Mantovani, A., Allavena, P., Sica, A. & Balkwill, F. Cancer-related inflammation. *Nature* 454, 436-44 (2008)), and has an opposite effect on cancer: while Th1 cells activate antigen-presenting cells and can directly kill tumor cells, Th2 cells, associated with Type 2 immune responses, facilitate tumor growth (Gutkin, D. W. & Shurin, M. R. Clinical evaluation of systemic and local immune responses in cancer: time for integration. *Cancer Immunol Immunother* 63, 45-57 (2014). Knutson, K. L. & Disis, M. L. Tumor antigen-specific T helper cells in cancer immunity and immunotherapy. *Cancer Immunol Immunother* 54, 721-8 (2005), Protti, M. P. & De Monte, L. Cross-talk within the tumor microenvironment mediates Th2-type inflammation in pancreatic cancer. *Oncoimmunology* 1, 89-91 (2012)).

Therefore, we can propose a hypothesis that patients that are characterized by elevated acute-phase and complement processes (BDX008−) generally have inferior prognosis when treated with immunotherapies, however they are not uniform, and some still may benefit from treatment, however, those who are also characterized by Type 2 immunity (EarlyEarly) have especially dismal prognosis. Specific factors resulting in this particular phenotype are difficult to elucidate; however, the existing evidence points to multiple interactions between complement system, inflammation, and innate and adaptive immunity.

Since the effects that are measured in serum reflect the state of the innate and adaptive immunity on the global level, not just at a tumor site, the classifier is expected to be relevant for various cancers, including lung and renal cell carcinoma, and should not be restricted to melanoma. For the same reason it should be applicable for the broad variety of treatments affecting immunological status of the patient, such as various immune checkpoint inhibitors, including anti-PD1 and anti-CTLA drugs, high dose IL2 therapy, vaccines, and/or combinational therapy, including the combination of anti-PD1 and anti-CTLA4 drugs.

Combination of BDX008 ("IS2" from Example 1 of U.S. patent application Ser. No. 15/207,825 filed Jul. 12, 2016) with the New Classifier 1

Figure 5:
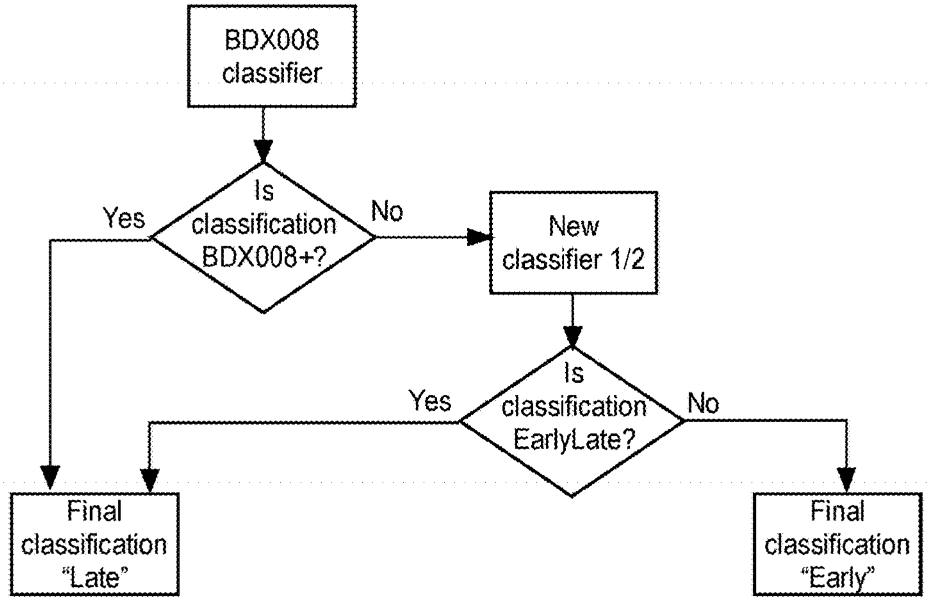
FIG. 5 is a schema of a hierarchical classification method by which a sample is first classified by the BDX008 classifier and then, if the class label is Early (BDX008−) or the equivalent, classifies the sample with either the "New classifier 1" or "New classifier 2"; if New classifier 1 or New classifier 2 produces an EarlyLate class label (or the equivalent) the patient is predicted to have relatively durable response to immunotherapy drugs.
Figure 6A:
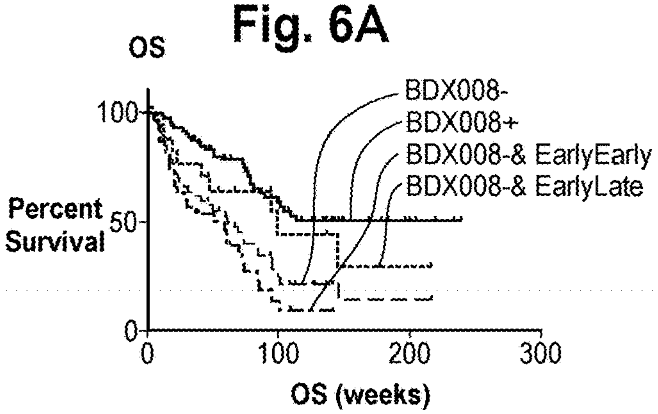
FIGS. 6A-6D are Kaplan-Meier plots by BDX008, combination of BDX008− and New classifier 1 classification (6A and 6C) and overall final combination classification (6B and 6D) for the Moffitt cohort.
Figure 6B:
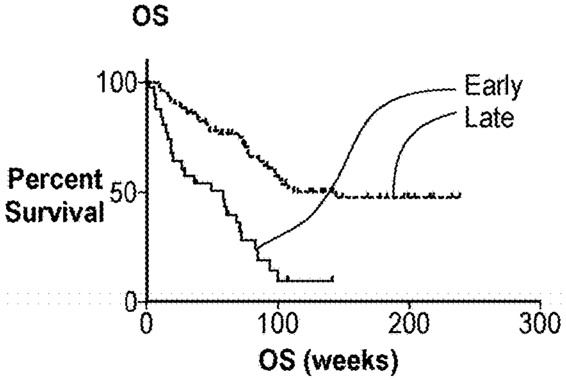
Figure 6C:
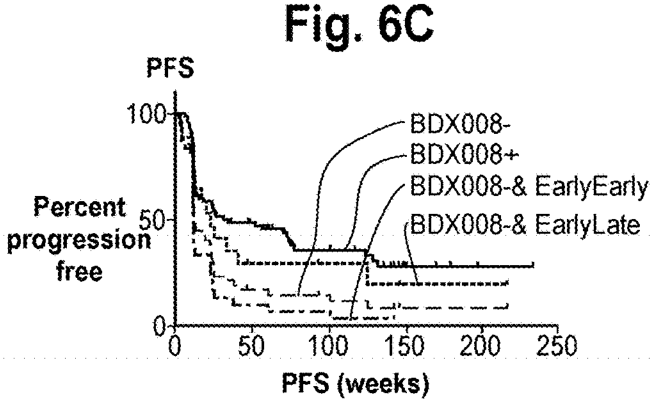
Figure 6D:
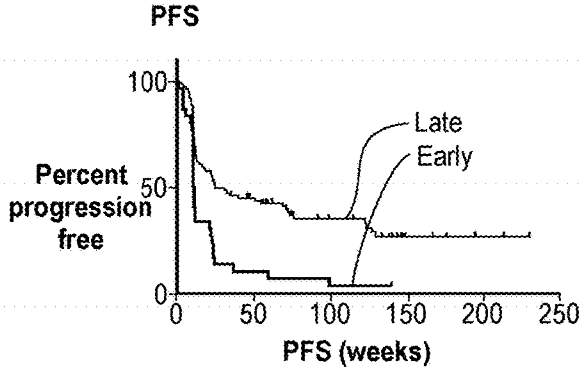

The "New classifier 1" was used to select patients from the BDX008− classification group, patients with particularly poor outcomes, as patients which have durable benefit from immunotherapy. If a sample was classified as BDX008+, its final classification is Late, independently of the label given by "New classifier 1". If it was classified as BDX008− and "New classifier 1" gives an EarlyEarly label, the final classification is Early. Finally, if the sample was classified as BDX008− and the classification given by "New classifier 1" gives an EarlyLate label, the final classification is Late. FIG. 5 consists of a flowchart that depicts the combination of the classification labels of BDX008 with those of "New classifier 1".

It will thus be seen that the BDX008 classifier is used to identify if the patient is in a poor prognosis subgroup (as identified by BDX008− class label). If the patient tests BDX008-, then the mass spectrum from the sample is classified by the "New classifier 1". If this classifier produces the EarlyLate class label (or the equivalent) the patient is predicted to have a durable benefit from immunotherapy in treatment of the cancer. Conversely, if the "New classifier 1" does not produce the EarlyLate label (e.g., produces an EarlyEarly class label, or the equivalent), the patient is classified as Early and is predicted to not have a durable benefit from immunotherapy (e.g., nivolumab) and is therefore guided to other treatment such as chemotherapy, palliative care, etc.

Moffitt Cohort

FIGS. 6A-6D are Kaplan-Meier plots by BDX008, combination of BDX008− and New classifier 1 classification (6A and 6C) and overall final combination classification (6B and 6D) for the Moffitt cohort. The performance is shown in Table 10 below.

TABLE 10

Summary of the performance of the BDX008 test and the combination of BDX008 with "New classifier 1" on the Moffitt cohort

| | | OS HR (95% CI) | OS log-rank p | OS Median (Group1, Group2) | PFS HR (95% CI) | PFS log-rank p | PFS Median (Group1, Group2) |
|---|---|---|---|---|---|---|---|
| BDX008 | #BDX008−/#BDX008+ 47/72 | 0.38 (0.19-0.55) | <0.001 | 61, not reached (weeks) | 0.50 (0.29-0.71) | 0.001 | 12, 32.9 (weeks) |
| Combination of BDX008 and "New classifier 1" | #Early/#Late 30/89 | 0.30 (0.09-0.34) | <0.0001 | 50, 113 (weeks) | 0.40 (0.16-0.49) | <0.0001 | 11.2, 26.1 (weeks) |

Baseline clinical characteristics are summarized by classification group, for BDX008 and for the combination of BDX008 with the new classifier, in Table 11.

TABLE 11

Baseline characteristics and response by classification group for BDX008 and for the combination of BDX008 with "New classifier 1" on the Moffitt cohort

| | | BDX008− (N = 47) n (%) | BDX008+ (N = 72) n (%) | Early (N = 30) n (%) | Late (N = 89) n (%) |
|---|---|---|---|---|---|
| Gender | Male | 28 (60) | 44 (61) | 15 (50) | 57 (64) |
| | Female | 17 (36) | 28 (39) | 14 (47) | 31 (35) |
| Age | Median | 63 | 60 | 60 | 62 |
| | (Range) | (23-86) | (16-87) | (23-86) | (16-87) |
| Response | PR | 7 (15) | 24 (33) | 2 (7) | 29 (33) |
| | SD | 4 (9) | 14 (19) | 2 (7) | 16 (18) |
| | PD | 36 (77) | 34 (47) | 26 (87) | 44 (49) |
| Prior | No | 10 (21) | 21 (29) | 7 (23) | 24 (27) |
| ipilimumab | Yes | 37 (79) | 51 (71) | 23 (77) | 65 (73) |
| VeriStrat | good | 26 (55) | 72 (100) | 19 (63) | 79 (89) |
| classification | poor | 21 (45) | 0 (0) | 11 (37) | 10 (11) |
| PD-L1 | Positive | 3 (6) | 5 (7) | 1 (3) | 7 (8) |
| expression | Negative | 15 (32) | 14 (19) | 11 (37) | 18 (20) |
| (5% tumor) | NA | 29 (62) | 53 (74) | 18 (60) | 64 (72) |
| PD-L1 | Positive | 9 (19) | 9 (13) | 6 (20) | 12 (13) |
| expression | Negative | 9 (19) | 10 (14) | 6 (20) | 13 (15) |
| (1% tumor) | NA | 29 (62) | 53 (74) | 18 (60) | 64 (72) |
| PD-L1 | Positive | 13 (28) | 15 (21) | 9 (30) | 19 (21) |
| expression | Negative | 4 (9) | 3 (4) | 3 (10) | 4 (4) |
| (1% tumor/ | NA | 30 (64) | 54 (75) | 18 (60) | 66 (74) |
| immune cells) | | | | | |

Yale Nivo Cohort

Figure 7A:
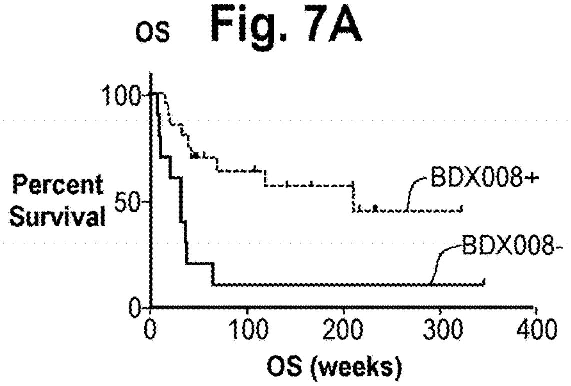
FIG. 7A-7B are Kaplan-Meier plots by BDX008 (7A) and overall final combination classification (7B) for the Yale Nivo (nivolumab) cohort.
Figure 7B:
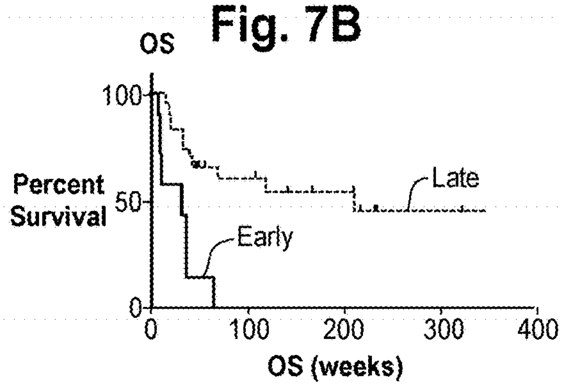

FIG. 7A-7B are Kaplan-Meier plots by BDX008 (7A) and overall final combination classification (7B) for the Yale Nivo (nivolumab) cohort. Performance is described in Table 12.

TABLE 12

Summary of the performance of the BDX008 test and the combination of BDX008 with "New classifier 1" on the Yale Nivo cohort

| | | OS HR (95% CI) | OS log-rank p | OS Median (Group1, Group2) |
|---|---|---|---|---|
| BDX008 | #BDX008−/#BDX008+ 10/20 | 0.27 (0.05-0.52) | 0.0024 | 31.6, 210.1 (weeks) |
| Combination of BDX008 with "New classifier 1" | #Early/#Late 7/23 | 0.22 (0.02-0.29) | 0.0004 | 31.6, 210.1 (weeks) |

"Yale" Ipi Cohort

Figure 8A:
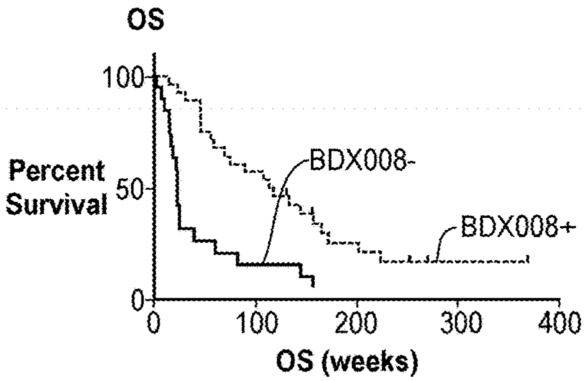
FIGS. 8A-8B are Kaplan-Meier plots by BDX008 (8A) and overall final combination classification (8B) for the Yale Ipi (ipilimumab) cohort.
Figure 8B:
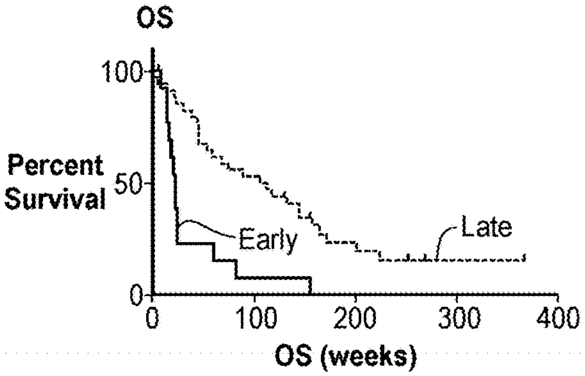
Figure 9A:
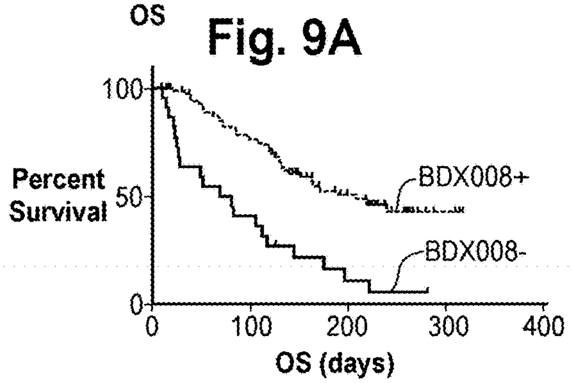
FIGS. 9A-9D are Kaplan-Meier plots by BDX008 (9A and 9C) and overall final combination classification (9B and 9D) for the IL2 (interleukin-2) MGH (Massachusetts General Hospital) cohort.
Figure 9B:
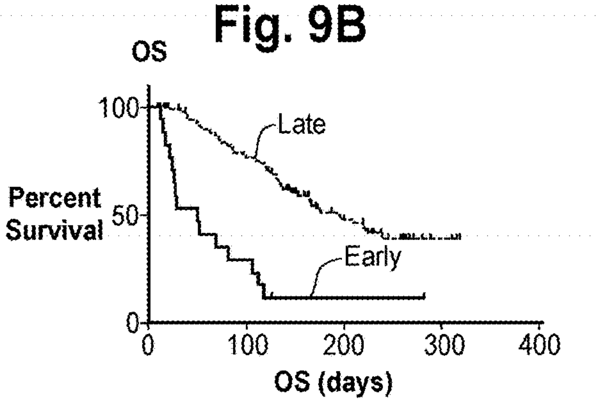
Figure 9C:
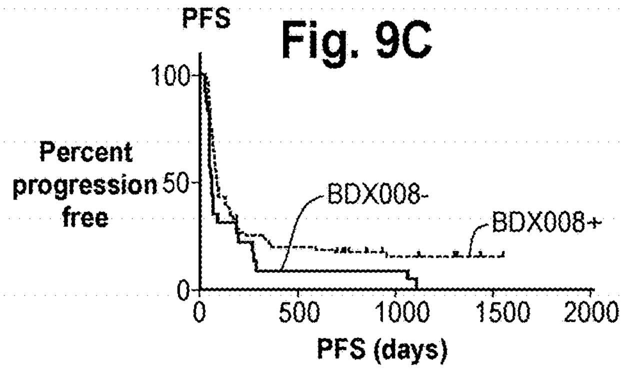
Figure 9D:
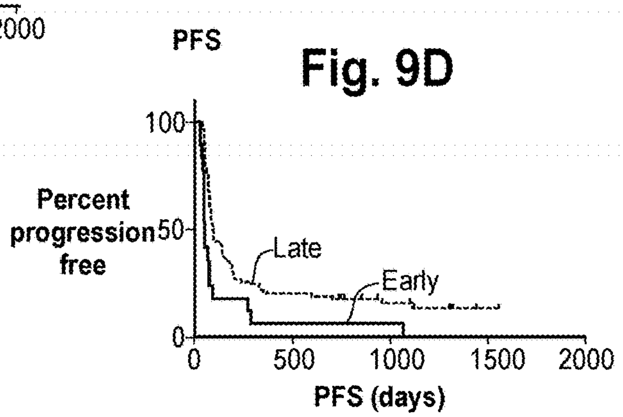

FIGS. 8A-8B are Kaplan-Meier plots by BDX008 (8A) and overall final combination classification (8B) for the Yale Ipi (ipilimumab) cohort.

TABLE 13

Summary of the performance of the BDX008 test and the combination of BDX008 with "New classifier 1" on the Yale Ipi cohort

| | | OS HR (95% CI) | OS log-rank p | OS Median (Group1, Group2) |
|---|---|---|---|---|
| BDX008 | #BDX008−/#BDX008+ 20/28 | 0.33 (0.10-0.47) | 0.0002 | 22.3, 115 (weeks) |
| Combination of BDX008 with "New classifier 1" | #Early/#Late 14/34 | 0.30 (0.06-0.37) | <0.0001 | 22.3, 110 (weeks) |

IL2 MGH Cohort

FIGS. 9A-9D are Kaplan-Meier plots by BDX008 (9A and 9C) and overall final combination classification (9B and 9D) for the IL2 (interleukin-2) NIGH (Massachusetts General Hospital) cohort.

TABLE 14

Summary of the performance of the BDX008 test and the combination of BX008 with "New classifier 1" on the MGH IL2 treated cohort.

| | | OS HR (95% CI) | OS log-rank p | OS Median (Group1, Group2) | PFS HR (95% CI) | PFS log-rank p | PFS Median (Group1, Group2) |
|---|---|---|---|---|---|---|---|
| BDX008 | #BDX008−/#BDX008+ 23/89 | 0.29 (0.07-0.33) | <0.0001 | 372.5, 1037.0 (days) | 0.59 (0.30-0.91) | 0.023 | 57.0, 84.0 (days) |
| Combination of BDX008 with "New classifier 1" | #Early/#Late 17/95 | 0.20 (0.11-0.37) | <0.0001 | 245.0, 952.0 (days) | 0.44 (0.15-0.63) | 0.0013 | 45.0, 86.0 (days) |

TABLE 15

Response by classification group for BDX008 and for the combination of BDX008 with "New classifier 1" on the MGH IL2 treated cohort.

| | | BDX008− (N = 23) n (%) | BDX008+ (N = 89) n (%) | Early (N = 17) n (%) | Late (N = 95) n (%) |
|---|---|---|---|---|---|
| Response | NA | 0 (0) | 1 (1) | 0 (0) | 1 (1) |
| | CR | 0 (0) | 8 (9) | 0 (0) | 8 (8) |
| | MR | 0 (0) | 6 (7) | 0 (0) | 6 (6) |
| | PD | 16 (70) | 44 (49) | 14 (82) | 46 (48) |
| | PR | 4 (17) | 9 (10) | 2 (12) | 11 (12) |
| | SD | 3 (13) | 21 (24) | 1 (6) | 23 (24) |

IL2 Curti Cohort

Figure 10A:
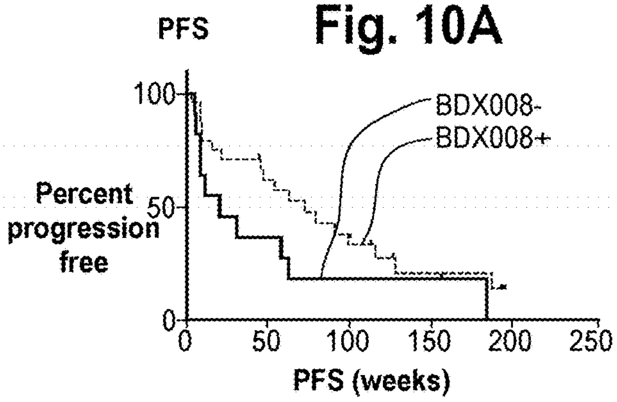
FIG. 10A-10B are Kaplan-Meier plots by BDX008 (10A) and overall final combination classification (10B) for the IL-2 Curti cohort.
Figure 10B:
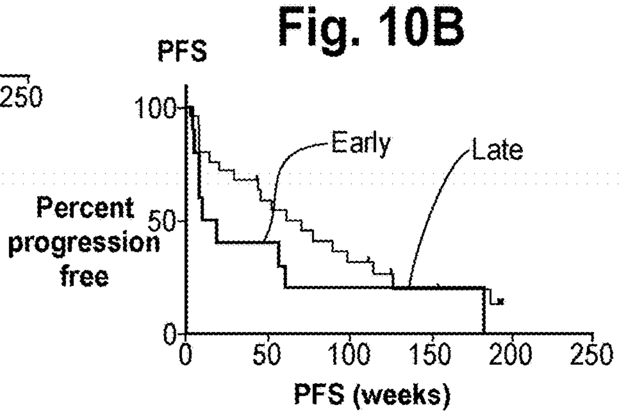

FIGS. 10A-10B are Kaplan-Meier plots by BDX008 (10A) and overall final combination classification (10B) for the IL2 Curti cohort.

TABLE 16

Summary of the performance of BDX008 and the combination of BDX008 with "New classifier 1" on the Curti IL2 treated cohort

| | | PFS HR (95% CI) | PFS log-rank p | PFS Median (Group1, Group2) |
|---|---|---|---|---|
| BDX008 | #BDX008−/#BDX008+ 11/26 | 0.55 (0.21-1.19) | 0.123 | 19.9, 71.1 (weeks) |
| Combination of BDX008 with "New classifier 1" | #Early/#Late 10/27 | 0.59 (0.22-1.31) | 0.177 | 15.1, 71.1 (weeks) |

This body of data indicate that the combination of BDX008 and New classifier 1 is able to provide a better identification of patients likely to have the poorest outcomes (Early classification) when treated with a variety of immunotherapeutic regimens, including nivolumab, ipilimumab, and high dose IL-2. Given this wide range of applicability, it is very likely that this test combining BDX008 and New classifier 1 will also have utility in closely related immunotherapy regimens, such as other drugs targeting PD-1 or PD-L1 (including but not limited to pembrolizumab, avelumab, and atezolizumab), other drugs targeting CTLA4 (e.g. tremelimumab), combinations of anti-PD-1/PD-L1 therapy with anti-CTLA4 therapy, such as the combination of nivolumab with ipilimumab, and other regimens incorporating IL-2 administration. Furthermore, the breadth of demonstrated applicability beyond checkpoint inhibitors to high dose IL-2 administration means that it is also possible that the utility of the test could extend to other less closely related immunotherapies such as vaccines, other checkpoint inhibitors and combinations thereof or to combinations of immunotherapies with chemotherapy.

Figure 11:
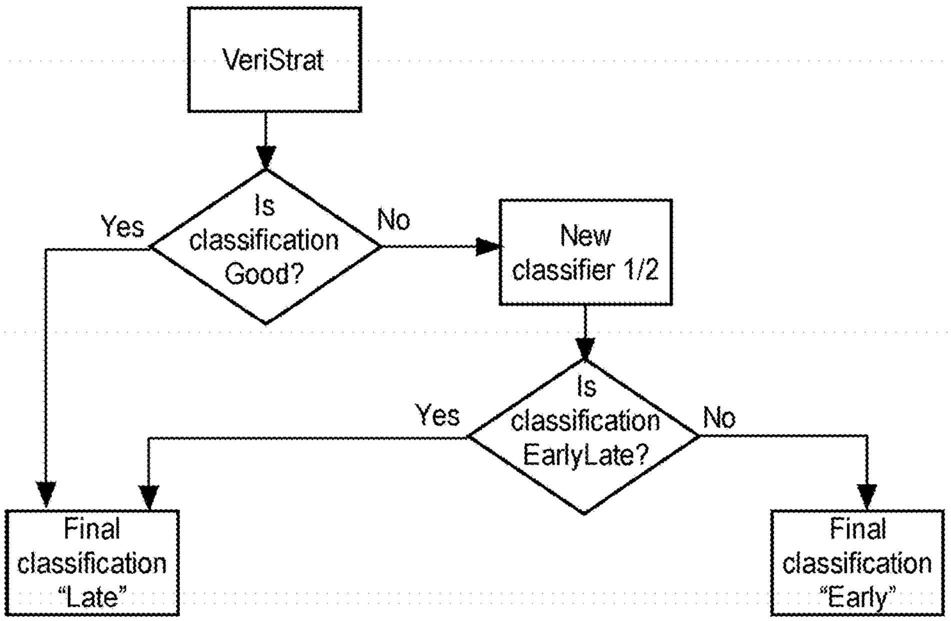
FIG. 11 is a diagram of a schema showing use of VeriStrat® (see U.S. Pat. No. 7,736,905, assigned to Biodesix, Inc., the content of which is incorporated by reference herein), another mass spectrometry test which identifies patients with a poor prognosis (class label Poor) and "New classifier 1 or 2" (described below) to hierarchically generate a test classification which predicts durable patient benefit from immunotherapy drugs from the poor performing group.
Figure 12A:
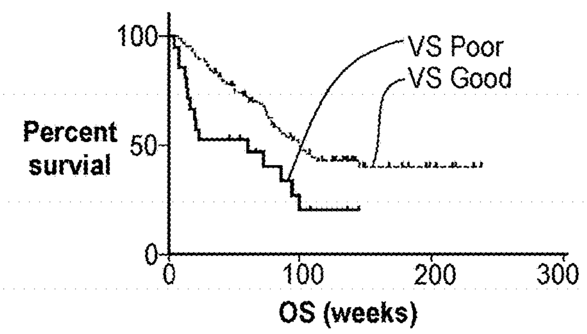
FIGS. 12A-12D are Kaplan-Meier plots showing OS and PFS by VeriStrat classification (12A and 12C) and the combination of VeriStrat and New classifier 1 (12B and 12D) for the Moffitt cohort.
Figure 12B:
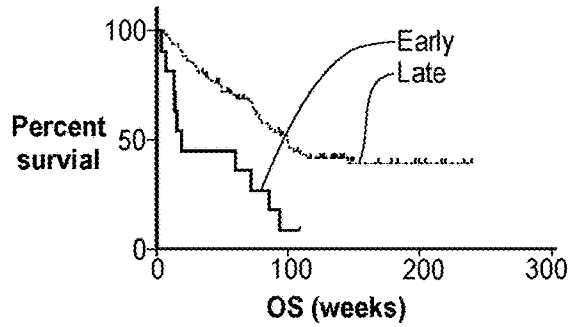
Figure 12C:
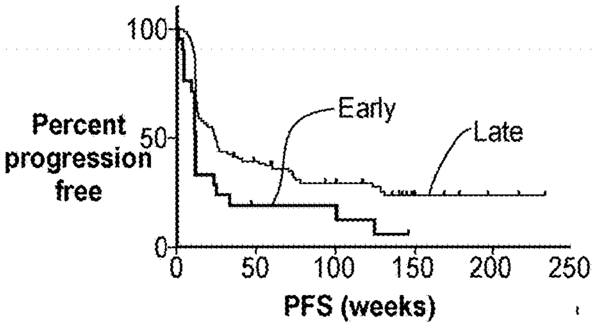
Figure 12D:
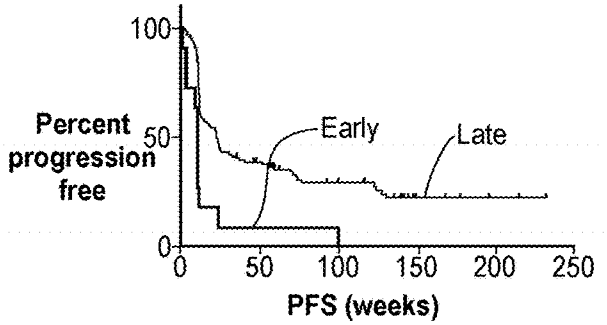

Combination of VeriStrat (U.S. Pat. No. 7,356,905) with the New classifier 1 to guide immunotherapy treatment for poor prognosis subgroups The VeriStrat (VS) test produces a binary class label, Good or Poor, with the Poor class label associated with poor prognosis. The "New classifier 1" was used to select patients from the VeriStrat Poor classification group with particularly bad outcomes. In this way, if a sample was classified as Good by Veristrat, its final classification was Late, independently of the label given by the "New classifier 1". If it was classified as Poor by VeriStrat and "New classifier 1" gave an EarlyEarly label, the final classification was Early. Finally, if the sample was classified Poor by VeriStrat and the classification given by "New classifier 1" was an EarlyLate label, the final classification was Late. FIG. 11 shows a flowchart that depicts the combination of the classification labels of VeriStrat with those of "New classifier 1". The Late class label in the schema of FIG. 11 indicates that the patient is likely to have durable benefit from immunotherapy in treatment of cancer.

FIGS. 12A-12D are Kaplan-Meier plots showing OS and PFS by VeriStrat classification (12A and 12C) and the combination of VeriStrat and New classifier 1 (12B and 12D) for the Moffitt cohort. Recall that the Moffitt cohort consisted of blood samples obtained pre-treatment from a set of melanoma patients subsequently treated with nivolumab. Notice the clear separation between the Early and Late groups in terms of OS and PFS. The statistics of classifier performance are shown in Table 17.

TABLE 17

Summary of the performance of the VeriStrat test and the combination of Veristrat with "New classifier 1" on the Moffitt cohort

| | | OS HR (95% CI) | OS log-rank p | OS Median (Group1, Group2) | PFS HR (95% CI) | PFS log-rank p | PFS Median (Group1, Group2) |
|---|---|---|---|---|---|---|---|
| VeriStrat | VS Poor/ VS Good 21/98 | 0.45 (0.16-0.72) | 0.005 | 60, 100 (weeks) | 0.48 (0.19-0.71) | 0.003 | 11, 23.7 (weeks) |
| Combination of VeriStrat with "New classifier 1" | #Early/#Late 11/108 | 0.32 (0.05-0.41) | <0.001 | 20, 99 (weeks) | 0.31 (0.04-0.34) | <0.001 | 10.9, 23.5 (weeks) |

Baseline clinical characteristics are summarized by classification group, for VeriStrat and for the combination of VeriStrat with the "New classifier 1", in Table 18.

TABLE 18

Baseline characteristics and response by classification group for VeriStrat and for the combination of VeriStrat with "New classifier 1" on the Moffitt cohort

| | | VS Poor (N = 21) n (%) | VS Good (N = 98) n (%) | Early (N = 11) n (%) | Late (N = 108) n (%) |
|---|---|---|---|---|---|
| Gender | Male | 13 (62) | 59 (60) | 5 (45) | 67 (62) |
| | Female | 7 (33) | 38 (39) | 5 (45) | 40 (37) |
| Age | Median (Range) | 63 (23-86) | 60 (16-87) | 58 (23-86) | 62 (16-87) |
| Response | PR | 3 (14) | 28 (29) | 0 (0) | 31 (29) |
| | SD | 2 (10) | 16 (16) | 1 (9) | 17 (16) |
| | PD | 16 (76) | 54 (55) | 10 (91) | 60 (56) |
| Prior ipilimumab | No | 5 (24) | 26 (27) | 4 (36) | 27 (25) |
| | Yes | 16 (76) | 72 (73) | 7 (64) | 81 (75) |
| PD-L1 expression (5% tumor) | Positive | 3 (14) | 5 (5) | 1 (9) | 7 (6) |
| | Negative | 4 (19) | 25 (26) | 3 (27) | 26 (24) |
| | NA | 14 (67) | 68 (69) | 7 (64) | 75 (69) |
| PD-L1 expression (1% tumor) | Positive | 5 (24) | 13 (13) | 3 (27) | 15 (14) |
| | Negative | 2 (10) | 17 (17) | 1 (9) | 18 (17) |
| | NA | 14 (67) | 68 (69) | 7 (64) | 75 (69) |
| PD-L1 expression (1% tumor/ immune cells) | Positive | 6 (29) | 22 (22) | 3 (27) | 25 (23) |
| | Negative | 1 (5) | 6 (6) | 1 (9) | 6 (6) |
| | NA | 14 (67) | 70 (71) | 7 (64) | 77 (71) |

Extension to Other Tumor Types, Including NSCLC

The classification of a small fraction of serum samples from patients with durable benefit into poor prognosis groups has been observed in other tests developed using the procedure of FIG. 3 as well. Namely, a classifier that splits Non-Small Cell Lung Cancer (NSCLC) patients according to better/worse outcome during treatment with nivolumab has been constructed using the procedure of FIG. 3 explained above, using as a classifier development set of 98 pre-treatment samples from patients with advanced NSCLC (the nivolumab lung cohort).

Such a classifier ("N SCLC classifier" herein) was designed to take advantage of subsets of mass spectral features which have been identified as being associated with certain protein functional groups. This is done using the principles of gene set enrichment analysis. First, the whole nivolumab lung cohort was used with the subset of 28 mass spectral features associated with acute response in the procedure of FIG. 3 to create a classifier able to stratify patients into two groups with better and worse prognosis in terms of OS and PFS. Thirty-nine samples were assigned to the poor performing group. The remaining 59 samples, assigned to the good performing group, were used as the development set for a second classifier. This classifier was trained on the subset of 32 mass spectral features which had been identified as being associated with wound healing, but not associated with acute response or immune response. The second classifier stratified patients well into groups with better or worse OS/PFS. Samples classified by the first classifier (based on acute response MS features) as belonging to the poor performing group were given the "Early" final classification. Those assigned to the good performing group by the first classifier were given the classification of the second classifier (based on wound healing MS features, either "Early"=poor prognosis or "Late"=good prognosis) as the final classification of the "NSCLC classifier." Note that this template for new classifier development has been used before with melanoma samples to create a test able to effectively identify patients with very good outcomes on nivolumab therapy (see Example 6 of our prior patent application Ser. No. 15/207,825, filed Jul. 12, 2016, the content of which is incorporated by reference herein).

For completeness we here also describe the application of the "NSCLC classifier". This is a hierarchical combination of two diagnostic cortex classifiers as shown in the schema of FIG. 22. First a sample is classified by a diagnostic cortex classifier using only mass spectral features found to be associated with acute response. If the sample classifies as "Early" (poor prognosis) from this first classifier, a "NSCLC classifier" classification of "Early". If the sample classifies as "Late" (good prognosis) from this first classifier, the second diagnostic cortex classifier, which uses only mass spectral features found to be associated with wound healing but not with acute response or immune response, is applied to the sample. If the sample classifies as "Early" from the second classifier, the sample receives a "NSCLC classifier" classification of "Early" and if it classifies as "Late" the sample receives a "NSCLC classifier" classification of "Late". The Early class label is associated with poor prognosis.

FIG. 13 shows the Kaplan-Meier plots for OS and PFS split by final classifications, as given by the "NSCLC classifier", for the nivolumab lung cohort. Long plateaus exist in the poor outcome curves for both OS and PFS.

The nivolumab lung cohort samples were run through "New classifier 1", described in the previous section, with the aim of identifying samples assigned to the poor prognosis group by the "NSCLC classifier" with durable benefit that could, potentially, be moved to the good prognosis group. FIG. 14 shows the distribution of the averaged probabilities for the samples in the nivolumab lung cohort that are BDX008−, in comparison with the distribution for the samples in the "Moffitt" cohort classified as BDX008−. While the average probability distribution for the Moffitt case is balanced across the whole range [0,1], the distribution for the nivolumab lung case is skewed towards higher values. This suggests that the two oncology indications (melanoma and lung) do not correspond to the same patient populations in terms of their serum protein content. With this in mind, a new average probability cutoff was chosen to define a new classifier, called "New classifier 2", more suitable for selection of NSCLC patients with durable benefit from immunotherapy in otherwise poor prognosis subgroups.

FIG. 14A shows the distribution of the averaged probabilities for the samples in the "Moffitt" cohort that are BDX008−; FIG. 14B shows the distribution of the averaged probabilities for the samples in the "nivolumab lung" cohort classified as BDX008−. The vertical line 1401 represents the cutoff of 0.459 that defines the "New classifier 1" and the line 1402 represents the cutoff of 0.869 chosen to define the "New classifier 2". (See previous discussion of the ROC curve of FIG. 4 for "New Classifier 1").

Figure 15:
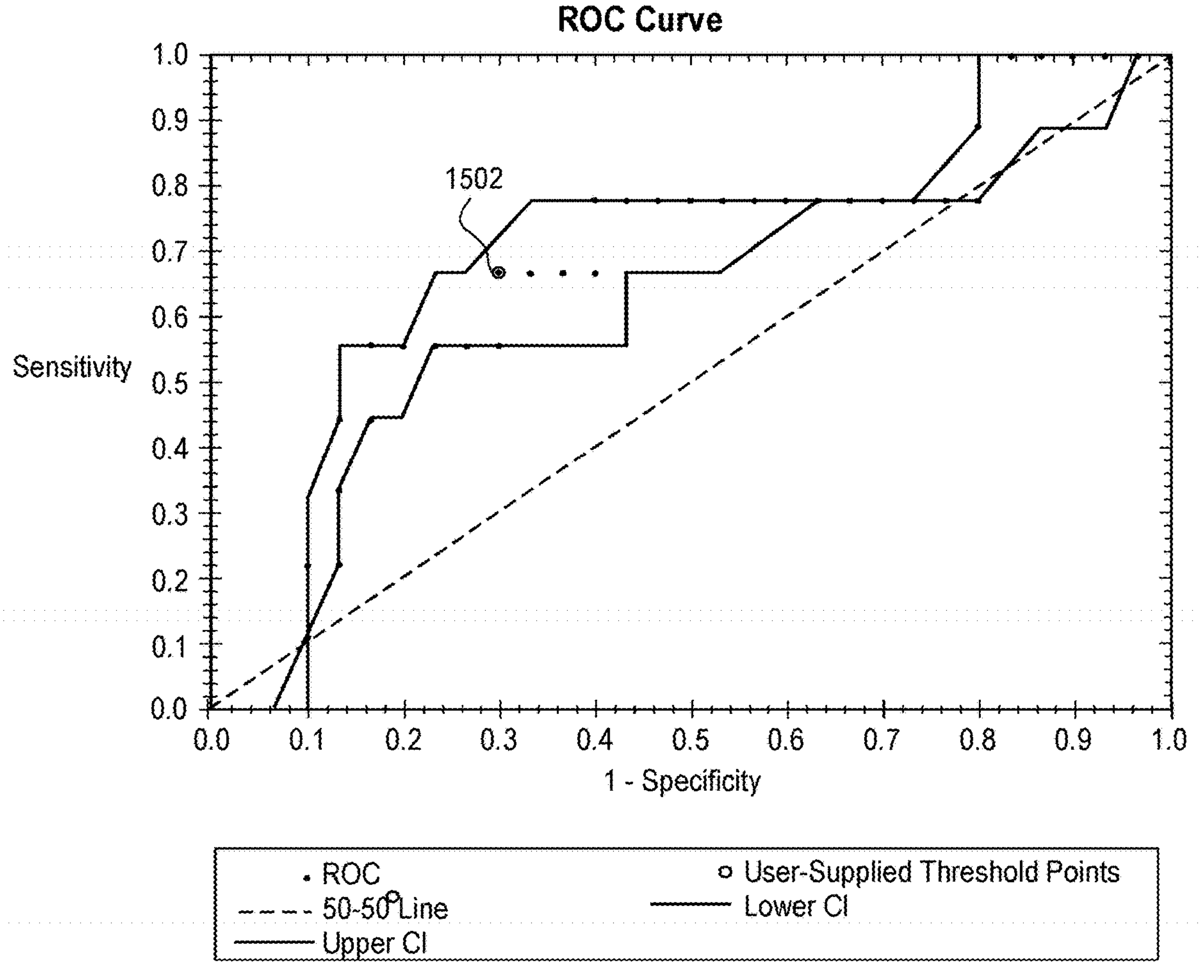
FIG. 15 is an ROC curve for a subset of samples from the nivolumab lung cohort showing the choice of cutoff for "New classifier 2." The upper and lower CI lines should be ignored.
Figure 16A:
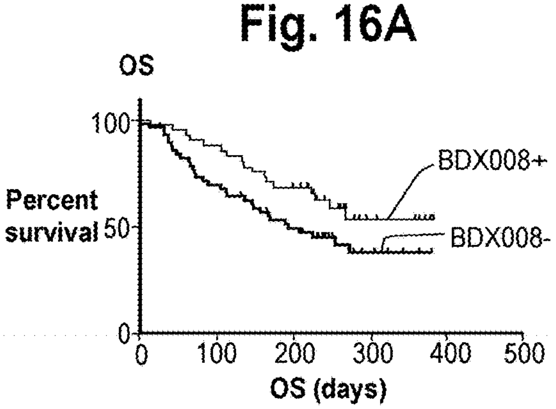
FIGS. 16A-16D are Kaplan-Meier plots split by classification group (BDX008—16A and 16C—and combination of BDX008 with "New classifier 2"—16B and 16D) shown for the nivolumab lung cohort.
Figure 16B:
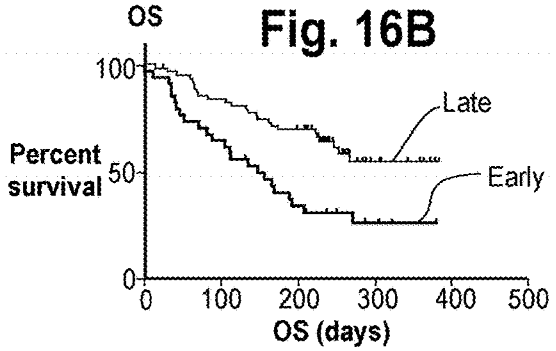
Figure 16C:
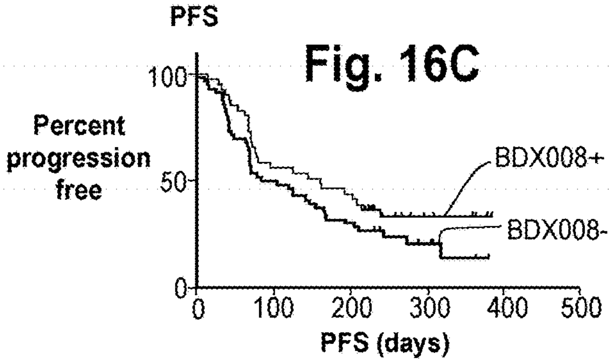
Figure 16D:
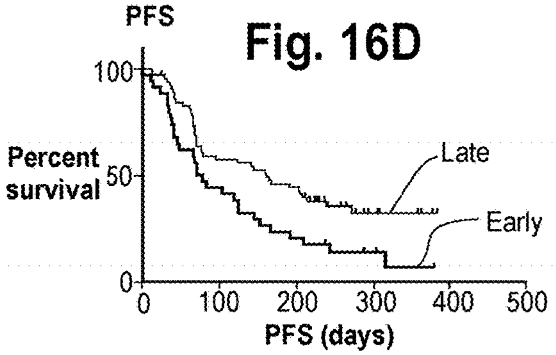

The selection of the new cutoff to be used in NSCLC cohorts, was chosen as follows. An ROC curve was plotted using the 39 samples from the "nivolumab lung" cohort that were assigned to the poor prognosis group by the subclassifier developed with the 28 mass spectral features associated with acute response, as part of the "NSCLC" classifier. The average probabilities plotted are those provided by "New classifier 1". The ROC curve obtained in this way is shown in FIG. 15 and corresponds to an area under the curve of 0.674. The cutoff of 0.869 to be applied to the averaged probabilities was chosen in order to optimize simultaneously sensitivity and specificity, and corresponds to the circle 1502 shown in FIG. 15. The classifier defined by this new cutoff was called "New classifier 2", and is referred to as such in this document. Note that New classifier 1 and New classifier 2 are based on identical MCs, and differ only in choice of the cutoff that turns the averaged probability over the ensemble of MCs into a binary classification.

Combination of BDX008 and New Classifier 2

As explained previously, the BDX008− classification group (Early in the IS2 classifier of Example 1 of our prior patent application Ser. No. 15/207,825) is associated with a poor prognosis. The "New classifier 2" was used to select patients from the BDX008− classification group with particularly bad outcomes. In this way if a sample was classified as BDX008+, its final classification was Late, independently of the label given by "New classifier 2". If it was classified as BDX008− and "New classifier 2" gave an EarlyEarly label (or the equivalent), the final classification is Early. Finally, if the sample was classified as BDX008− and the classification given by "New classifier 2" was an EarlyLate label (or the equivalent), the final classification is Late. The Late class label is associated with durable benefit from immunotherapy drugs in treatment of cancer.

FIG. 5 consists of a flowchart that depicts the combination of the classification labels of BDX008 with those of "New classifier 2". (It will be noted that the schema of this classification regime is the same as the combination of BDX008 and New classifier 1 described previously).

In FIG. 16. Kaplan-Meier plots split by classification group (BDX008-16A and 16C- and combination of BDX008 with "New classifier 2"-16B and 16D) are shown for the nivolumab lung cohort and the corresponding performance summaries arc given in Table 19. Baseline characteristics and best response, also split by classification groups, are shown in Table 20.

TABLE 19

Summary of the performance of the BDX008 test and the combination of BX008 with "New classifier 2" on the "nivolumab lung" cohort

| | | OS HR (95% CI) | OS log-rank p | OS Median (Group1, Group2) | PFS HR (95% CI) | PFS log-rank p | PFS Median (Group1, Group2) |
|---|---|---|---|---|---|---|---|
| BDX008 | #BDX008−/#BDX008+ 57/41 | 0.58 (0.34-1.04) | 0.067 | 192, not reached (days) | 0.69 (0.44-1.11) | 0.131 | 105, 161 (days) |
| Combination of BDX008 with "New classifier 2" | #Early/#Late 34/64 | 0.40 (0.18-0.64) | 0.001 | 147, not reached (days) | 0.54 (0.30-0.84) | 0.009 | 75, 162 (days) |

TABLE 20

Baseline characteristics and best response by classification group for BDX008 and for the combination of BDX008 with "New classifier 2" on the "nivolumab lung" cohort

| | n (%) | BDX008− (N = 57) n (%) | BDX008+ (N = 41) n (%) | Early (N = 34) n (%) | Late (N = 64) n (%) |
|---|---|---|---|---|---|
| Gender | Male | 36 (63) | 15 (37) | 21 (62) | 30 (47) |
| | Female | 21 (37) | 26 (63) | 13 (38) | 34 (53) |
| Treatment Line | 2 | 37 (65) | 21 (51) | 22 (65) | 36 (56) |
| | 3 | 14 (25) | 17 (41) | 8 (24) | 23 (36) |
| | 4 | 5 (9) | 3 (7) | 3 (9) | 5 (8) |
| | 5 | 1 (2) | 0 (0) | 1 (3) | 0 (0) |
| Performance Status | 0 | 7 (12) | 13 (32) | 3 (9) | 17 (27) |
| | 1 | 39 (68) | 26 (63) | 24 (71) | 41 (64) |
| | 2 | 11 (19) | 2 (5) | 7 (21) | 6 (9) |
| Smoking Status | Current | 17 (30) | 6 (15) | 7 (21) | 16 (25) |
| | Former | 36 (63) | 29 (71) | 25 (74) | 40 (63) |
| | Never | 3 (5) | 5 (12) | 2 (6) | 6 (9) |
| | Unknown | 1 (2) | 1 (2) | 0 (0) | 2 (3) |
| Best response | CR | 0 (0) | 1 (2) | 0 (0) | 1 (2) |
| | PR | 14 (25) | 8 (20) | 6 (18) | 16 (25) |
| | SD | 18 (32) | 13 (32) | 11 (32) | 20 (31) |

TABLE 20-continued

Baseline characteristics and best response by classification group for BDX008 and for the combination of BDX008 with "New classifier 2" on the "nivolumab lung" cohort

| n (%) | BDX008− (N = 57) n (%) | BDX008+ (N = 41) n (%) | Early (N = 34) n (%) | Late (N = 64) n (%) |
|---|---|---|---|---|
| PD | 20 (35) | 17 (42) | 14 (41) | 23 (36) |
| NE | 5 (9) | 1 (2) | 3 (9) | 3 (5) |
| NA | 0 (0) | 1 (2) | 0 (0) | 1 (2) |

Combination of "NSCLC Classifier" with the New Classifier 2

The "New classifier 2" was used to select patients from the Early classification group, as given by the "NSCLC classifier", with particularly bad outcomes. In this way, if a sample was classified as Late by the "NSCLC classifier", its final classification was Late, independently of the label given by "New classifier 2". If it was classified as Early by the "NSCLC classifier" and the "New classifier 2" gave an EarlyEarly label, the final classification was Early. Finally, if the sample was classified as Early by the "NSCLC classifier" and the classification given by "New classifier 2" was an EarlyLate label, the final classification was Late. The Late classification group is associated with a prediction of more durable benefit in NSCLC patients on immunotherapy.

FIG. 17 shows a flowchart that depicts the combination of the classification labels of the "NSCLC classifier" with those of "New classifier 2".

In FIG. 18, Kaplan-Meier plots split by classification group ("NSCLC classifier"—18A and 18C—and combination of "NSCLC classifier" with "New classifier 2"—18B and 18D) are shown for the "nivolumab lung" cohort and the corresponding performance summaries are given in Table 21. Baseline characteristics and best response, also split by classification groups, are shown in Table 22.

TABLE 21

Summary of the performance of the "NSCLC classifier" and the combination "NSCLC classifier" with the "New classifier 2" on the "nivolumab lung" cohort

| | | OS HR (95% CI) | OS log-rank p | OS Median (Group1, Group2) | PFS HR (95% CI) | PFS log-rank p | PFS Median (Group1, Group2) |
|---|---|---|---|---|---|---|---|
| "NSCLC classifier" | #Early/#Late 65/33 | 0.32 (0.22-0.68) | 0.001 | 166, not reached (days) | 0.52 (0.34-0.86) | 0.011 | 77, 208 (days) |
| Combination of the "NSCLC classifier" with "New classifier 2" | #Early/#Late 34/64 | 0.32 (0.13-0.46) | <0.001 | 136, not reached (days) | 0.46 (0.24-0.68) | 0.001 | 71, 168 (days) |

TABLE 22

Baseline characteristics and best response by classification group for the "NSCLC classifier" and for the combination of the "NSCLC classifier" with "New classifier 2" on the "nivolumab lung" cohort

| | | "NSCLC classifier" | | "NSCLC classifier" combined with "New classifier 2" | |
|---|---|---|---|---|---|
| | | Early (N = 65) n (%) | Late (N = 33) n (%) | Early (N = 34) n (%) | Late (N = 64) n (%) |
| Gender | Male | 37 (57) | 14 (42) | 21 (62) | 30 (47) |
| | Female | 28 (43) | 19 (58) | 13 (38) | 34 (53) |
| Treatment Line | 2 | 36 (55) | 22 (67) | 21 (62) | 37 (58) |
| | 3 | 21 (32) | 10 (30) | 9 (26) | 22 (34) |
| | 4 | 7 (11) | 1 (3) | 3 (9) | 5 (8) |
| | 5 | 1 (2) | 0 (0) | 1 (3) | 0 (0) |
| Performance Status | 0 | 9 (14) | 11 (33) | 3 (9) | 17 (27) |
| | 1 | 45 (69) | 20 (61) | 25 (74) | 40 (63) |
| | 2 | 11 (17) | 2 (6) | 6 (18) | 7 (11) |
| Smoking Status | Current | 19 (29) | 4 (12) | 8 (24) | 15 (23) |
| | Former | 38 (58) | 27 (82) | 24 (71) | 41 (64) |
| | Never | 7 (11) | 1 (3) | 2 (6) | 6 (9) |
| | Unknown | 1 (2) | 1 (3) | 0 (0) | 2 (3) |
| Best response | CR | 0 (0) | 1 (3) | 0 (0) | 1 (2) |
| | PR | 15 (23) | 7 (21) | 5 (15) | 17 (27) |
| | SD | 17 (26) | 14 (42) | 10 (29) | 21 (33) |
| | PD | 28 (43) | 9 (27) | 16 (47) | 21 (33) |
| | NE | 5 (8) | 1 (3) | 3 (9) | 3 (5) |
| | NA | 0 (0) | 1 (3) | 0 (0) | 1 (2) |

Comparison with Chemotherapy Cohort in $2^{nd}$ Line Patients

In FIG. 19, Kaplan-Meier plots split by "NSCLC classifier" classification group (19A and 19C) and combination of the "NSCLC classifier" with the "New classifier 2" (19B and 19D) are shown for the patients in the "nivolumab lung" cohort that received $2^{nd}$ line treatment. The curves are compared with those obtained for the PROSE cohort ($2^{nd}$ line NSCLC cancer patients treated with docetaxel).

Combination of VeriStrat with the "New Classifier 2"

The "New classifier 2" was used to select patients from the VeriStrat Poor classification group with particularly bad outcomes. In this way, if a sample was classified as Good by VeriStrat, its final classification was Late, independently of the label given by the "New classifier 2". If it was classified as Poor by VeriStrat and the "New classifier 2" gave an EarlyEarly label, the final classification was Early. Finally, if the sample was classified Poor by VeriStrat and the classification given by "New classifier 2" was an EarlyLate label, the final classification was Late. FIG. 11 shows a flowchart that depicts the combination of the classification labels of VeriStrat with those of "New classifier 2".

In FIG. 20, Kaplan-Meier plots split by VeriStrat classification group (20A and 20C) and combination of VeriStrat with the "New classifier 2" (20B and 20D) are shown for the "nivolumab lung" cohort and the corresponding performance summaries are given in Table 23. Baseline characteristics and best response, also split by classification groups, are shown in Table 24.

TABLE 23

Summary of the performance of VeriStrat and the combination of VeriStrat with the "New classifier 2" on the "nivolumab lung" cohort

| | | OS HR (95% CI) | OS log-rank p | OS Median (Group1, Group2) | PFS HR (95% CI) | PFS log-rank p | PFS Median (Group1, Group2) |
|---|---|---|---|---|---|---|---|
| "NSCLC classifier" | VS Poor/ VS Good 29/69 | 0.37 (0.14-0.56) | 0.0003 | 136, not reached (days) | 0.55 (0.28-0.86) | 0.013 | 69, 154 (days) |
| Combination of VeriStrat with "New classifier 2" | #Early/#Late 19/79 | 0.27 (0.06-0.30) | <0.0001 | 105, not reached (days) | 0.42 (0.15-0.61) | 0.001 | 49, 154 (days) |

regulation of interferon-lambda 1 (or IL29) (UniProt: Q8IU54) in the EarlyEarly samples, as compared to Early-Late. This protein is an immunomodulator known to inhibit Type 2 immune response; hence its down-regulation in the Early/Early group should be associated with activation of the Type2 immune response in these patients and TH1 polarization of those patients' immune system.

TABLE 24

Baseline characteristics and best response by classification group for VeriStrat and for the combination of VeriStrat with the "New classifier 2" on nivolumab lung cohort.

| | | VeriStrat | | VeriStrat combined with "New classifier 2" | |
|---|---|---|---|---|---|
| | | VS Poor (N = 29) n (%) | VS Good (N = 69) n (%) | Early (N = 19) n (%) | Late (N = 79) n (%) |
| Gender | Male | 17 (59) | 34 (49) | 10 (53) | 41 (52) |
| | Female | 12 (41) | 35 (51) | 9 (47) | 38 (48) |
| Treatment Line | 2 | 19 (66) | 39 (57) | 12 (63) | 46 (58) |
| | 3 | 6 (21) | 25 (36) | 4 (21) | 27 (34) |
| | 4 | 3 (10) | 5 (7) | 2 (11) | 6 (8) |
| | 5 | 1 (3) | 0 (0) | 1 (5) | 0 (0) |
| Performance Status | 0 | 6 (21) | 14 (20) | 2 (11) | 18 (23) |
| | 1 | 16 (55) | 49 (71) | 11 (58) | 54 (68) |
| | 2 | 7 (24) | 6 (9) | 6 (32) | 7 (9) |
| Smoking Status | Current | 8 (28) | 15 (22) | 4 (21) | 19 (24) |
| | Former | 20 (69) | 45 (65) | 14 (74) | 51 (65) |
| | Never | 1 (3) | 7 (10) | 1 (5) | 7 (9) |
| | Unknown | 0 (0) | 2 (3) | 0 (0) | 2 (3) |
| Best response | CR | 0 (0) | 1 (1) | 0 (0) | 1 (1) |
| | PR | 6 (21) | 16 (23) | 3 (16) | 19 (24) |
| | SD | 8 (28) | 23 (33) | 6 (32) | 25 (32) |
| | PD | 11 (38) | 26 (38) | 8 (42) | 29 (37) |
| | NE | 4 (14) | 2 (3) | 2 (11) | 4 (5) |
| | NA | 0 (0) | 1 (1) | 0 (0) | 1 (1) |

Comparison with Chemotherapy Cohort for 2nd Line Patients

In FIG. 21, Kaplan-Meier plots split by VeriStrat classification group (21A and 21C) and combination of VeriStrat with the "New classifier 2" (21B and 21D) are shown for the patients in the "nivolumab lung" cohort that received 2nd line treatment. The curves are compared with those obtained for the PROSE cohort (docetaxel treatment in $2^{nd}$ line).

CONCLUSIONS

It has been shown that it is possible to create a classifier able to identify patients already assigned to poor prognosis subgroups who are likely to have durable benefit from immunotherapy. This classification may be associated with a type 2 immune response and is correlated with the down- It was necessary to adjust the cutoff used to extend the utility of the classifier developed for melanoma to the lung cancer setting.

Application of the classifier to the poor prognosis subgroup defined by other classifiers improved our ability to identify patients with very poor outcomes on immunotherapy. In particular, in the second line advanced lung cancer setting, we were able to identify subgroups of patients, by combination with VeriStrat or a new lung cancer immunotherapy test ("NSCLC classifier") with New classifier 2, that had especially poor outcomes when treated with nivolumab. Within those subgroups, outcomes on nivolumab did not show any superiority and were slightly inferior to standard docetaxel chemotherapy. This indicates the potential of the application of New classifier 2 in combination with the "NSCLC classifier" or VeriStrat to identify patients likely to have better or similar outcomes on docetaxel rather than a checkpoint inhibitor in second line treatment of NSCLC.

Given the poor outcomes of these subgroups of patients when treated with immunotherapy, it may be that these tests are suitable for the identification of the newly characterized clinical phenomenon of "hyperprogressive" disease (S Champiat et al, *Hyperprogressive disease* (*HPD*) *is a new pattern of progression in cancer patients treated by anti-PD-L1/PD-L*1, Clin Cancer Res 2016 Nov. 8 pii:clincacnerres. 1741.2016. [Epub ahead of print]).

Test Center

We further contemplate a laboratory test center for conducting tests on blood-based samples to see if the patient providing the sample is likely to obtain benefit from immunotherapy drugs, e.g. nivolumab. The lab test center is ideally configured as per Example 5 and FIG. 15 of the prior U.S. application Ser. No. 15/207,825 filed Jul. 12, 2016, and that description is incorporated by reference herein. The laboratory test center or system includes a mass spectrometer (e.g., MALDI time of flight) and a general purpose computer having a CPU implementing a classifier (or hierarchical arrangement of classifiers) coded as machine-readable instructions implanting a final classifier defined per FIG. 3, program code implementing a hierarchical classification procedure as per the Figures, and a memory storing reference mass spectral data set including a feature table of class-labeled mass spectrometry data from e.g., lung or melanoma patients used to develop the classifier per FIG. 3. This reference mass spectral data set forming the feature table will be understood to be the mass spectral data (integrated intensity values of predefined features, see Table 25) of a set of spectra which were used to generate the classifier.

Biological Interpretations

Biological interpretations of the tests of this disclosure and the mechanism's relation to good and poor prognosis on immunotherapy drugs, including generalizations to other cancer types, are set forth in Appendix B of our prior provisional application, and that discussion is incorporated by reference herein.

In brief, application of GSEA methods to protein data (PSEA) allows one to establish correlations between test classifications and biological processes and propose some hypotheses about possible mechanisms related to good and poor responses to immunotherapies. As explained in Appendix B of our prior provisional application, we propose the hypothesis that patients that are characterized by elevated acute-phase and complement processes (BDX008−) generally have inferior prognosis when treated with immunotherapies, however, they are not a uniform population, and some still may benefit from treatment, and those, who are also characterized by Type 2 immunity (Early/Early) have especially dismal prognosis. Specific factors resulting in this particular phenotype are difficult to elucidate, however the existing evidence points to multiple interactions between complement system, inflammation, and innate and adaptive immunity.

However, since the effects that are measured in serum reflect the state of the innate and adaptive immunity on the global level, not just at a tumor site, the classifiers of this disclosure are expected to be relevant for various cancers, and should not be restricted to melanoma. For the same reason it should be applicable for the broad variety of treatments affecting immunological status of the patient, such as various immune checkpoint inhibitors, high dose IL2, vaccines, and/or combinational therapy.

The appended claims are offered as further descriptions of the disclosed inventions

TABLE 25

| Feature Definitions | | |
|---|---|---|
| Left m/z | Center m/z | Right m/z |
| 3071.217 | 3085.189 | 3099.162 |
| 3099.644 | 3111.208 | 3122.771 |
| 3124.217 | 3144.212 | 3164.207 |
| 3192.341 | 3210.692 | 3229.043 |
| 3230.998 | 3243.532 | 3256.066 |
| 3296.707 | 3322.484 | 3348.261 |
| 3348.743 | 3363.679 | 3378.615 |
| 3379.097 | 3390.661 | 3402.224 |
| 3402.706 | 3418.124 | 3433.542 |
| 3434.506 | 3443.901 | 3453.297 |
| 3454.261 | 3462.933 | 3471.606 |
| 3486.542 | 3503.888 | 3521.233 |
| 3530.869 | 3553.033 | 3575.196 |
| 3583.137 | 3593.094 | 3603.051 |
| 3671.811 | 3682.716 | 3693.621 |
| 3694.825 | 3704.05 | 3713.275 |
| 3713.375 | 3723.478 | 3733.581 |
| 3759.25 | 3772.741 | 3786.232 |
| 3786.267 | 3795.511 | 3804.756 |
| 3805.438 | 3818.133 | 3830.828 |
| 3832.004 | 3841.641 | 3851.277 |
| 3877.777 | 3888.136 | 3898.495 |
| 3899.283 | 3907.43 | 3915.577 |
| 3915.701 | 3927.75 | 3939.799 |

TABLE 25-continued

| Feature Definitions | | |
|---|---|---|
| Left m/z | Center m/z | Right m/z |
| 3940.413 | 3952.458 | 3964.504 |
| 3995.34 | 4009.553 | 4023.767 |
| 4024.145 | 4031.508 | 4038.872 |
| 4039.254 | 4051.399 | 4063.544 |
| 4080.139 | 4094.835 | 4109.53 |
| 4112.173 | 4119.373 | 4126.573 |
| 4127.254 | 4133.389 | 4139.524 |
| 4165.916 | 4170.823 | 4175.73 |
| 4198.946 | 4210.815 | 4222.684 |
| 4252.63 | 4262.507 | 4272.384 |
| 4272.866 | 4287.802 | 4302.738 |
| 4322.975 | 4336.947 | 4350.92 |
| 4351.402 | 4359.834 | 4368.265 |
| 4369.229 | 4380.07 | 4390.911 |
| 4392.356 | 4408.979 | 4425.602 |
| 4426.151 | 4433.527 | 4440.903 |
| 4445.65 | 4462.521 | 4479.392 |
| 4493.056 | 4506.065 | 4519.074 |
| 4539.6 | 4546.345 | 4553.091 |
| 4553.295 | 4565.565 | 4577.835 |
| 4578.09 | 4590.487 | 4602.884 |
| 4610.619 | 4621.942 | 4633.264 |
| 4633.746 | 4642.419 | 4651.091 |
| 4668.351 | 4674.256 | 4680.16 |
| 4680.315 | 4686.375 | 4692.434 |
| 4694.454 | 4714.187 | 4733.919 |
| 4745.595 | 4755.26 | 4764.925 |
| 4767.31 | 4773.529 | 4779.749 |
| 4780.015 | 4789.426 | 4798.836 |
| 4801.9 | 4818.041 | 4834.181 |
| 4836.109 | 4856.827 | 4877.545 |
| 4878.027 | 4891.999 | 4905.972 |
| 4927.529 | 4935.668 | 4943.807 |
| 4948.646 | 4959.134 | 4969.622 |
| 4970.088 | 4977.701 | 4985.314 |
| 4986.713 | 4999.065 | 5011.417 |
| 5012.505 | 5022.06 | 5031.616 |
| 5033.636 | 5041.171 | 5048.707 |
| 5049.071 | 5067.139 | 5085.208 |
| 5087.135 | 5104.48 | 5121.826 |
| 5121.888 | 5127.87 | 5133.852 |
| 5134.353 | 5148.085 | 5161.816 |
| 5164.707 | 5176.994 | 5189.28 |
| 5211.228 | 5223.658 | 5236.088 |
| 5263.479 | 5288.052 | 5312.625 |
| 5330.753 | 5340.697 | 5350.642 |
| 5351.59 | 5362.357 | 5373.124 |
| 5395.675 | 5407.035 | 5418.395 |
| 5419.379 | 5428.197 | 5437.016 |
| 5442.725 | 5449.541 | 5456.357 |
| 5503.424 | 5519.324 | 5535.224 |
| 5537.824 | 5549.322 | 5560.82 |
| 5561.13 | 5570.453 | 5579.775 |
| 5666.474 | 5674.786 | 5683.099 |
| 5684.186 | 5691.955 | 5699.724 |
| 5699.879 | 5705.55 | 5711.222 |
| 5714.459 | 5720.241 | 5726.023 |
| 5726.029 | 5734.422 | 5742.814 |
| 5767.795 | 5777.164 | 5786.533 |
| 5803.887 | 5810.076 | 5816.265 |
| 5816.42 | 5822.763 | 5829.107 |
| 5832.023 | 5840.458 | 5848.894 |
| 5856.954 | 5868.25 | 5879.546 |
| 5879.588 | 5888.744 | 5897.9 |
| 5898.07 | 5909.769 | 5921.469 |
| 5923.788 | 5933.502 | 5943.215 |
| 5943.385 | 5952.758 | 5962.13 |
| 5973.586 | 5985.249 | 5996.913 |
| 5998.015 | 6008.576 | 6019.137 |
| 6019.872 | 6027.31 | 6034.749 |
| 6035.3 | 6042.831 | 6050.361 |
| 6067.076 | 6081.127 | 6095.178 |
| 6095.912 | 6108.218 | 6120.524 |
| 6186.655 | 6194.454 | 6202.254 |
| 6202.492 | 6209.862 | 6217.232 |

TABLE 25-continued

| Feature Definitions | | |
|---|---|---|
| Left m/z | Center m/z | Right m/z |
| 6217.504 | 6227.514 | 6237.524 |
| 6275.163 | 6284.15 | 6293.136 |
| 6293.984 | 6303.479 | 6312.974 |
| 6321.463 | 6332.667 | 6343.871 |
| 6346.716 | 6356.381 | 6366.045 |
| 6378.768 | 6393.095 | 6407.421 |
| 6407.605 | 6438.187 | 6468.768 |
| 6470.605 | 6487.319 | 6504.033 |
| 6521.115 | 6534.982 | 6548.849 |
| 6575.849 | 6589.257 | 6602.666 |
| 6603.584 | 6652.9 | 6702.216 |
| 6715.257 | 6730.594 | 6745.93 |
| 6798.461 | 6809.114 | 6819.767 |
| 6825.828 | 6837.675 | 6849.522 |
| 6849.889 | 6859.44 | 6868.991 |
| 6869.175 | 6890.297 | 6911.42 |
| 6911.603 | 6920.971 | 6930.338 |
| 6931.256 | 6947.144 | 6963.032 |
| 6963.583 | 6971.113 | 6978.644 |
| 6979.011 | 6995.266 | 7011.521 |
| 7012.072 | 7021.072 | 7030.072 |
| 7030.256 | 7035.123 | 7039.991 |
| 7040.358 | 7053.491 | 7066.623 |
| 7066.991 | 7075.623 | 7084.256 |
| 7118.235 | 7143.949 | 7169.664 |
| 7178.664 | 7189.317 | 7199.97 |
| 7231.745 | 7242.949 | 7254.153 |
| 7254.704 | 7269.031 | 7283.357 |
| 7283.908 | 7296.949 | 7309.99 |
| 7310.541 | 7341.306 | 7372.071 |
| 7375.194 | 7390.071 | 7404.949 |
| 7405.5 | 7418.632 | 7431.765 |
| 7433.234 | 7447.101 | 7460.969 |
| 7461.887 | 7471.622 | 7481.356 |
| 7524.336 | 7537.193 | 7550.05 |
| 7603.315 | 7617.366 | 7631.417 |
| 7639.922 | 7651.028 | 7662.134 |
| 7704.863 | 7713.35 | 7721.837 |
| 7729.987 | 7736.204 | 7742.42 |
| 7742.834 | 7750.915 | 7758.997 |
| 7760.24 | 7767.769 | 7775.297 |
| 7776.519 | 7788.917 | 7801.314 |
| 7811.174 | 7827.282 | 7843.39 |
| 7871.875 | 7881.201 | 7890.527 |
| 7905.09 | 7914.09 | 7923.09 |
| 7984.804 | 7994.906 | 8005.008 |
| 8006.661 | 8018.691 | 8030.722 |
| 8131.007 | 8153.048 | 8175.089 |
| 8192.538 | 8215.68 | 8238.823 |
| 8239.925 | 8254.895 | 8269.864 |
| 8307.149 | 8329.925 | 8352.7 |
| 8353.435 | 8364.455 | 8375.476 |
| 8378.598 | 8391.272 | 8403.945 |
| 8404.496 | 8413.955 | 8423.414 |
| 8423.598 | 8432.965 | 8442.333 |
| 8457.388 | 8464.68 | 8471.972 |
| 8472.104 | 8479.131 | 8486.157 |
| 8495.334 | 8507.712 | 8520.089 |
| 8520.598 | 8531.958 | 8543.319 |
| 8555.291 | 8565.118 | 8574.944 |
| 8575.312 | 8592.026 | 8608.74 |
| 8650.067 | 8661.913 | 8673.76 |
| 8719.855 | 8724.498 | 8729.142 |
| 8757.148 | 8771.291 | 8785.433 |
| 8800.495 | 8826.76 | 8853.025 |
| 8860.556 | 8871.76 | 8882.964 |
| 8883.698 | 8894.811 | 8905.923 |
| 8906.29 | 8932.096 | 8957.902 |
| 8966.168 | 8976.729 | 8987.29 |
| 8988.025 | 8998.678 | 9009.331 |
| 9009.882 | 9020.259 | 9030.637 |
| 9031.739 | 9041.657 | 9051.575 |
| 9056.496 | 9062.396 | 9068.296 |
| 9068.959 | 9078.57 | 9088.182 |
| 9089.963 | 9098.136 | 9106.31 |

TABLE 25-continued

| Feature Definitions | | |
|---|---|---|
| Left m/z | Center m/z | Right m/z |
| 9113.473 | 9142.493 | 9171.514 |
| 9196.31 | 9207.881 | 9219.452 |
| 9233.962 | 9244.34 | 9254.718 |
| 9254.901 | 9262.891 | 9270.881 |
| 9271.064 | 9281.258 | 9291.452 |
| 9308.35 | 9319.83 | 9331.309 |
| 9345.773 | 9366.207 | 9386.641 |
| 9387.1 | 9398.694 | 9410.288 |
| 9411.207 | 9454.025 | 9496.844 |
| 9554.472 | 9573.413 | 9592.354 |
| 9613.476 | 9626.563 | 9639.65 |
| 9640.109 | 9654.688 | 9669.267 |
| 9688.553 | 9723.565 | 9758.578 |
| 9779.012 | 9790.95 | 9802.889 |
| 9843.016 | 9866.062 | 9889.107 |
| 9903.45 | 9934.33 | 9965.21 |
| 10067.77 | 10077.87 | 10087.97 |
| 10088.18 | 10099.92 | 10111.66 |
| 10126.38 | 10138.78 | 10151.18 |
| 10151.41 | 10161.74 | 10172.07 |
| 10172.76 | 10184.81 | 10196.87 |
| 10200.08 | 10212.14 | 10224.19 |
| 10224.65 | 10236.01 | 10247.38 |
| 10249.52 | 10262.23 | 10274.94 |
| 10276.56 | 10285.67 | 10294.77 |
| 10295.62 | 10305.69 | 10315.75 |
| 10334.89 | 10347.33 | 10359.76 |
| 10435.64 | 10450.45 | 10465.26 |
| 10466.56 | 10476.95 | 10487.33 |
| 10499.93 | 10509.8 | 10519.67 |
| 10520.59 | 10535.4 | 10550.21 |
| 10570.41 | 10590.04 | 10609.67 |
| 10615.18 | 10638.37 | 10661.56 |
| 10662.02 | 10684.4 | 10706.79 |
| 10709.31 | 10734.45 | 10759.59 |
| 10761.75 | 10777.84 | 10793.93 |
| 10828.47 | 10847.99 | 10867.5 |
| 10874.06 | 10893.68 | 10913.3 |
| 10951.44 | 10963.37 | 10975.3 |
| 11028.77 | 11056.4 | 11084.03 |
| 11090.89 | 11107.43 | 11123.96 |
| 11132.45 | 11152.43 | 11172.4 |
| 11235.82 | 11305.1 | 11324.39 |
| 11377.88 | 11389.94 | 11401.99 |
| 11402.35 | 11414.43 | 11426.5 |
| 11428.16 | 11442.74 | 11457.32 |
| 11464.41 | 11477.66 | 11490.9 |
| 11491.24 | 11501.47 | 11511.7 |
| 11513.71 | 11530.99 | 11548.26 |
| 11563.85 | 11577.63 | 11591.4 |
| 11613 | 11626.92 | 11640.84 |
| 11643.86 | 11657.11 | 11670.36 |
| 11670.69 | 11686.46 | 11702.22 |
| 11719.74 | 11732.72 | 11745.69 |
| 11746.38 | 11756.13 | 11765.89 |
| 11769.8 | 11786.1 | 11802.4 |
| 11822.14 | 11835.46 | 11848.77 |
| 11867.09 | 11883.39 | 11899.68 |
| 11900.2 | 11913.4 | 11926.61 |
| 11927.82 | 11938.26 | 11948.69 |
| 11949.11 | 11964.95 | 11980.79 |
| 11980.83 | 12004.32 | 12027.8 |
| 12064.36 | 12080.32 | 12096.27 |
| 12266.86 | 12290.16 | 12313.47 |
| 12436.99 | 12459.03 | 12481.07 |
| 12546.5 | 12573.59 | 12600.69 |
| 12601.37 | 12615.26 | 12629.15 |
| 12661.3 | 12674.73 | 12688.16 |
| 12723.06 | 12738.33 | 12753.59 |
| 12769.89 | 12789.06 | 12808.24 |
| 12830.74 | 12870.91 | 12911.09 |
| 12937.95 | 12962.98 | 12988.01 |
| 13049.54 | 13076.86 | 13104.18 |
| 13119.56 | 13135.29 | 13151.02 |
| 13259.38 | 13273.73 | 13288.08 |

TABLE 25-continued

| Feature Definitions | | |
|---|---|---|
| Left m/z | Center m/z | Right m/z |
| 13304.84 | 13325.96 | 13347.09 |
| 13349.01 | 13365.97 | 13382.93 |
| 13510.31 | 13524.23 | 13538.16 |
| 13598.03 | 13619.61 | 13641.19 |
| 13700.43 | 13720.06 | 13739.69 |
| 13739.92 | 13781.47 | 13823.03 |
| 13826.35 | 13845.18 | 13864.02 |
| 13864.91 | 13894.51 | 13924.11 |
| 13925.45 | 13942.27 | 13959.08 |
| 13959.98 | 13981.28 | 14002.58 |
| 14008.41 | 14042.49 | 14076.57 |
| 14077.02 | 14099.66 | 14122.31 |
| 14124.55 | 14152.13 | 14179.7 |
| 14180.6 | 14204.59 | 14228.58 |
| 14229.93 | 14254.82 | 14279.7 |
| 14280.6 | 14301.9 | 14323.2 |
| 14412.88 | 14435.3 | 14457.73 |
| 14464.45 | 14489.34 | 14514.23 |
| 14516.47 | 14543.37 | 14570.28 |
| 14571.18 | 14594.72 | 14618.26 |
| 14707.6 | 14727.24 | 14746.88 |
| 14764.89 | 14786.87 | 14808.84 |
| 14859.96 | 14882.15 | 14904.35 |
| 14951.88 | 14980.13 | 15008.38 |
| 15519.58 | 15560.39 | 15601.2 |
| 15717.5 | 15751.16 | 15784.83 |
| 16261.72 | 16302.97 | 16344.23 |
| 16447.74 | 16504.38 | 16561.02 |
| 16607.55 | 16625.96 | 16644.36 |
| 17771.55 | 17809.44 | 17847.33 |
| 17971.11 | 17996.07 | 18021.03 |
| 18021.82 | 18048.07 | 18074.32 |
| 18248.22 | 18280.06 | 18311.89 |
| 18594.4 | 18638.57 | 18682.74 |
| 18811.43 | 18848.65 | 18885.87 |
| 19822.65 | 19999.45 | 20176.24 |
| 20808.15 | 20831.29 | 20854.43 |
| 20873.86 | 20939.16 | 21004.45 |
| 21006.87 | 21065.87 | 21124.88 |
| 21125.85 | 21173.49 | 21221.13 |
| 21221.61 | 21272.15 | 21322.7 |
| 21323.18 | 21373.24 | 21423.3 |
| 21636.47 | 21786.47 | 21936.48 |
| 22991.54 | 23049.38 | 23107.22 |
| 23107.99 | 23155.81 | 23203.63 |
| 23205.94 | 23266.87 | 23327.8 |
| 23404.15 | 23469.71 | 23535.26 |
| 27895.09 | 27945.61 | 27996.12 |
| 27999.21 | 28074.02 | 28148.83 |

The invention claimed is:

1. A method of treating a lung cancer patient, a renal cell carcinoma patient, or a melanoma patient with an immunotherapy drug comprising:

(a) conducting a mass spectrometer test on a blood-based sample of the cancer patient to obtain a mass spectrum comprising integrated intensity values of selected features in the mass spectrum at one or more m/z ranges from a multitude of mass-spectral features listed in a table below:

| Feature Definitions | | |
|---|---|---|
| Left m/z | Center m/z | Right m/z |
| 3071.217 | 3085.189 | 3099.162 |
| 3099.644 | 3111.208 | 3122.771 |
| 3124.217 | 3144.212 | 3164.207 |
| 3192.341 | 3210.692 | 3229.043 |
| 3230.998 | 3243.532 | 3256.066 |
| 3296.707 | 3322.484 | 3348.261 |
| 3348.743 | 3363.679 | 3378.615 |
| 3379.097 | 3390.661 | 3402.224 |
| 3402.706 | 3418.124 | 3433.542 |
| 3434.506 | 3443.901 | 3453.297 |
| 3454.261 | 3462.933 | 3471.606 |
| 3486.542 | 3503.888 | 3521.233 |
| 3530.869 | 3553.033 | 3575.196 |
| 3583.137 | 3593.094 | 3603.051 |
| 3671.811 | 3682.716 | 3693.621 |
| 3694.825 | 3704.05 | 3713.275 |
| 3713.375 | 3723.478 | 3733.581 |
| 3759.25 | 3772.741 | 3786.232 |
| 3786.267 | 3795.511 | 3804.756 |
| 3805.438 | 3818.133 | 3830.828 |
| 3832.004 | 3841.641 | 3851.277 |
| 3877.777 | 3888.136 | 3898.495 |
| 3899.283 | 3907.43 | 3915.577 |
| 3915.701 | 3927.75 | 3939.799 |
| 3940.413 | 3952.458 | 3964.504 |
| 3995.34 | 4009.553 | 4023.767 |
| 4024.145 | 4031.508 | 4038.872 |
| 4039.254 | 4051.399 | 4063.544 |
| 4080.139 | 4094.835 | 4109.53 |
| 4112.173 | 4119.373 | 4126.573 |
| 4127.254 | 4133.389 | 4139.524 |
| 4165.916 | 4170.823 | 4175.73 |
| 4198.946 | 4210.815 | 4222.684 |
| 4252.63 | 4262.507 | 4272.384 |
| 4272.866 | 4287.802 | 4302.738 |
| 4322.975 | 4336.947 | 4350.92 |
| 4351.402 | 4359.834 | 4368.265 |
| 4369.229 | 4380.07 | 4390.911 |
| 4392.356 | 4408.979 | 4425.602 |
| 4426.151 | 4433.527 | 4440.903 |
| 4445.65 | 4462.521 | 4479.392 |
| 4493.056 | 4506.065 | 4519.074 |
| 4539.6 | 4546.345 | 4553.091 |
| 4553.295 | 4565.565 | 4577.835 |
| 4578.09 | 4590.487 | 4602.884 |
| 4610.619 | 4621.942 | 4633.264 |
| 4633.746 | 4642.419 | 4651.091 |
| 4668.351 | 4674.256 | 4680.16 |
| 4680.315 | 4686.375 | 4692.434 |
| 4694.454 | 4714.187 | 4733.919 |
| 4745.595 | 4755.26 | 4764.925 |
| 4767.31 | 4773.529 | 4779.749 |
| 4780.015 | 4789.426 | 4798.836 |
| 4801.9 | 4818.041 | 4834.181 |
| 4836.109 | 4856.827 | 4877.545 |
| 4878.027 | 4891.999 | 4905.972 |
| 4927.529 | 4935.668 | 4943.807 |
| 4948.646 | 4959.134 | 4969.622 |
| 4970.088 | 4977.701 | 4985.314 |
| 4986.713 | 4999.065 | 5011.417 |
| 5012.505 | 5022.06 | 5031.616 |
| 5033.636 | 5041.171 | 5048.707 |
| 5049.071 | 5067.139 | 5085.208 |
| 5087.135 | 5104.48 | 5121.826 |
| 5121.888 | 5127.87 | 5133.852 |
| 5134.353 | 5148.085 | 5161.816 |
| 5164.707 | 5176.994 | 5189.28 |
| 5211.228 | 5223.658 | 5236.088 |
| 5263.479 | 5288.052 | 5312.625 |
| 5330.753 | 5340.697 | 5350.642 |
| 5351.59 | 5362.357 | 5373.124 |
| 5395.675 | 5407.035 | 5418.395 |
| 5419.379 | 5428.197 | 5437.016 |
| 5442.725 | 5449.541 | 5456.357 |
| 5503.424 | 5519.324 | 5535.224 |
| 5537.824 | 5549.322 | 5560.82 |
| 5561.13 | 5570.453 | 5579.775 |
| 5666.474 | 5674.786 | 5683.099 |
| 5684.186 | 5691.955 | 5699.724 |
| 5699.879 | 5705.55 | 5711.222 |

| Feature Definitions | | |
|---|---|---|
| Left m/z | Center m/z | Right m/z |
| 5714.459 | 5720.241 | 5726.023 |
| 5726.029 | 5734.422 | 5742.814 |
| 5767.795 | 5777.164 | 5786.533 |
| 5803.887 | 5810.076 | 5816.265 |
| 5816.42 | 5822.763 | 5829.107 |
| 5832.023 | 5840.458 | 5848.894 |
| 5856.954 | 5868.25 | 5879.546 |
| 5879.588 | 5888.744 | 5897.9 |
| 5898.07 | 5909.769 | 5921.469 |
| 5923.788 | 5933.502 | 5943.215 |
| 5943.385 | 5952.758 | 5962.13 |
| 5973.586 | 5985.249 | 5996.913 |
| 5998.015 | 6008.576 | 6019.137 |
| 6019.872 | 6027.31 | 6034.749 |
| 6035.3 | 6042.831 | 6050.361 |
| 6067.076 | 6081.127 | 6095.178 |
| 6095.912 | 6108.218 | 6120.524 |
| 6186.655 | 6194.454 | 6202.254 |
| 6202.492 | 6209.862 | 6217.232 |
| 6217.504 | 6227.514 | 6237.524 |
| 6275.163 | 6284.15 | 6293.136 |
| 6293.984 | 6303.479 | 6312.974 |
| 6321.463 | 6332.667 | 6343.871 |
| 6346.716 | 6356.381 | 6366.045 |
| 6378.768 | 6393.095 | 6407.421 |
| 6407.605 | 6438.187 | 6468.768 |
| 6470.605 | 6487.319 | 6504.033 |
| 6521.115 | 6534.982 | 6548.849 |
| 6575.849 | 6589.257 | 6602.666 |
| 6603.584 | 6652.9 | 6702.216 |
| 6715.257 | 6730.594 | 6745.93 |
| 6798.461 | 6809.114 | 6819.767 |
| 6825.828 | 6837.675 | 6849.522 |
| 6849.889 | 6859.44 | 6868.991 |
| 6869.175 | 6890.297 | 6911.42 |
| 6911.603 | 6920.971 | 6930.338 |
| 6931.256 | 6947.144 | 6963.032 |
| 6963.583 | 6971.113 | 6978.644 |
| 6979.011 | 6995.266 | 7011.521 |
| 7012.072 | 7021.072 | 7030.072 |
| 7030.256 | 7035.123 | 7039.991 |
| 7040.358 | 7053.491 | 7066.623 |
| 7066.991 | 7075.623 | 7084.256 |
| 7118.235 | 7143.949 | 7169.664 |
| 7178.664 | 7189.317 | 7199.97 |
| 7231.745 | 7242.949 | 7254.153 |
| 7254.704 | 7269.031 | 7283.357 |
| 7283.908 | 7296.949 | 7309.99 |
| 7310.541 | 7341.306 | 7372.071 |
| 7375.194 | 7390.071 | 7404.949 |
| 7405.5 | 7418.632 | 7431.765 |
| 7433.234 | 7447.101 | 7460.969 |
| 7461.887 | 7471.622 | 7481.356 |
| 7524.336 | 7537.193 | 7550.05 |
| 7603.315 | 7617.366 | 7631.417 |
| 7639.922 | 7651.028 | 7662.134 |
| 7704.863 | 7713.35 | 7721.837 |
| 7729.987 | 7736.204 | 7742.42 |
| 7742.834 | 7750.915 | 7758.997 |
| 7760.24 | 7767.769 | 7775.297 |
| 7776.519 | 7788.917 | 7801.314 |
| 7811.174 | 7827.282 | 7843.39 |
| 7871.875 | 7881.201 | 7890.527 |
| 7905.09 | 7914.09 | 7923.09 |
| 7984.804 | 7994.906 | 8005.008 |
| 8006.661 | 8018.691 | 8030.722 |
| 8131.007 | 8153.048 | 8175.089 |
| 8192.538 | 8215.68 | 8238.823 |
| 8239.925 | 8254.895 | 8269.864 |
| 8307.149 | 8329.925 | 8352.7 |
| 8353.435 | 8364.455 | 8375.476 |
| 8378.598 | 8391.272 | 8403.945 |
| 8404.496 | 8413.955 | 8423.414 |
| 8423.598 | 8432.965 | 8442.333 |
| 8457.388 | 8464.68 | 8471.972 |

| Feature Definitions | | |
|---|---|---|
| Left m/z | Center m/z | Right m/z |
| 8472.104 | 8479.131 | 8486.157 |
| 8495.334 | 8507.712 | 8520.089 |
| 8520.598 | 8531.958 | 8543.319 |
| 8555.291 | 8565.118 | 8574.944 |
| 8575.312 | 8592.026 | 8608.74 |
| 8650.067 | 8661.913 | 8673.76 |
| 8719.855 | 8724.498 | 8729.142 |
| 8757.148 | 8771.291 | 8785.433 |
| 8800.495 | 8826.76 | 8853.025 |
| 8860.556 | 8871.76 | 8882.964 |
| 8883.698 | 8894.811 | 8905.923 |
| 8906.29 | 8932.096 | 8957.902 |
| 8966.168 | 8976.729 | 8987.29 |
| 8988.025 | 8998.678 | 9009.331 |
| 9009.882 | 9020.259 | 9030.637 |
| 9031.739 | 9041.657 | 9051.575 |
| 9056.496 | 9062.396 | 9068.296 |
| 9068.959 | 9078.57 | 9088.182 |
| 9089.963 | 9098.136 | 9106.31 |
| 9113.473 | 9142.493 | 9171.514 |
| 9196.31 | 9207.881 | 9219.452 |
| 9233.962 | 9244.34 | 9254.718 |
| 9254.901 | 9262.891 | 9270.881 |
| 9271.064 | 9281.258 | 9291.452 |
| 9308.35 | 9319.83 | 9331.309 |
| 9345.773 | 9366.207 | 9386.641 |
| 9387.1 | 9398.694 | 9410.288 |
| 9411.207 | 9454.025 | 9496.844 |
| 9554.472 | 9573.413 | 9592.354 |
| 9613.476 | 9626.563 | 9639.65 |
| 9640.109 | 9654.688 | 9669.267 |
| 9688.553 | 9723.565 | 9758.578 |
| 9779.012 | 9790.95 | 9802.889 |
| 9843.016 | 9866.062 | 9889.107 |
| 9903.45 | 9934.33 | 9965.21 |
| 10067.77 | 10077.87 | 10087.97 |
| 10088.18 | 10099.92 | 10111.66 |
| 10126.38 | 10138.78 | 10151.18 |
| 10151.41 | 10161.74 | 10172.07 |
| 10172.76 | 10184.81 | 10196.87 |
| 10200.08 | 10212.14 | 10224.19 |
| 10224.65 | 10236.01 | 10247.38 |
| 10249.52 | 10262.23 | 10274.94 |
| 10276.56 | 10285.67 | 10294.77 |
| 10295.62 | 10305.69 | 10315.75 |
| 10334.89 | 10347.33 | 10359.76 |
| 10435.64 | 10450.45 | 10465.26 |
| 10466.56 | 10476.95 | 10487.33 |
| 10499.93 | 10509.8 | 10519.67 |
| 10520.59 | 10535.4 | 10550.21 |
| 10570.41 | 10590.04 | 10609.67 |
| 10615.18 | 10638.37 | 10661.56 |
| 10662.02 | 10684.4 | 10706.79 |
| 10709.31 | 10734.45 | 10759.59 |
| 10761.75 | 10777.84 | 10793.93 |
| 10828.47 | 10847.99 | 10867.5 |
| 10874.06 | 10893.68 | 10913.3 |
| 10951.44 | 10963.37 | 10975.3 |
| 11028.77 | 11056.4 | 11084.03 |
| 11090.89 | 11107.43 | 11123.96 |
| 11132.45 | 11152.43 | 11172.4 |
| 11285.82 | 11305.1 | 11324.39 |
| 11377.88 | 11389.94 | 11401.99 |
| 11402.35 | 11414.43 | 11426.5 |
| 11428.16 | 11442.74 | 11457.32 |
| 11464.41 | 11477.66 | 11490.9 |
| 11491.24 | 11501.47 | 11511.7 |
| 11513.71 | 11530.99 | 11548.26 |
| 11563.85 | 11577.63 | 11591.4 |
| 11613 | 11626.92 | 11640.84 |
| 11643.86 | 11657.11 | 11670.36 |
| 11670.69 | 11686.46 | 11702.22 |
| 11719.74 | 11732.72 | 11745.69 |
| 11746.38 | 11756.13 | 11765.89 |
| 11769.8 | 11786.1 | 11802.4 |

-continued

| Feature Definitions | | |
|---|---|---|
| Left m/z | Center m/z | Right m/z |
| 11822.14 | 11835.46 | 11848.77 |
| 11867.09 | 11883.39 | 11899.68 |
| 11900.2 | 11913.4 | 11926.61 |
| 11927.82 | 11938.26 | 11948.69 |
| 11949.11 | 11964.95 | 11980.79 |
| 11980.83 | 12004.32 | 12027.8 |
| 12064.36 | 12080.32 | 12096.27 |
| 12266.86 | 12290.16 | 12313.47 |
| 12436.99 | 12459.03 | 12481.07 |
| 12546.5 | 12573.59 | 12600.69 |
| 12601.37 | 12615.26 | 12629.15 |
| 12661.3 | 12674.73 | 12688.16 |
| 12723.06 | 12738.33 | 12753.59 |
| 12769.89 | 12789.06 | 12808.24 |
| 12830.74 | 12870.91 | 12911.09 |
| 12937.95 | 12962.98 | 12988.01 |
| 13049.54 | 13076.86 | 13104.18 |
| 13119.56 | 13135.29 | 13151.02 |
| 13259.38 | 13273.73 | 13288.08 |
| 13304.84 | 13325.96 | 13347.09 |
| 13349.01 | 13365.97 | 13382.93 |
| 13510.31 | 13524.23 | 13538.16 |
| 13598.03 | 13619.61 | 13641.19 |
| 13700.43 | 13720.06 | 13739.69 |
| 13739.92 | 13781.47 | 13823.03 |
| 13826.35 | 13845.18 | 13864.02 |
| 13864.91 | 13894.51 | 13924.11 |
| 13925.45 | 13942.27 | 13959.08 |
| 13959.98 | 13981.28 | 14002.58 |
| 14008.41 | 14042.49 | 14076.57 |
| 14077.02 | 14099.66 | 14122.31 |
| 14124.55 | 14152.13 | 14179.7 |
| 14180.6 | 14204.59 | 14228.58 |
| 14229.93 | 14254.82 | 14279.7 |
| 14280.6 | 14301.9 | 14323.2 |
| 14412.88 | 14435.3 | 14457.73 |
| 14464.45 | 14489.34 | 14514.23 |
| 14516.47 | 14543.37 | 14570.28 |
| 14571.18 | 14594.72 | 14618.26 |
| 14707.6 | 14727.24 | 14746.88 |
| 14764.89 | 14786.87 | 14808.84 |
| 14859.96 | 14882.15 | 14904.35 |
| 14951.88 | 14980.13 | 15008.38 |
| 15519.58 | 15560.39 | 15601.2 |
| 15717.5 | 15751.16 | 15784.83 |
| 16261.72 | 16302.97 | 16344.23 |
| 16447.74 | 16504.38 | 16561.02 |
| 16607.55 | 16625.96 | 16644.36 |
| 17771.55 | 17809.44 | 17847.33 |
| 17971.11 | 17996.07 | 18021.03 |
| 18021.82 | 18048.07 | 18074.32 |
| 18248.22 | 18280.06 | 18311.89 |
| 18594.4 | 18638.57 | 18682.74 |
| 18811.43 | 18848.65 | 18885.87 |
| 19822.65 | 19999.45 | 20176.24 |
| 20808.15 | 20831.29 | 20854.43 |
| 20873.86 | 20939.16 | 21004.45 |
| 21006.87 | 21065.87 | 21124.88 |
| 21125.85 | 21173.49 | 21221.13 |
| 21221.61 | 21272.15 | 21322.7 |
| 21323.18 | 21373.24 | 21423.3 |
| 21636.47 | 21786.47 | 21936.48 |
| 22991.54 | 23049.38 | 23107.22 |
| 23107.99 | 23155.81 | 23203.63 |
| 23205.94 | 23266.87 | 23327.8 |
| 23404.15 | 23469.71 | 23535.26 |
| 27895.09 | 27945.61 | 27996.12 |
| 27999.21 | 28074.02 | 28148.83 |

wherein the mass spectrometer test is conducted using a mass spectrometer and wherein the integrated intensity values are processed in a first stage classification algorithm using a training set comprising class-labeled spectra produced from blood-based samples from the same type of cancer patients to identify the patient as being in a class of patients determined to be a poor prognosis subgroup corresponding to a class label for the blood-based sample, and (b) responsive to identification of the cancer patient as being in the class of patients determined to be a poor prognosis subgroup, processing data from the mass spectrometer test with a programmed computer implementing a second stage classification algorithm, wherein the programmed computer compares the integrated intensity values with feature values of a reference set of class-labeled mass spectral data obtained from blood-based samples from a multitude of patients having the same type of cancer treated with an immunotherapy drug and revising the class label for the blood-based sample; and (c) administering the immunotherapy drug to the cancer patient.

2. The method of claim 1, wherein the immunotherapy drug comprises an antibody drug blocking ligand activation of a PD-1 checkpoint protein, anti-CTLA4 drugs, high dose interleukin-2, and combination therapies.

3. The method of claim 1, wherein the immunotherapy drug comprises a combination of two immunotherapy drugs.

4. A method of treating a lung cancer patient, a renal cell carcinoma patient, or a melanoma patient with an immunotherapy drug comprising the steps of:

(a) conducting a mass spectrometer test on a blood-based sample of the cancer patient to obtain a mass spectrum comprising integrated intensity values of selected features in the mass spectrum at one or more m/z ranges as shown in a table below:

| Feature Definitions | | |
|---|---|---|
| Left m/z | Center m/z | Right m/z |
| 3071.217 | 3085.189 | 3099.162 |
| 3099.644 | 3111.208 | 3122.771 |
| 3124.217 | 3144.212 | 3164.207 |
| 3192.341 | 3210.692 | 3229.043 |
| 3230.998 | 3243.532 | 3256.066 |
| 3296.707 | 3322.484 | 3348.261 |
| 3348.743 | 3363.679 | 3378.615 |
| 3379.097 | 3390.661 | 3402.224 |
| 3402.706 | 3418.124 | 3433.542 |
| 3434.506 | 3443.901 | 3453.297 |
| 3454.261 | 3462.933 | 3471.606 |
| 3486.542 | 3503.888 | 3521.233 |
| 3530.869 | 3553.033 | 3575.196 |
| 3583.137 | 3593.094 | 3603.051 |
| 3671.811 | 3682.716 | 3693.621 |
| 3694.825 | 3704.05 | 3713.275 |
| 3713.375 | 3723.478 | 3733.581 |
| 3759.25 | 3772.741 | 3786.232 |
| 3786.267 | 3795.511 | 3804.756 |
| 3805.438 | 3818.133 | 3830.828 |
| 3832.004 | 3841.641 | 3851.277 |
| 3877.777 | 3888.136 | 3898.495 |
| 3899.283 | 3907.43 | 3915.577 |
| 3915.701 | 3927.75 | 3939.799 |
| 3940.413 | 3952.458 | 3964.504 |
| 3995.34 | 4009.553 | 4023.767 |
| 4024.145 | 4031.508 | 4038.872 |
| 4039.254 | 4051.399 | 4063.544 |
| 4080.139 | 4094.835 | 4109.53 |
| 4112.173 | 4119.373 | 4126.573 |
| 4127.254 | 4133.389 | 4139.524 |
| 4165.916 | 4170.823 | 4175.73 |
| 4198.946 | 4210.815 | 4222.684 |
| 4252.63 | 4262.507 | 4272.384 |
| 4272.866 | 4287.802 | 4302.738 |
| 4322.975 | 4336.947 | 4350.92 |
| 4351.402 | 4359.834 | 4368.265 |

-continued

| Feature Definitions | | |
|---|---|---|
| Left m/z | Center m/z | Right m/z |
| 4369.229 | 4380.07 | 4390.911 |
| 4392.356 | 4408.979 | 4425.602 |
| 4426.151 | 4433.527 | 4440.903 |
| 4445.65 | 4462.521 | 4479.392 |
| 4493.056 | 4506.065 | 4519.074 |
| 4539.6 | 4546.345 | 4553.091 |
| 4553.295 | 4565.565 | 4577.835 |
| 4578.09 | 4590.487 | 4602.884 |
| 4610.619 | 4621.942 | 4633.264 |
| 4633.746 | 4642.419 | 4651.091 |
| 4668.351 | 4674.256 | 4680.16 |
| 4680.315 | 4686.375 | 4692.434 |
| 4694.454 | 4714.187 | 4733.919 |
| 4745.595 | 4755.26 | 4764.925 |
| 4767.31 | 4773.529 | 4779.749 |
| 4780.015 | 4789.426 | 4798.836 |
| 4801.9 | 4818.041 | 4834.181 |
| 4836.109 | 4856.827 | 4877.545 |
| 4878.027 | 4891.999 | 4905.972 |
| 4927.529 | 4935.668 | 4943.807 |
| 4948.646 | 4959.134 | 4969.622 |
| 4970.088 | 4977.701 | 4985.314 |
| 4986.713 | 4999.065 | 5011.417 |
| 5012.505 | 5022.06 | 5031.616 |
| 5033.636 | 5041.171 | 5048.707 |
| 5049.071 | 5067.139 | 5085.208 |
| 5087.135 | 5104.48 | 5121.826 |
| 5121.888 | 5127.87 | 5133.852 |
| 5134.353 | 5148.085 | 5161.816 |
| 5164.707 | 5176.994 | 5189.28 |
| 5211.228 | 5223.658 | 5236.088 |
| 5263.479 | 5288.052 | 5312.625 |
| 5330.753 | 5340.697 | 5350.642 |
| 5351.59 | 5362.357 | 5373.124 |
| 5395.675 | 5407.035 | 5418.395 |
| 5419.379 | 5428.197 | 5437.016 |
| 5442.725 | 5449.541 | 5456.357 |
| 5503.424 | 5519.324 | 5535.224 |
| 5537.824 | 5549.322 | 5560.82 |
| 5561.13 | 5570.453 | 5579.775 |
| 5666.474 | 5674.786 | 5683.099 |
| 5684.186 | 5691.955 | 5699.724 |
| 5699.879 | 5705.55 | 5711.222 |
| 5714.459 | 5720.241 | 5726.023 |
| 5726.029 | 5734.422 | 5742.814 |
| 5767.795 | 5777.164 | 5786.533 |
| 5803.887 | 5810.076 | 5816.265 |
| 5816.42 | 5822.763 | 5829.107 |
| 5832.023 | 5840.458 | 5848.894 |
| 5856.954 | 5868.25 | 5879.546 |
| 5879.588 | 5888.744 | 5897.9 |
| 5898.07 | 5909.769 | 5921.469 |
| 5923.788 | 5933.502 | 5943.215 |
| 5943.385 | 5952.758 | 5962.13 |
| 5973.586 | 5985.249 | 5996.913 |
| 5998.015 | 6008.576 | 6019.137 |
| 6019.872 | 6027.31 | 6034.749 |
| 6035.3 | 6042.831 | 6050.361 |
| 6067.076 | 6081.127 | 6095.178 |
| 6095.912 | 6108.218 | 6120.524 |
| 6186.655 | 6194.454 | 6202.254 |
| 6202.492 | 6209.862 | 6217.232 |
| 6217.504 | 6227.514 | 6237.524 |
| 6275.163 | 6284.15 | 6293.136 |
| 6293.984 | 6303.479 | 6312.974 |
| 6321.463 | 6332.667 | 6343.871 |
| 6346.716 | 6356.381 | 6366.045 |
| 6378.768 | 6393.095 | 6407.421 |
| 6407.605 | 6438.187 | 6468.768 |
| 6470.605 | 6487.319 | 6504.033 |
| 6521.115 | 6534.982 | 6548.849 |
| 6575.849 | 6589.257 | 6602.666 |
| 6603.584 | 6652.9 | 6702.216 |
| 6715.257 | 6730.594 | 6745.93 |
| 6798.461 | 6809.114 | 6819.767 |

-continued

| Feature Definitions | | |
|---|---|---|
| Left m/z | Center m/z | Right m/z |
| 6825.828 | 6837.675 | 6849.522 |
| 6849.889 | 6859.44 | 6868.991 |
| 6869.175 | 6890.297 | 6911.42 |
| 6911.603 | 6920.971 | 6930.338 |
| 6931.256 | 6947.144 | 6963.032 |
| 6963.583 | 6971.113 | 6978.644 |
| 6979.011 | 6995.266 | 7011.521 |
| 7012.072 | 7021.072 | 7030.072 |
| 7030.256 | 7035.123 | 7039.991 |
| 7040.358 | 7053.491 | 7066.623 |
| 7066.991 | 7075.623 | 7084.256 |
| 7118.235 | 7143.949 | 7169.664 |
| 7178.664 | 7189.317 | 7199.97 |
| 7231.745 | 7242.949 | 7254.153 |
| 7254.704 | 7269.031 | 7283.357 |
| 7283.908 | 7296.949 | 7309.99 |
| 7310.541 | 7341.306 | 7372.071 |
| 7375.194 | 7390.071 | 7404.949 |
| 7405.5 | 7418.632 | 7431.765 |
| 7433.234 | 7447.101 | 7460.969 |
| 7461.887 | 7471.622 | 7481.356 |
| 7524.336 | 7537.193 | 7550.05 |
| 7603.315 | 7617.366 | 7631.417 |
| 7639.922 | 7651.028 | 7662.134 |
| 7704.863 | 7713.35 | 7721.837 |
| 7729.987 | 7736.204 | 7742.42 |
| 7742.834 | 7750.915 | 7758.997 |
| 7760.24 | 7767.769 | 7775.297 |
| 7776.519 | 7788.917 | 7801.314 |
| 7811.174 | 7827.282 | 7843.39 |
| 7871.875 | 7881.201 | 7890.527 |
| 7905.09 | 7914.09 | 7923.09 |
| 7984.804 | 7994.906 | 8005.008 |
| 8006.661 | 8018.691 | 8030.722 |
| 8131.007 | 8153.048 | 8175.089 |
| 8192.538 | 8215.68 | 8238.823 |
| 8239.925 | 8254.895 | 8269.864 |
| 8307.149 | 8329.925 | 8352.7 |
| 8353.435 | 8364.455 | 8375.476 |
| 8378.598 | 8391.272 | 8403.945 |
| 8404.496 | 8413.955 | 8423.414 |
| 8423.598 | 8432.965 | 8442.333 |
| 8457.388 | 8464.68 | 8471.972 |
| 8472.104 | 8479.131 | 8486.157 |
| 8495.334 | 8507.712 | 8520.089 |
| 8520.598 | 8531.958 | 8543.319 |
| 8555.291 | 8565.118 | 8574.944 |
| 8575.312 | 8592.026 | 8608.74 |
| 8650.067 | 8661.913 | 8673.76 |
| 8719.855 | 8724.498 | 8729.142 |
| 8757.148 | 8771.291 | 8785.433 |
| 8800.495 | 8826.76 | 8853.025 |
| 8860.556 | 8871.76 | 8882.964 |
| 8883.698 | 8894.811 | 8905.923 |
| 8906.29 | 8932.096 | 8957.902 |
| 8966.168 | 8976.729 | 8987.29 |
| 8988.025 | 8998.678 | 9009.331 |
| 9009.882 | 9020.259 | 9030.637 |
| 9031.739 | 9041.657 | 9051.575 |
| 9056.496 | 9062.396 | 9068.296 |
| 9068.959 | 9078.57 | 9088.182 |
| 9089.963 | 9098.136 | 9106.31 |
| 9113.473 | 9142.493 | 9171.514 |
| 9196.31 | 9207.881 | 9219.452 |
| 9233.962 | 9244.34 | 9254.718 |
| 9254.901 | 9262.891 | 9270.881 |
| 9271.064 | 9281.258 | 9291.452 |
| 9308.35 | 9319.83 | 9331.309 |
| 9345.773 | 9366.207 | 9386.641 |
| 9387.1 | 9398.694 | 9410.288 |
| 9411.207 | 9454.025 | 9496.844 |
| 9554.472 | 9573.413 | 9592.354 |
| 9613.476 | 9626.563 | 9639.65 |
| 9640.109 | 9654.688 | 9669.267 |
| 9688.553 | 9723.565 | 9758.578 |

-continued

| Feature Definitions | | |
|---|---|---|
| Left m/z | Center m/z | Right m/z |
| 9779.012 | 9790.95 | 9802.889 |
| 9843.016 | 9866.062 | 9889.107 |
| 9903.45 | 9934.33 | 9965.21 |
| 10067.77 | 10077.87 | 10087.97 |
| 10088.18 | 10099.92 | 10111.66 |
| 10126.38 | 10138.78 | 10151.18 |
| 10151.41 | 10161.74 | 10172.07 |
| 10172.76 | 10184.81 | 10196.87 |
| 10200.08 | 10212.14 | 10224.19 |
| 10224.65 | 10236.01 | 10247.38 |
| 10249.52 | 10262.23 | 10274.94 |
| 10276.56 | 10285.67 | 10294.77 |
| 10295.62 | 10305.69 | 10315.75 |
| 10334.89 | 10347.33 | 10359.76 |
| 10435.64 | 10450.45 | 10465.26 |
| 10466.56 | 10476.95 | 10487.33 |
| 10499.93 | 10509.8 | 10519.67 |
| 10520.59 | 10535.4 | 10550.21 |
| 10570.41 | 10590.04 | 10609.67 |
| 10615.18 | 10638.37 | 10661.56 |
| 10662.02 | 10684.4 | 10706.79 |
| 10709.31 | 10734.45 | 10759.59 |
| 10761.75 | 10777.84 | 10793.93 |
| 10828.47 | 10847.99 | 10867.5 |
| 10874.06 | 10893.68 | 10913.3 |
| 10951.44 | 10963.37 | 10975.3 |
| 11028.77 | 11056.4 | 11084.03 |
| 11090.89 | 11107.43 | 11123.96 |
| 11132.45 | 11152.43 | 11172.4 |
| 11285.82 | 11305.1 | 11324.39 |
| 11377.88 | 11389.94 | 11401.99 |
| 11402.35 | 11414.43 | 11426.5 |
| 11428.16 | 11442.74 | 11457.32 |
| 11464.41 | 11477.66 | 11490.9 |
| 11491.24 | 11501.47 | 11511.7 |
| 11513.71 | 11530.99 | 11548.26 |
| 11563.85 | 11577.63 | 11591.4 |
| 11613 | 11626.92 | 11640.84 |
| 11643.86 | 11657.11 | 11670.36 |
| 11670.69 | 11686.46 | 11702.22 |
| 11719.74 | 11732.72 | 11745.69 |
| 11746.38 | 11756.13 | 11765.89 |
| 11769.8 | 11786.1 | 11802.4 |
| 11822.14 | 11835.46 | 11848.77 |
| 11867.09 | 11883.39 | 11899.68 |
| 11900.2 | 11913.4 | 11926.61 |
| 11927.82 | 11938.26 | 11948.69 |
| 11949.11 | 11964.95 | 11980.79 |
| 11980.83 | 12004.32 | 12027.8 |
| 12064.36 | 12080.32 | 12096.27 |
| 12266.86 | 12290.16 | 12313.47 |
| 12436.99 | 12459.03 | 12481.07 |
| 12546.5 | 12573.59 | 12600.69 |
| 12601.37 | 12615.26 | 12629.15 |
| 12661.3 | 12674.73 | 12688.16 |
| 12723.06 | 12738.33 | 12753.59 |
| 12769.89 | 12789.06 | 12808.24 |
| 12830.74 | 12870.91 | 12911.09 |
| 12937.95 | 12962.98 | 12988.01 |
| 13049.54 | 13076.86 | 13104.18 |
| 13119.56 | 13135.29 | 13151.02 |
| 13259.38 | 13273.73 | 13288.08 |
| 13304.84 | 13325.96 | 13347.09 |
| 13349.01 | 13365.97 | 13382.93 |
| 13510.31 | 13524.23 | 13538.16 |
| 13598.03 | 13619.61 | 13641.19 |
| 13700.43 | 13720.06 | 13739.69 |
| 13739.92 | 13781.47 | 13823.03 |
| 13826.35 | 13845.18 | 13864.02 |
| 13864.91 | 13894.51 | 13924.11 |
| 13925.45 | 13942.27 | 13959.08 |
| 13959.98 | 13981.28 | 14002.58 |
| 14008.41 | 14042.49 | 14076.57 |
| 14077.02 | 14099.66 | 14122.31 |
| 14124.55 | 14152.13 | 14179.7 |

-continued

| Feature Definitions | | |
|---|---|---|
| Left m/z | Center m/z | Right m/z |
| 14180.6 | 14204.59 | 14228.58 |
| 14229.93 | 14254.82 | 14279.7 |
| 14280.6 | 14301.9 | 14323.2 |
| 14412.88 | 14435.3 | 14457.73 |
| 14464.45 | 14489.34 | 14514.23 |
| 14516.47 | 14543.37 | 14570.28 |
| 14571.18 | 14594.72 | 14618.26 |
| 14707.6 | 14727.24 | 14746.88 |
| 14764.89 | 14786.87 | 14808.84 |
| 14859.96 | 14882.15 | 14904.35 |
| 14951.88 | 14980.13 | 15008.38 |
| 15519.58 | 15560.39 | 15601.2 |
| 15717.5 | 15751.16 | 15784.83 |
| 16261.72 | 16302.97 | 16344.23 |
| 16447.74 | 16504.38 | 16561.02 |
| 16607.55 | 16625.96 | 16644.36 |
| 17771.55 | 17809.44 | 17847.33 |
| 17971.11 | 17996.07 | 18021.03 |
| 18021.82 | 18048.07 | 18074.32 |
| 18248.22 | 18280.06 | 18311.89 |
| 18594.4 | 18638.57 | 18682.74 |
| 18811.43 | 18848.65 | 18885.87 |
| 19822.65 | 19999.45 | 20176.24 |
| 20808.15 | 20831.29 | 20854.43 |
| 20873.86 | 20939.16 | 21004.45 |
| 21006.87 | 21065.87 | 21124.88 |
| 21125.85 | 21173.49 | 21221.13 |
| 21221.61 | 21272.15 | 21322.7 |
| 21323.18 | 21373.24 | 21423.3 |
| 21636.47 | 21786.47 | 21936.48 |
| 22991.54 | 23049.38 | 23107.22 |
| 23107.99 | 23155.81 | 23203.63 |
| 23205.94 | 23266.87 | 23327.8 |
| 23404.15 | 23469.71 | 23535.26 |
| 27895.09 | 27945.61 | 27996.12 |
| 27999.21 | 28074.02 | 28148.83 |

wherein the mass spectrometer test is conducted using a mass spectrometer and wherein the integrated intensity values are processed in a first stage classification algorithm using a training set comprising class-labeled spectra produced from blood-based samples from the same type of cancer patients to identify the patient as being in a class of patients determined to be a poor prognosis subgroup corresponding to a class label for the blood-based sample, and (b) responsive to identification of the patient as being in the class of patients determined to be a poor prognosis subgroup, wherein the integrated intensity values are processed in a second stage classification algorithm using a training set comprising class-labeled spectra produced from blood-based samples from the same type of cancer patients treated with an immunotherapy drug to revise the class label to Late or an equivalent which guides treatment of the patient to the immunotherapy drug; and (c) administering the immunotherapy drug to the cancer patient.

5. The method of claim 4, wherein the immunotherapy drug comprises an antibody drug blocking ligand activation of a PD-1 checkpoint protein, anti-CTLA4 drugs, high dose interleukin-2, and combination therapies.

6. The method of claim 4, wherein the immunotherapy drug comprises a combination of two immunotherapy drugs.

7. A method of treating a lung cancer patient, a renal cell carcinoma patient, or a melanoma patient with an immunotherapy drug comprising the steps of:

(a) conducting a mass spectrometer test on a blood-based sample of the cancer patient to obtain a mass spectrum comprising integrated intensity values of selected features in the mass spectrum at one or more m/z ranges as shown in a table below:

| Feature Definitions | | |
|---|---|---|
| Left m/z | Center m/z | Right m/z |
| 3071.217 | 3085.189 | 3099.162 |
| 3099.644 | 3111.208 | 3122.771 |
| 3124.217 | 3144.212 | 3164.207 |
| 3192.341 | 3210.692 | 3229.043 |
| 3230.998 | 3243.532 | 3256.066 |
| 3296.707 | 3322.484 | 3348.261 |
| 3348.743 | 3363.679 | 3378.615 |
| 3379.097 | 3390.661 | 3402.224 |
| 3402.706 | 3418.124 | 3433.542 |
| 3434.506 | 3443.901 | 3453.297 |
| 3454.261 | 3462.933 | 3471.606 |
| 3486.542 | 3503.888 | 3521.233 |
| 3530.869 | 3553.033 | 3575.196 |
| 3583.137 | 3593.094 | 3603.051 |
| 3671.811 | 3682.716 | 3693.621 |
| 3694.825 | 3704.05 | 3713.275 |
| 3713.375 | 3723.478 | 3733.581 |
| 3759.25 | 3772.741 | 3786.232 |
| 3786.267 | 3795.511 | 3804.756 |
| 3805.438 | 3818.133 | 3830.828 |
| 3832.004 | 3841.641 | 3851.277 |
| 3877.777 | 3888.136 | 3898.495 |
| 3899.283 | 3907.43 | 3915.577 |
| 3915.701 | 3927.75 | 3939.799 |
| 3940.413 | 3952.458 | 3964.504 |
| 3995.34 | 4009.553 | 4023.767 |
| 4024.145 | 4031.508 | 4038.872 |
| 4039.254 | 4051.399 | 4063.544 |
| 4080.139 | 4094.835 | 4109.53 |
| 4112.173 | 4119.373 | 4126.573 |
| 4127.254 | 4133.389 | 4139.524 |
| 4165.916 | 4170.823 | 4175.73 |
| 4198.946 | 4210.815 | 4222.684 |
| 4252.63 | 4262.507 | 4272.384 |
| 4272.866 | 4287.802 | 4302.738 |
| 4322.975 | 4336.947 | 4350.92 |
| 4351.402 | 4359.834 | 4368.265 |
| 4369.229 | 4380.07 | 4390.911 |
| 4392.356 | 4408.979 | 4425.602 |
| 4426.151 | 4433.527 | 4440.903 |
| 4445.65 | 4462.521 | 4479.392 |
| 4493.056 | 4506.065 | 4519.074 |
| 4539.6 | 4546.345 | 4553.091 |
| 4553.295 | 4565.565 | 4577.835 |
| 4578.09 | 4590.487 | 4602.884 |
| 4610.619 | 4621.942 | 4633.264 |
| 4633.746 | 4642.419 | 4651.091 |
| 4668.351 | 4674.256 | 4680.16 |
| 4680.315 | 4686.375 | 4692.434 |
| 4694.454 | 4714.187 | 4733.919 |
| 4745.595 | 4755.26 | 4764.925 |
| 4767.31 | 4773.529 | 4779.749 |
| 4780.015 | 4789.426 | 4798.836 |
| 4801.9 | 4818.041 | 4834.181 |
| 4836.109 | 4856.827 | 4877.545 |
| 4878.027 | 4891.999 | 4905.972 |
| 4927.529 | 4935.668 | 4943.807 |
| 4948.646 | 4959.134 | 4969.622 |
| 4970.088 | 4977.701 | 4985.314 |
| 4986.713 | 4999.065 | 5011.417 |
| 5012.505 | 5022.06 | 5031.616 |
| 5033.636 | 5041.171 | 5048.707 |
| 5049.071 | 5067.139 | 5085.208 |
| 5087.135 | 5104.48 | 5121.826 |
| 5121.888 | 5127.87 | 5133.852 |
| 5134.353 | 5148.085 | 5161.816 |
| 5164.707 | 5176.994 | 5189.28 |
| 5211.228 | 5223.658 | 5236.088 |
| 5263.479 | 5288.052 | 5312.625 |
| 5330.753 | 5340.697 | 5350.642 |

-continued

| Feature Definitions | | |
|---|---|---|
| Left m/z | Center m/z | Right m/z |
| 5351.59 | 5362.357 | 5373.124 |
| 5395.675 | 5407.035 | 5418.395 |
| 5419.379 | 5428.197 | 5437.016 |
| 5442.725 | 5449.541 | 5456.357 |
| 5503.424 | 5519.324 | 5535.224 |
| 5537.824 | 5549.322 | 5560.82 |
| 5561.13 | 5570.453 | 5579.775 |
| 5666.474 | 5674.786 | 5683.099 |
| 5684.186 | 5691.955 | 5699.724 |
| 5699.879 | 5705.55 | 5711.222 |
| 5714.459 | 5720.241 | 5726.023 |
| 5726.029 | 5734.422 | 5742.814 |
| 5767.795 | 5777.164 | 5786.533 |
| 5803.887 | 5810.076 | 5816.265 |
| 5816.42 | 5822.763 | 5829.107 |
| 5832.023 | 5840.458 | 5848.894 |
| 5856.954 | 5868.25 | 5879.546 |
| 5879.588 | 5888.744 | 5897.9 |
| 5898.07 | 5909.769 | 5921.469 |
| 5923.788 | 5933.502 | 5943.215 |
| 5943.385 | 5952.758 | 5962.13 |
| 5973.586 | 5985.249 | 5996.913 |
| 5998.015 | 6008.576 | 6019.137 |
| 6019.872 | 6027.31 | 6034.749 |
| 6035.3 | 6042.831 | 6050.361 |
| 6067.076 | 6081.127 | 6095.178 |
| 6095.912 | 6108.218 | 6120.524 |
| 6186.655 | 6194.454 | 6202.254 |
| 6202.492 | 6209.862 | 6217.232 |
| 6217.504 | 6227.514 | 6237.524 |
| 6275.163 | 6284.15 | 6293.136 |
| 6293.984 | 6303.479 | 6312.974 |
| 6321.463 | 6332.667 | 6343.871 |
| 6346.716 | 6356.381 | 6366.045 |
| 6378.768 | 6393.095 | 6407.421 |
| 6407.605 | 6438.187 | 6468.768 |
| 6470.605 | 6487.319 | 6504.033 |
| 6521.115 | 6534.982 | 6548.849 |
| 6575.849 | 6589.257 | 6602.666 |
| 6603.584 | 6652.9 | 6702.216 |
| 6715.257 | 6730.594 | 6745.93 |
| 6798.461 | 6809.114 | 6819.767 |
| 6825.828 | 6837.675 | 6849.522 |
| 6849.889 | 6859.44 | 6868.991 |
| 6869.175 | 6890.297 | 6911.42 |
| 6911.603 | 6920.971 | 6930.338 |
| 6931.256 | 6947.144 | 6963.032 |
| 6963.583 | 6971.113 | 6978.644 |
| 6979.011 | 6995.266 | 7011.521 |
| 7012.072 | 7021.072 | 7030.072 |
| 7030.256 | 7035.123 | 7039.991 |
| 7040.358 | 7053.491 | 7066.623 |
| 7066.991 | 7075.623 | 7084.256 |
| 7118.235 | 7143.949 | 7169.664 |
| 7178.664 | 7189.317 | 7199.97 |
| 7231.745 | 7242.949 | 7254.153 |
| 7254.704 | 7269.031 | 7283.357 |
| 7283.908 | 7296.949 | 7309.99 |
| 7310.541 | 7341.306 | 7372.071 |
| 7375.194 | 7390.071 | 7404.949 |
| 7405.5 | 7418.632 | 7431.765 |
| 7433.234 | 7447.101 | 7460.969 |
| 7461.887 | 7471.622 | 7481.356 |
| 7524.336 | 7537.193 | 7550.05 |
| 7603.315 | 7617.366 | 7631.417 |
| 7639.922 | 7651.028 | 7662.134 |
| 7704.863 | 7713.35 | 7721.837 |
| 7729.987 | 7736.204 | 7742.42 |
| 7742.834 | 7750.915 | 7758.997 |
| 7760.24 | 7767.769 | 7775.297 |
| 7776.519 | 7788.917 | 7801.314 |
| 7811.174 | 7827.282 | 7843.39 |
| 7871.875 | 7881.201 | 7890.527 |
| 7905.09 | 7914.09 | 7923.09 |
| 7984.804 | 7994.906 | 8005.008 |

-continued

| Feature Definitions | | |
|---|---|---|
| Left m/z | Center m/z | Right m/z |
| 8006.661 | 8018.691 | 8030.722 |
| 8131.007 | 8153.048 | 8175.089 |
| 8192.538 | 8215.68 | 8238.823 |
| 8239.925 | 8254.895 | 8269.864 |
| 8307.149 | 8329.925 | 8352.7 |
| 8353.435 | 8364.455 | 8375.476 |
| 8378.598 | 8391.272 | 8403.945 |
| 8404.496 | 8413.955 | 8423.414 |
| 8423.598 | 8432.965 | 8442.333 |
| 8457.388 | 8464.68 | 8471.972 |
| 8472.104 | 8479.131 | 8486.157 |
| 8495.334 | 8507.712 | 8520.089 |
| 8520.598 | 8531.958 | 8543.319 |
| 8555.291 | 8565.118 | 8574.944 |
| 8575.312 | 8592.026 | 8608.74 |
| 8650.067 | 8661.913 | 8673.76 |
| 8719.855 | 8724.498 | 8729.142 |
| 8757.148 | 8771.291 | 8785.433 |
| 8800.495 | 8826.76 | 8853.025 |
| 8860.556 | 8871.76 | 8882.964 |
| 8883.698 | 8894.811 | 8905.923 |
| 8906.29 | 8932.096 | 8957.902 |
| 8966.168 | 8976.729 | 8987.29 |
| 8988.025 | 8998.678 | 9009.331 |
| 9009.882 | 9020.259 | 9030.637 |
| 9031.739 | 9041.657 | 9051.575 |
| 9056.496 | 9062.396 | 9068.296 |
| 9068.959 | 9078.57 | 9088.182 |
| 9089.963 | 9098.136 | 9106.31 |
| 9113.473 | 9142.493 | 9171.514 |
| 9196.31 | 9207.881 | 9219.452 |
| 9233.962 | 9244.34 | 9254.718 |
| 9254.901 | 9262.891 | 9270.881 |
| 9271.064 | 9281.258 | 9291.452 |
| 9308.35 | 9319.83 | 9331.309 |
| 9345.773 | 9366.207 | 9386.641 |
| 9387.1 | 9398.694 | 9410.288 |
| 9411.207 | 9454.025 | 9496.844 |
| 9554.472 | 9573.413 | 9592.354 |
| 9613.476 | 9626.563 | 9639.65 |
| 9640.109 | 9654.688 | 9669.267 |
| 9688.553 | 9723.565 | 9758.578 |
| 9779.012 | 9790.95 | 9802.889 |
| 9843.016 | 9866.062 | 9889.107 |
| 9903.45 | 9934.33 | 9965.21 |
| 10067.77 | 10077.87 | 10087.97 |
| 10088.18 | 10099.92 | 10111.66 |
| 10126.38 | 10138.78 | 10151.18 |
| 10151.41 | 10161.74 | 10172.07 |
| 10172.76 | 10184.81 | 10196.87 |
| 10200.08 | 10212.14 | 10224.19 |
| 10224.65 | 10236.01 | 10247.38 |
| 10249.52 | 10262.23 | 10274.94 |
| 10276.56 | 10285.67 | 10294.77 |
| 10295.62 | 10305.69 | 10315.75 |
| 10334.89 | 10347.33 | 10359.76 |
| 10435.64 | 10450.45 | 10465.26 |
| 10466.56 | 10476.95 | 10487.33 |
| 10499.93 | 10509.8 | 10519.67 |
| 10520.59 | 10535.4 | 10550.21 |
| 10570.41 | 10590.04 | 10609.67 |
| 10615.18 | 10638.37 | 10661.56 |
| 10662.02 | 10684.4 | 10706.79 |
| 10709.31 | 10734.45 | 10759.59 |
| 10761.75 | 10777.84 | 10793.93 |
| 10828.47 | 10847.99 | 10867.5 |
| 10874.06 | 10893.68 | 10913.3 |
| 10951.44 | 10963.37 | 10975.3 |
| 11028.77 | 11056.4 | 11084.03 |
| 11090.89 | 11107.43 | 11123.96 |
| 11132.45 | 11152.43 | 11172.4 |
| 11285.82 | 11305.1 | 11324.39 |
| 11377.88 | 11389.94 | 11401.99 |
| 11402.35 | 11414.43 | 11426.5 |
| 11428.16 | 11442.74 | 11457.32 |

-continued

| Feature Definitions | | |
|---|---|---|
| Left m/z | Center m/z | Right m/z |
| 11464.41 | 11477.66 | 11490.9 |
| 11491.24 | 11501.47 | 11511.7 |
| 11513.71 | 11530.99 | 11548.26 |
| 11563.85 | 11577.63 | 11591.4 |
| 11613 | 11626.92 | 11640.84 |
| 11643.86 | 11657.11 | 11670.36 |
| 11670.69 | 11686.46 | 11702.22 |
| 11719.74 | 11732.72 | 11745.69 |
| 11746.38 | 11756.13 | 11765.89 |
| 11769.8 | 11786.1 | 11802.4 |
| 11822.14 | 11835.46 | 11848.77 |
| 11867.09 | 11883.39 | 11899.68 |
| 11900.2 | 11913.4 | 11926.61 |
| 11927.82 | 11938.26 | 11948.69 |
| 11949.11 | 11964.95 | 11980.79 |
| 11980.83 | 12004.32 | 12027.8 |
| 12064.36 | 12080.32 | 12096.27 |
| 12266.86 | 12290.16 | 12313.47 |
| 12436.99 | 12459.03 | 12481.07 |
| 12546.5 | 12573.59 | 12600.69 |
| 12601.37 | 12615.26 | 12629.15 |
| 12661.3 | 12674.73 | 12688.16 |
| 12723.06 | 12738.33 | 12753.59 |
| 12769.89 | 12789.06 | 12808.24 |
| 12830.74 | 12870.91 | 12911.09 |
| 12937.95 | 12962.98 | 12988.01 |
| 13049.54 | 13076.86 | 13104.18 |
| 13119.56 | 13135.29 | 13151.02 |
| 13259.38 | 13273.73 | 13288.08 |
| 13304.84 | 13325.96 | 13347.09 |
| 13349.01 | 13365.97 | 13382.93 |
| 13510.31 | 13524.23 | 13538.16 |
| 13598.03 | 13619.61 | 13641.19 |
| 13700.43 | 13720.06 | 13739.69 |
| 13739.92 | 13781.47 | 13823.03 |
| 13826.35 | 13845.18 | 13864.02 |
| 13864.91 | 13894.51 | 13924.11 |
| 13925.45 | 13942.27 | 13959.08 |
| 13959.98 | 13981.28 | 14002.58 |
| 14008.41 | 14042.49 | 14076.57 |
| 14077.02 | 14099.66 | 14122.31 |
| 14124.55 | 14152.13 | 14179.7 |
| 14180.6 | 14204.59 | 14228.58 |
| 14229.93 | 14254.82 | 14279.7 |
| 14280.6 | 14301.9 | 14323.2 |
| 14412.88 | 14435.3 | 14457.73 |
| 14464.45 | 14489.34 | 14514.23 |
| 14516.47 | 14543.37 | 14570.28 |
| 14571.18 | 14594.72 | 14618.26 |
| 14707.6 | 14727.24 | 14746.88 |
| 14764.89 | 14786.87 | 14808.84 |
| 14859.96 | 14882.15 | 14904.35 |
| 14951.88 | 14980.13 | 15008.38 |
| 15519.58 | 15560.39 | 15601.2 |
| 15717.5 | 15751.16 | 15784.83 |
| 16261.72 | 16302.97 | 16344.23 |
| 16447.74 | 16504.38 | 16561.02 |
| 16607.55 | 16625.96 | 16644.36 |
| 17771.55 | 17809.44 | 17847.33 |
| 17971.11 | 17996.07 | 18021.03 |
| 18021.82 | 18048.07 | 18074.32 |
| 18248.22 | 18280.06 | 18311.89 |
| 18594.4 | 18638.57 | 18682.74 |
| 18811.43 | 18848.65 | 18885.87 |
| 19822.65 | 19999.45 | 20176.24 |
| 20808.15 | 20831.29 | 20854.43 |
| 20873.86 | 20939.16 | 21004.45 |
| 21006.87 | 21065.87 | 21124.88 |
| 21125.85 | 21173.49 | 21221.13 |
| 21221.61 | 21272.15 | 21322.7 |
| 21323.18 | 21373.24 | 21423.3 |
| 21636.47 | 21786.47 | 21936.48 |
| 22991.54 | 23049.38 | 23107.22 |
| 23107.99 | 23155.81 | 23203.63 |
| 23205.94 | 23266.87 | 23327.8 |

-continued

| Feature Definitions | | |
| --- | --- | --- |
| Left m/z | Center m/z | Right m/z |
| 23404.15 | 23469.71 | 23535.26 |
| 27895.09 | 27945.61 | 27996.12 |
| 27999.21 | 28074.02 | 28148.83 |

wherein the mass spectrometer test is conducted using a mass spectrometer and wherein the integrated intensity values are processed in a first stage classification algorithm using a training set comprising class-labeled spectra produced from blood-based samples from the same type of cancer patients to identify the patient as being in a class of patients determined to be a poor prognosis subgroup corresponding to a class label for the blood-based sample, (b) responsive to identification of the patient as being in the class of patients determined to be a poor prognosis subgroup, wherein the integrated intensity values as shown in the table are processed in a second stage classification algorithm using a training set comprising class-labeled spectra produced from blood-based samples from the same type of cancer patients treated with an immunotherapy drug to a class label revised to Late or an equivalent which identifies the patient as likely to have durable benefit from the immunotherapy drug; and (c) determining that the patient having the class label of Late or the equivalent is likely to respond to an immunotherapy drug; and (d) administering the immunotherapy drug to the cancer patient.

8. The method of claim 7, wherein the immunotherapy drug comprises an antibody drug blocking ligand activation of a PD-1 checkpoint protein, anti-CTLA4 drugs, high dose interleukin-2, and combination therapies.

9. The method of claim 7, wherein the immunotherapy drug comprises a combination of two immunotherapy drugs.

10. The method of claim 1, further comprising changing the class label for the sample responsive to operating on the mass spectral data with the programmed computer implementing the second stage classification algorithm from a first class label to a second class label.

11. The method of claim 1, the training set comprises a number of blood-based samples that is less than a number of attributes of the blood-based sample.

* * * * *